US010077295B2

(12) United States Patent
Tisdale et al.

(10) Patent No.: US 10,077,295 B2
(45) Date of Patent: Sep. 18, 2018

(54) GLYCOPROTEINS HAVING LIPID MOBILIZING PROPERTIES AND THERAPEUTIC USES THEREOF

(71) Applicant: Aston University, Birmingham (GB)

(72) Inventors: Michael J. Tisdale, Claverdon (GB); Steven Russell, Wedensbury (GB)

(73) Assignee: Aston University, Birmingham (GB)

( * ) Notice: Subject to any disclaimer, the term of this patent is extended or adjusted under 35 U.S.C. 154(b) by 0 days.

(21) Appl. No.: 15/238,051

(22) Filed: Aug. 16, 2016

(65) Prior Publication Data

US 2017/0088594 A1 Mar. 30, 2017

Related U.S. Application Data

(63) Continuation of application No. 15/064,307, filed on Mar. 8, 2016, now abandoned, which is a continuation of application No. 14/266,371, filed on Apr. 30, 2014, now abandoned, which is a continuation of application No. 13/805,190, filed as application No. PCT/GB2011/000966 on Jun. 27, 2011, now abandoned.

(60) Provisional application No. 61/420,677, filed on Dec. 7, 2010, provisional application No. 61/384,652, filed on Sep. 20, 2010, provisional application No. 61/358,596, filed on Jun. 25, 2010.

(51) Int. Cl.
| | |
|---|---|
| A61K 38/00 | (2006.01) |
| A61K 38/28 | (2006.01) |
| C07K 14/47 | (2006.01) |
| A61K 9/00 | (2006.01) |
| A61K 31/137 | (2006.01) |
| A61K 38/17 | (2006.01) |
| A61K 38/26 | (2006.01) |
| A61K 31/138 | (2006.01) |
| A61K 45/06 | (2006.01) |
| A23L 33/17 | (2016.01) |
| A61K 47/60 | (2017.01) |
| A61K 47/61 | (2017.01) |

(52) U.S. Cl.
CPC ............ *C07K 14/473* (2013.01); *A23L 33/17* (2016.08); *A61K 9/0014* (2013.01); *A61K 9/0043* (2013.01); *A61K 9/0053* (2013.01); *A61K 31/137* (2013.01); *A61K 31/138* (2013.01); *A61K 38/17* (2013.01); *A61K 38/1709* (2013.01); *A61K 38/1741* (2013.01); *A61K 38/26* (2013.01); *A61K 38/28* (2013.01); *A61K 45/06* (2013.01); *A61K 47/60* (2017.08); *A61K 47/61* (2017.08)

(58) Field of Classification Search
None
See application file for complete search history.

(56) References Cited

U.S. PATENT DOCUMENTS

| | | |
|---|---|---|
| 6,890,899 B1 | 5/2005 | Tisdale |
| 2003/0236190 A1 | 12/2003 | Pillutla et al. |
| 2004/0014639 A1 | 1/2004 | Belyea et al. |
| 2005/0148763 A1 | 7/2005 | Sekimori et al. |
| 2013/0143791 A1 | 6/2013 | Tisdale |
| 2014/0235534 A1 | 8/2014 | Tisdale |

FOREIGN PATENT DOCUMENTS

| | | |
|---|---|---|
| JP | 2002-519303 A | 12/1999 |
| WO | 9962939 | 12/1999 |
| WO | 2010/052563 A2 | 5/2010 |

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Amour et al. 2007. Anesthesiology. 107:452-60.*
EP11729337.3 Communication pursuant to Rule 164(2)(b) and Article 94(3) EPC mailed Mar. 8, 2017.
Russell and Tisdale. "Studies on the Anti-Obesity Activity of Zinc-a2-Glycoprotein in the Rat." International Journal of Obesity, 2011, 35(5)658-665.
Russell and Tisdale. "Mechanism of Attentuation of Skeletal Muscle Atrophy by Zinc-a2-Glycoprotein." Endocrinology, 2010, 151(10)4696-4704.
Russell and Tisdale. "Role of [beta]-Adrenergic Receptors in the Oral Activity of Zinc-a2-Glycoprotein (ZAG)." Endocrinology, Oct. 2012, 153(10)4696-4704.
Capelle et al., "High Throughout Screening of Protein Formulation Stability: Practical Considerations," Eur. J. Pharmaceut. Biopharmaceut., 2007, 65:131-148, Elsevier B.V.
Russell and Tisdale, "The Role of Glucocorticoids in the Induction of Zinc-a2-Glycoprotein Expression in Adipose Tissue in Cancer Cachexia," Br. J. Cancer, 2005, 92:876-881, Cancer Research UK.
Russell and Tisdale, "Antidiabetic Properties of Zinc-a2-Glycoprotein in ob/ob Mice," Endocrinology, 2010, 151:948-957, The Endocrine Society.
Russell and Tisdale, "Studies on the Antiobesity Effect of Zinc-a2-Glycoprotein in the ob/ob Mouse," Intl. J. Obes. 2011, 35:345-354, Macmillan Publishers Limited.
Russell et al., "Induction of Lipolysis in Vitro and Loss of Body Fat in Vivo by Zinc-a2-Glycoprotein," Biochim. et Biophys. Acta, 2004, 1636-59-68, Elsevier B.V.

(Continued)

*Primary Examiner* — Shulamith H Shafer
(74) *Attorney, Agent, or Firm* — Wagenknecht IP Law Group, PC

(57) ABSTRACT

The invention provides formulations and methods for ameliorating symptoms associated with metabolic disorders, such as cachexia, hypoglycemia, obesity, diabetes, and the like by administering Zn-$\alpha_2$-glycoproteins or a functional fragment thereof, alone or in combination with additional agents, such as β adrenergin receptor agonists, β adrenergin receptor antagonists, and/or glycemic control agents.

16 Claims, 58 Drawing Sheets

Specification includes a Sequence Listing.

(56) References Cited

OTHER PUBLICATIONS

Sanders and Tisdale, "Effect of Zinc-a2-Glycoprotein (ZAG) on Expression of Uncoupling Proteins in Skeletal Muscle and Adipose Tissue," Caner Lett., 2004, 212:71-81, Elsevier Ireland Ltd.
Hirai et al., "Biological evaluation of a lipid-mobilizing factor isolated from the urine of cancer patients." Cancer Res. Jun. 1, 1998, 58(11)2359-2365.
Mracek et al. "The Adipokine Zinc-a2-Glycoprotein (ZAG) is Downregulated with Fat Mass Expansion in Obesity," Endocrinol., 2010, 72(3)334-341.
JP 2013-515962 Office Action dated May 27, 2015.

\* cited by examiner vis ep sc

Gln Glu Asn Gln Asp Gly Arg Tyr Ser Leu Thr
Tyr Ile Tyr Thr Gly Leu Ser Lys His Val Glu
Asp Val Pro Ala Phe Gln Ala Leu Gly Ser Leu
Asn Asp Leu Gln Phe Phe Arg Tyr Asn Ser Lys
Asp Arg Lys Ser Gln Pro Met Gly Leu Trp Arg
Gln Val Glu Gly Met Glu Asp Trp Lys Glu Asp
Ser Gln Leu Gln Lys Ala Arg Glu Asp Met Glu
Thr Leu Lys Asp Ile Val Glu Tyr Tyr Asn Asp
Ser Asn Gly Ser His Val Leu Gln Gly Arg Phe
Gly Cys Glu Ile Glu Asn Asn Arg Ser Ser Gly
Ala Phe Trp Lys Tyr Tyr Tyr Asp Gly Lys Asp
Tyr Ile Glu Phe Asn Lys Glu Ile Pro Ala Trp
Val Pro Phe Asp Pro Ala Ala Gln Ile Thr Lys
Gln Lys Trp Glu Ala Glu Pro Val Tyr Val Gln
Arg Ala Lys Ala Tyr Leu Glu Glu Glu Cys Pro
Ala Thr Leu Arg Lys Tyr Leu Lys Tyr Ser Lys
Asn Ile Leu Asp Arg Gln Asp Pro Pro Ser Val
Val Val Thr Ser His Gln Ala Pro Gly Glu Lys
Lys Lys Leu Lys Cys Leu Ala Tyr Asp Phe Tyr
Pro Gly Lys Ile Asp Val His Trp Thr Arg Ala
Gly Gln Val Gln Glu Pro Glu Leu Arg Gly Asp
Val Leu His Asn Gly Asn Gly Thr Tyr Gln Ser
Trp Val Val Val Ala Val Pro Pro Gln Asp Thr
Ala Pro Tyr Ser Cys His Val Gln His Ser Ser
Leu Ala Gln Pro Leu Val Val Pro Trp Glu Ala
Ser COOH

FIG. 10

Net Protein Synthesis in Skeletal Muscle is Up-Regulated

Western blot of mouse ZAG in p.o. dosed plasma samples

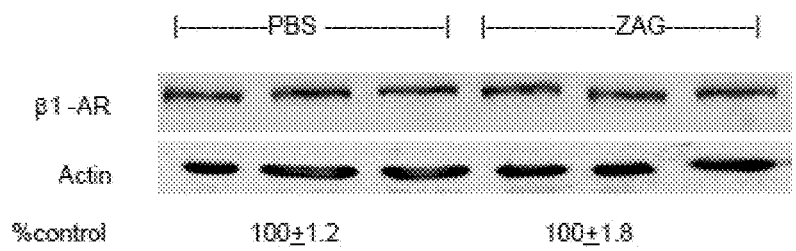
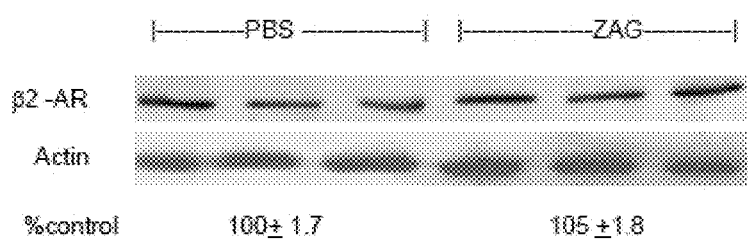
FIG. 56A
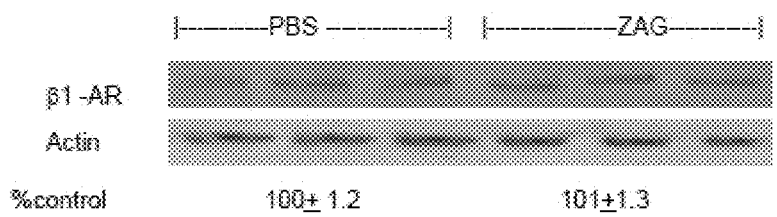
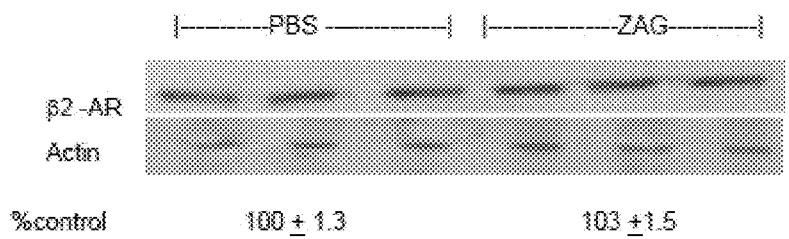
FIG. 56B

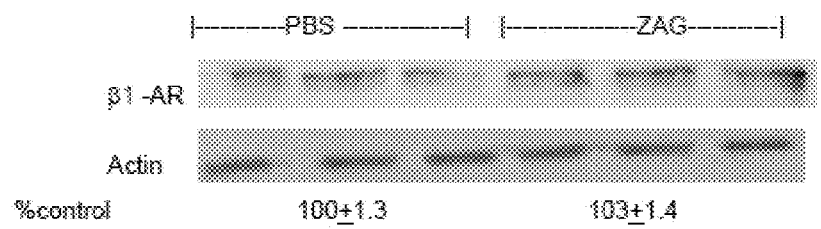
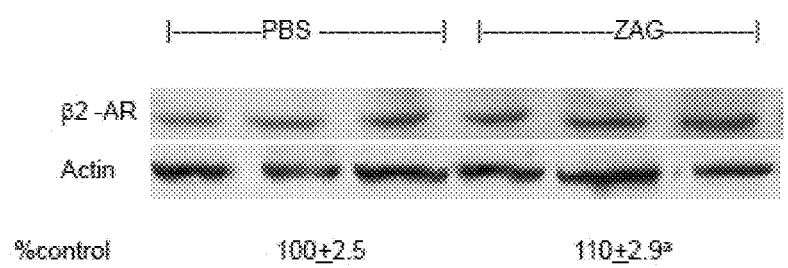
FIG. 56C
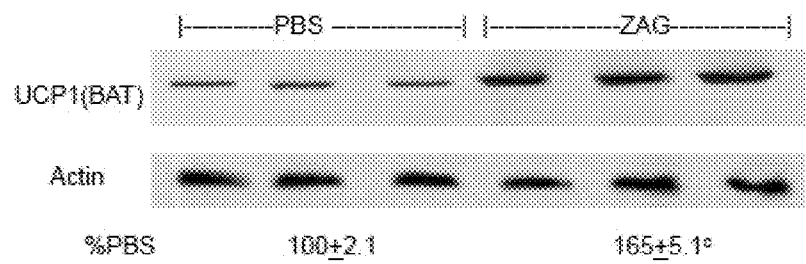
FIG. 57A

SEQUENCE LISTING

```
<160> NUMBER OF SEQ ID NOS: 7

<210> SEQ ID NO 1
<211> LENGTH: 276
<212> TYPE: PRT
<213> ORGANISM: Homo sapiens

<400> SEQUENCE: 1

Gln Glu Asn Gln Asp Gly Arg Tyr Ser Leu Thr Tyr Ile Tyr Thr Gly
1               5                   10                  15

Leu Ser Lys His Val Glu Asp Val Pro Ala Phe Gln Ala Leu Gly Ser
            20                  25                  30

Leu Asn Asp Leu Gln Phe Phe Arg Tyr Asn Ser Lys Asp Arg Lys Ser
        35                  40                  45

Gln Pro Met Gly Leu Trp Arg Gln Val Glu Gly Met Glu Asp Trp Lys
    50                  55                  60

Glu Asp Ser Gln Leu Gln Lys Ala Arg Glu Asp Met Glu Thr Leu Lys
65                  70                  75                  80

Asp Ile Val Glu Tyr Tyr Asn Asp Ser Asn Gly Ser His Val Leu Gln
                85                  90                  95

Gly Arg Phe Gly Cys Glu Ile Glu Asn Asn Arg Ser Ser Gly Ala Phe
            100                 105                 110

Trp Lys Tyr Tyr Tyr Asp Gly Lys Asp Tyr Ile Glu Phe Asn Lys Glu
        115                 120                 125

Ile Pro Ala Trp Val Pro Phe Asp Pro Ala Ala Gln Ile Thr Lys Gln
    130                 135                 140

Lys Trp Glu Ala Glu Pro Val Tyr Val Gln Arg Ala Lys Ala Tyr Leu
145                 150                 155                 160

Glu Glu Glu Cys Pro Ala Thr Leu Arg Lys Tyr Leu Lys Tyr Ser Lys
                165                 170                 175
```

```
Asn Ile Leu Asp Arg Gln Asp Pro Pro Ser Val Val Thr Ser His
            180                 185                 190

Gln Ala Pro Gly Glu Lys Lys Lys Leu Lys Cys Leu Ala Tyr Asp Phe
        195                 200                 205

Tyr Pro Gly Lys Ile Asp Val His Trp Thr Arg Ala Gly Gln Val Gln
210                 215                 220

Glu Pro Glu Leu Arg Gly Asp Val Leu His Asn Gly Asn Gly Thr Tyr
225                 230                 235                 240

Gln Ser Trp Val Val Val Ala Val Pro Pro Gln Asp Thr Ala Pro Tyr
                245                 250                 255

Ser Cys His Val Gln His Ser Ser Leu Ala Gln Pro Leu Val Val Pro
            260                 265                 270

Trp Glu Ala Ser
        275

<210> SEQ ID NO 2
<211> LENGTH: 4
<212> TYPE: PRT
<213> ORGANISM: Artificial sequence
<220> FEATURE:
<223> OTHER INFORMATION: Synthetic construct

<400> SEQUENCE: 2

Lys Lys Val Tyr
1

<210> SEQ ID NO 3
<211> LENGTH: 4
<212> TYPE: PRT
<213> ORGANISM: Artificial sequence
<220> FEATURE:
<223> OTHER INFORMATION: Synthetic construct

<400> SEQUENCE: 3

Asp Gly Val Asp
1

<210> SEQ ID NO 4
<211> LENGTH: 5
<212> TYPE: PRT
<213> ORGANISM: Artificial sequence
<220> FEATURE:
<223> OTHER INFORMATION: Synthetic construct

<400> SEQUENCE: 4

Ile Glu Phe Thr Asp
1               5

<210> SEQ ID NO 5
<211> LENGTH: 4
<212> TYPE: PRT
<213> ORGANISM: Artificial sequence
<220> FEATURE:
<223> OTHER INFORMATION: Synthetic construct

<400> SEQUENCE: 5

Asp Glu Val Asp
1

<210> SEQ ID NO 6
<211> LENGTH: 5
<212> TYPE: PRT
<213> ORGANISM: Artificial sequence
```

```
<220> FEATURE:
<223> OTHER INFORMATION: Synthetic construct

<400> SEQUENCE: 6

Ile Glu Phe Thr Asp
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic construct: peptide linker

<400> SEQUENCE: 7

Gly Gly Gly Gly Ser
1               5
```

GLYCOPROTEINS HAVING LIPID MOBILIZING PROPERTIES AND THERAPEUTIC USES THEREOF

CROSS-REFERENCE TO RELATED APPLICATIONS

This application is a continuation of U.S. application Ser. No. 15/064,307, filed Mar. 8, 2016, currently pending, which is a continuation of U.S. application Ser. No. 14/266, 371, filed Apr. 30, 2014, now abandoned, which is a continuation of U.S. application Ser. No. 13/805,190, filed Feb. 20, 2013, now abandoned, which is a 35 USC § 371 National Stage application of International Application No. PCT/GB2011/000966 filed Jun. 27, 2011, now expired, which claims the benefit under 35 USC § 119(e) to U.S. Application Ser. No. 61/420,677, filed Dec. 7, 2010, to U.S. Application Ser. No. 61/384,652 filed Sep. 20, 2010, and to U.S. Application Ser. No. 61/358,596 filed Jun. 25, 2010, all now expired. The disclosure of each of the prior applications is considered part of and is incorporated by reference in the disclosure of this application.

BACKGROUND OF THE INVENTION

Field of the Invention

The present invention relates generally to medicinal formulations and supplements, and more particularly, to formulations and methods for altering the metabolism of a subject, as well as ameliorating disorders such as cachexia, obesity, diabetes and insulin resistance.

Background Information

The prevalence of obesity in adults, children and adolescents has increased rapidly over the past 30 years in the United States and globally and continues to rise. Obesity is classically defined based on the percentage of body fat or, more recently, the body mass index (BMI), also called Quetlet index (National Task Force on the Prevention and Treatment of Obesity, Arch. Intern. Med., 160: 898-904 (2000); Khaodhiar, L. et al., Clin. Cornerstone, 2: 17-31 (1999)). The BMI is defined as the ratio of weight (kg) divided by height (in meters) squared.

Overweight and obesity are associated with increasing the risk of developing many chronic diseases of aging seen in the U.S. Such co-morbidities include type 2 diabetes mellitus, hypertension, coronary heart diseases and dyslipidemia, gallstones and cholecystectomy, osteoarthritis, cancer (of the breast, colon, endometrial, prostate, and gallbladder), and sleep apnea. It is estimated that there are around 325,000 deaths annually that are attributable to obesity. The key to reducing the severity of the diseases is to lose weight effectively. Although about 30 to 40% claim to be trying to lose weight or maintain lost weight, current therapies appear not to be working. Besides dietary manipulation, pharmacological management and in extreme cases, surgery, are sanctioned adjunctive therapies to treat overweight and obese patients (Expert Panel, National Institute of Health, Heart, Lung, and Blood Institute, 1-42 (June 1998); Bray, G. A., Contemporary Diagnosis and Management of Obesity, 246-273 (1998)). Drugs have side effects, and surgery, although effective, is a drastic measure and reserved for morbidly obese.

Cachexia is wasting of both adipose and skeletal muscle mass caused by disease. It occurs in many conditions and is common with many cancers when remission or control fails. Patients with advanced cancer, AIDS, and some other major chronic progressive diseases may appear cachectic. Cachexia can occur in people who are eating enough, but who cannot absorb the nutrients. While cachexia may be mediated by certain cytokines, especially tumor necrosis factor-α, IL-1b, and IL-6, which are produced by tumor cells and host cells in the tissue mass, there is currently no widely accepted treatment for cachexia.

Diabetes mellitus is a major cause of morbidity and mortality. Chronically elevated blood glucose leads to debilitating complications: nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction.

There are two primary types of diabetes. Type I, or insulin-dependent diabetes mellitus (IDDM) is due to autoimmune destruction of insulin-producing beta cells in the pancreatic islets. The onset of this disease is usually in childhood or adolescence. Treatment consists primarily of multiple daily injections of insulin, combined with frequent testing of blood glucose levels to guide adjustment of insulin doses, because excess insulin can cause hypoglycemia and consequent impairment of brain and other functions. Increasing scrutiny is being given to the role of insulin resistance to the genesis, progression, and therapeutic management of this type of diabetic disease.

Type II, or noninsulin-dependent diabetes mellitus (NIDDM) typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance. There are several classes of drugs that are useful for treatment of NIDDM: 1) insulin releasers, which directly stimulate insulin release, carrying the risk of hypoglycemia; 2) prandial insulin releasers, which potentiate glucose-induced insulin secretion, and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; 5) insulin injections, which are often necessary in the later stages of NIDDM when the islets have failed under chronic hyperstimulation.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation (NASH; "nonalcoholic steatohepatitis"), fibrosis, and cirrhosis. Cumulatively, insulin resistance syndromes, including but not limited to diabetes, underlie many of the major causes of morbidity and death of people over age 40.

Despite the existence of such drugs, diabetes remains a major and growing public health problem. Late stage complications of diabetes consume a large proportion of national health care resources. There is a need for new orally active therapeutic agents which effectively address the primary defects of insulin resistance and islet failure with fewer or milder side effects than existing drugs.

Zinc-α$_2$-glycoprotein (ZAG) has been identified as a lipid mobilizing factor (LMF) with the potential to induce fat loss in cancer cacehxia. ZAG was shown to induce lipolysis in white adipocytes by interaction with a β3-adrenergic receptor, while in vivo it increased expression of uncoupling protein-1 (UCP-1) in brown adipose tissue (BAT), and induced loss of body fat. In addition to some tumors, ZAG is also produced by white adipose tissue (WAT) and BAT and its expression is upregulated in cachexia. In contrast ZAG expression in adipose tissue of obese humans was only 30% of that found in non-obese subjects. This suggests that loss of ZAG expression in WAT could account for some of the features of obesity. Certainly inactivation of both ZAG alleles in mice led to an increase in body weight which was more pronounced when the animals were fed a high fat diet. The lipolytic response to various agents was significantly decreased in adipocytes from ZAG deficient animals.

To date studies on the lipid mobilizing effect of ZAG have been carried out in both mice and rats using human and murine ZAG. The studies indicate that ZAG is evolutionarily conserved and exhibits cross-species activity, e.g., murine ZAG exhibiting substantially the same activity in humans and vice-versa.

There remains a lack of effective and safe alternatives for altering metabolism and treatment of metabolic diseases, such as obesity, diabetes and cachexia. There is therefore a need for new formulations for such uses.

SUMMARY OF THE INVENTION

The present invention is based in part on the finding that Zinc-α$_2$-glycoprotein has an effect on body weight and insulin responsiveness in adult obese hyperglycemic (ob/ob) mice and mature Wistar rats, and that anti-ZAG antibodies prevent weight loss in cachexia situations. Such a finding is useful in methods for moderating body weight, improving insulin responsiveness or ameliorating the symptoms associated with cachexia or diseases associated with muscle wasting.

In one embodiment the present invention provides a formulation comprising a zinc-α$_2$-glycoprotein (ZAG), a ZAG variant, a modified ZAG, or a functional fragment thereof. In one aspect, the ZAG is mammalian, e.g., human, and may include the amino acid sequence set forth in SEQ ID NO: 1. The ZAG peptide may conjugated to a non-protein polymer. The ZAG peptide may be sialylated, PEGylated or modified to increase solubility or stability. The ZAG peptide may be recombinant or synthetic. In various aspects, the ZAG peptide may be modified ZAG and include the wild-type ZAG amino acid sequence with one or more mutations to the amino acid sequence selected from deletions, additions or conservative substitutions. In various aspects, the ZAG peptide may include one or more of a leader sequence and a trailing sequence. The ZAG peptide may also be glycosylated, e.g., as a result of a posttranslational modification. Additionally, in various embodiments the formulation may further include a pharmaceutically acceptable carrier. The formulation may also include one or more agents including a β3 agonist and β-adrenergic receptor (β-AR) antagonist, such as a β2-adrenergic receptor (β2-AR) antagonist, a β1-adrenergic receptor (β1-AR) antagonist, and a β3-adrenergic receptor (β3-AR) antagonist. In some aspects, the formulation of claim 1 may further include a glucagon-like peptide-1 (GLP-1) or an analog thereof.

In another embodiment, the invention provides a foodstuff additive or nutritional supplement including the formulation of the invention as described herein.

In another embodiment, the invention provides a method for delivering a formulation to a mammalian subject, the method including administering to the mammalian subject the formulation as described herein.

In another embodiment, the invention provides a method for delivering a zinc-α$_2$-glycoprotein (ZAG) to a mammalian subject, the method including delivering to the subject by oral administration the formulation as described herein.

In another embodiment, the invention provides a method for orally delivering a zinc-α$_2$-glycoprotein (ZAG) to a mammalian subject in mega doses similar to that of mega dosed oral insulin requiring systemic absorption of administered ZAG as described herein.

In another embodiment, the invention provides a method for orally delivering a zinc-α$_2$-glycoprotein (ZAG) to a mammalian subject in surprisingly effective low doses similar to that of intravenous administration of ZAG and in formulations surprisingly not requiring systemic absorption of administered ZAG as described herein.

In another embodiment, the invention provides a method for increasing a subject's endogenous level of a zinc-α$_2$-glycoprotein (ZAG), the method including administering to the subject the formulation as described herein.

The present invention further provides a method of ameliorating symptoms of cachexia in a subject. The method includes administering to the subject in need of such treatment a therapeutically effective dosage of an inhibitor of the biological activity of a polypeptide having the sequence as shown in SEQ ID NO: 1, resulting in an amelioration of symptoms associated with cachexia following treatment. In one embodiment, the inhibitor is a monoclonal antibody that binds a polypeptide that comprises a sequence at least 80% homologous to the polypeptide having the sequence as shown in SEQ ID NO: 1. In another embodiment, the treatment includes daily administration for 10 days. In another embodiment, the inhibitor is administered daily, every other day, every 2 days, or every 3 days, for up to 10 days or longer. In another embodiment, the antibody is administered twice daily. The antibody may be administered intravenously, subcutaneously, sublingually, intranasally, orally, or via inhalation. In another embodiment, the inhibitor is administered in combination with one or more agents selected from the group consisting of a β3-adrenergic receptor (β3-AR) antagonist. In one embodiment, the β3-AR antagonist is SR59230A. In another embodiment, the antibody is glycosylated. In another embodiment, the agent that inhibits the homologous polypeptide is a non-antibody agent, for example but not limited to, an aptamer.

In another aspect, the present invention provides a method of treating a subject to bring about reduction in weight loss. The method includes administering to the subject in need of such treatment a therapeutically effective dosage of an inhibitor of the polypeptide having the sequence as shown in SEQ ID NO: 1 in combination with one or more agents selected from the group consisting of a β3-adrenergic receptor (β3-AR) antagonist. In one embodiment, the inhibitor is a monoclonal antibody that binds a polypeptide that comprises a sequence at least 80% homologous to the polypeptide having the sequence as shown in SEQ ID NO: 1. In another embodiment, the β3-AR antagonist is SR59230A. In another embodiment, the antibody is glycosylated. In another embodiment, the agent that inhibits the homologous polypeptide is a non-antibody agent, for example but not limited to, an aptamer.

In another aspect, the present invention provides a pharmaceutical composition comprising an antibody, or functional fragment thereof, that binds the polypeptide having the sequence as shown in SEQ ID NO: 1 and an agent selected from the group consisting of a β3-adrenergic receptor (β3-AR) antagonist and a β3 antagonist. In one embodiment, the β3-AR antagonist is SR59230A. In another embodiment, the antibody is glycosylated.

This disclosure provides materials and methods for supplementing a human or animal diet. In one aspect, the instant disclosure provides nutritional supplement formulations. A nutritional supplement formulation of the invention can include zinc-α2-glycoprotein (ZAG) or a functional fragment thereof. The disclosure also provides materials such as kits that include one or more nutritional supplement formulations, such as nutritional supplement formulations that include ZAG or functional fragments thereof. In another aspect, the disclosure provides a method of delivery of an orally administered therapeutic agent, including administering a β3 agonist in combination with the orally administered therapeutic agent.

The formulations, kits, and methods herein can be useful for improving a human's health and/or to promote weight loss, or independent of weight loss, improve insulin resistance and reduce hyperglycemia. These formulations, kits and methods may therefore find use in the treatment of diseases associated with obesity and/or hyperglycemia.

In another aspect, the invention provides a food stuff that includes the formulation of the invention in combination with a consumable carrier. Exemplary consumable carriers include, but are not limited to cookies, brownies, crackers, breakfast bars, energy bars, cereals, cakes, breads, beverages, meat products, and meat substitute products.

In another aspect, the invention provides a method of supplementing a human diet. The method includes ingesting formulation that includes zinc-$\alpha_2$-glycoprotein (ZAG) or a functional fragment thereof. In one embodiment, the ZAG is mammalian, such as the human ZAG polypeptide having the sequence as shown in SEQ ID NO: 1, or a fragment thereof. The method may be performed daily for 10 days. In another embodiment, the formulation is ingested daily, every other day, every 2 days, or every 3 days, for up to 10 days or longer. In another embodiment, the formulation is ingested twice daily. In another embodiment, the formulation is ingested in combination with one or more agents selected from the group consisting of a β3-adrenergic receptor (β3-AR) agonist and a βAR agonist and a β3-AR antagonist. In one embodiment, the β3-AR antagonist is SR59230A. In another embodiment, β3-AR agonist is AMNI-BRL37344 (BRL37344). In another embodiment, the formulation is ingested or delivered in combination with one or more agents used to improve glycemic control whether sequentially in any order or in parallel. In one embodiment, the glycemic control agent is insulin or any derivative or analog thereof. In another embodiment, the glycemic control agent is a glucagon-like peptide-1 (GLP-1) or any derivative or analog thereof.

In another aspect, the invention provides a method of delivery of an orally administered therapeutic agent, wherein the therapeutic agent is delivered in combination with a β3 agonist. In another embodiment, the β3 agonist and the therapeutic agent are delivered simultaneously. In yet another embodiment, the β3 agonist is administered prior to or following administration of the therapeutic agent. In certain embodiments, the therapeutic agent is ZAG. In other embodiments, the therapeutic agent includes atrial natriuretic peptides, brain natriuretic peptides, platelet aggregation inhibitors, streptokinase, heparin, urokinase, renin inhibitors, insulin, antibiotics, and sleep inducing peptide.

In a further aspect, the present invention provides a method of treating a subject to bring about a weight reduction or reduction in obesity. The method includes administering to the subject in need of such treatment a nutritional supplement formulation that includes a therapeutically effective dosage of a polypeptide having the sequence as shown in SEQ ID NO: 1 or a fragment thereof.

In another embodiment, the invention provides a method of monitoring zinc-$\alpha_2$-glycoprotein (ZAG) activity in a mammalian subject. The method includes: a) orally administering the subject the formulation of the invention; and b) detecting the level of ZAG activity; thereby monitoring ZAG activity in the subject.

BRIEF DESCRIPTION OF THE DRAWINGS

FIG. 10 is a pictorial diagram showing the complete amino acid sequence (SEQ ID NO: 1) of the human plasma Zn-$\alpha_2$-glycoprotein, as published by T. Araki et al. (1988) "Complete amino acid sequence of human plasma Zn-$\alpha_2$-glycoprotein and its homology to histocompatibility antigens."

FIGS. 55A, 55B and 55C are pictorial diagrams showing expression of β3-AR after treatment of ob/ob mice with ZAG (35 µg; i.v. day$^{-1}$) for 5 days. Western blots showing expression of β3-AR in gastrocnemius muscle (54A), BAT (54B) and WAT (54C) of ob/ob mice treated with either PBS or ZAG. The densitometric analysis is the average of three separate Western blots. Differences from control as shown as c, $p<0.001$.

FIGS. 56A, 56B and 56C are pictorial diagrams of expression of β1- and β2-AR in gastrocnemius muscle (56A), WAT (56B) and heart (56C) after treatment of ob/ob mice with ZAG (35 µg; i.v., daily) for 5 days. Differences from PBS treated animals is shown as a, $p<0.05$. FIGS. 57A, 57B, 57C and 57D are pictorial diagrams of the effect of ZAG on expression of uncoupling proteins. Western blots showing expression of UCP1 showing expression of UCP1 in BAT (57A) and WAT (57B), and expression of UCP3 in WAT (57C) and AMPK in gastrocnemius muscle (57D) in ob/ob mice after treatment with either PBS or ZAG (35 µg; i.v., daily) for 5 days. The densitometric analysis is the average of three separate blots. Differences from PBS treated animals are shown as c, $p<0.001$.

DETAILED DESCRIPTION OF THE INVENTION

Figure 1A:
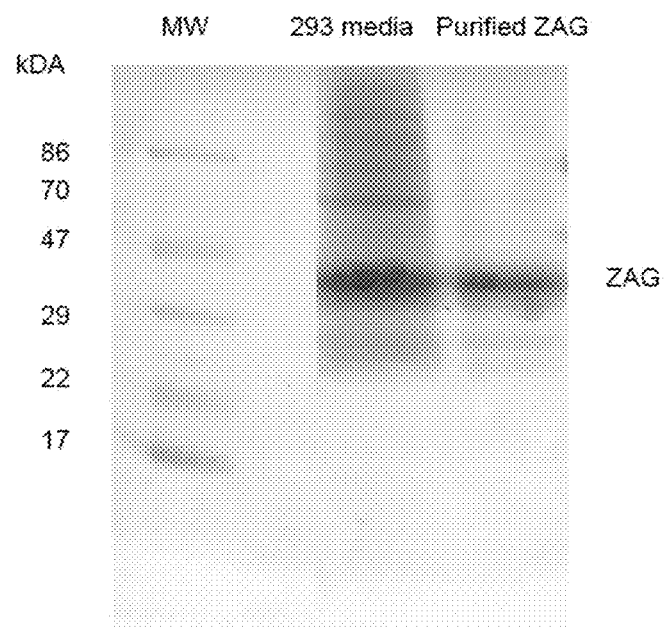
FIG. 1A is a pictorial diagram showing characterization of ZAG and its effect on lipolysis and body weight of ob/ob mice. Coomassie staining after 12% SDS-PAGE showing total proteins in 293 cell media and ZAG purified as described.

The present invention is based on the observation that anti-human Zinc-$\alpha_2$-glycoprotein (ZAG) antibodies reduce weight loss in models of cachexia. As such, the invention provides methods for preventing weight loss in cachexia situations in a subject. Also provided are combinatorial treatments to bring about a reduction in weight loss in a subject with cachexia.

Provided herein are formulations and methods for treating mammals and/or supplementing a human or animal diet. The methods can include ingesting one or more of the described formulations for certain time periods and/or in a certain order. Kits comprising one or more of the formulations are also provided. As such, the present invention is based on the observation that recombinant zinc-α2-glycoprotein (ZAG) produces a decrease in body weight and increase in insulin responsiveness in subjects with no effect on food intake.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The complete amino acid sequence of ZAG has been reported in a paper entitled "Complete amino acid sequence of human plasma Zinc-$\alpha_2$-glycoprotein and its homology to histocompatibility antigens" by T. Araki et al. (1988) Proc. Natl. Acad. Sci. USA., 85, 679-683, wherein the glycoprotein was shown as consisting of a single polypeptide chain of 276 amino acid residues having three distinct domain structures (A, B and C) and including two disulfide bonds together with N-linked glycans at three glycosylation sites. This amino acid sequence of the polypeptide component is set out in FIG. 10 of the accompanying drawings. Although some subsequent publications have indicated that the composition of human ZAG can vary somewhat when isolated from different body fluids or tissues, all preparations of this material have substantially the same immunological characteristics. As reported by H. Ueyama, et al. (1991) "Cloning and nucleotide sequence of a human Zinc-$\alpha_2$-glycoprotein cDNA and chromosomal assignment of its gene", Biochem. Biophys. Res. Commun. 177, 696-703, cDNA of ZAG has been isolated from human liver and prostate gland libraries, and also the gene has been isolated, as reported by Ueyama et al., (1993) "Molecular cloning and chromosomal assignment of the gene for human Zinc-$\alpha_2$-glycoprotein", Biochemistry 32, 12968-12976. H. Ueyama et al. have also described, in J. Biochem. (1994) 116, 677-681, studies on ZAG cDNAs from rat and mouse liver which, together with the glycoprotein expressed by the corresponding mRNAs, have been sequenced and compared with the human material. Although detail differences were found as would be expected from different species, a high degree of amino acid sequence homology was found with over 50% identity with the human counterpart (over 70% identity within domain B of the glycoprotein). Again, common immunological properties between the human, rat and mouse ZAG have been observed.

The purified ZAG discussed above was prepared from fresh human plasma substantially according to the method described by Ohkubo et al. (Ohkubo et al. (1988) "Purification and characterisation of human plasma Zn-$\alpha_2$-glycoprotein" Prep. Biochem., 18, 413-430). It will be appreciated that in some cases fragments of the isolated lipid mobilizing factor, of ZAG, or of anti-ZAG antibodies may be produced without loss of activity, and various additions, deletions or substitutions may be made which also will not substantially affect this activity. As such, the methods of the invention also include use of functional fragments of anti-ZAG antibodies. The antibody or fragment thereof used in these therapeutic applications may further be produced by recombinant DNA techniques such as are well known in the art based possibly on the known cDNA sequence for Zn-$\alpha_2$-glycoprotein which has been published for example in H. Ueyama et al. (1994) "Structure and Expression of Rat and Mouse mRNAs for Zn-$\alpha_2$-glycoprotein" J. Biochem., 116, 677-681. In addition, the antibody or fragment thereof used in these therapeutic applications may further include post-expression modifications of the polypeptide, for example, glycosylations, acetylations, phosphorylations and the like, as well as other modifications known in the art, both naturally occurring and non-naturally occurring.

As used herein, ZAG polypeptides or proteins include variants of wild type proteins which retain their biological function. As such, one or more of the residues of a ZAG protein can be altered to yield a variant or truncated protein, so long as the variant retains it native biological activity. Conservative amino acid substitutions include, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. However, the invention also envisions variants with non-conservative substitutions.

The term "peptide", "polypeptide" and "protein" are used interchangeably herein unless otherwise distinguished to refer to polymers of amino acids of any length. These terms also include proteins that are post-translationally modified through reactions that include glycosylation, acetylation and phosphorylation.

As discussed above, the present invention includes use of a function fragment of a ZAG polypeptide or protein. A functional fragment, is characterized, in part, by having or affecting an activity associated with weight loss, lowering blood glucose level, increasing body temperature, improving glucose tissue uptake, increasing expression of Bet3 receptors, increasing expression of ZAG, increasing expression of Glut 4, and/or increasing expression of UCP 1 and UCP 3. Thus, the term "functional fragment," when used herein refers to a polypeptide that retains one or more biological functions of ZAG Methods for identifying such a functional fragment of a ZAG polypeptide, are generally known in the art.

As used herein, the term "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., Immunology, 3.sup.rd Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547, Pack and Pluckthun (1992) Biochemistry 31:1579, Hollinger et al., 1993, supra, Gruber et al. (1994) J Immunol: 5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

An antibody immunologically reactive with a particular antigen can be generated by recombinant methods such as selection of libraries of recombinant antibodies in phage or similar vectors, see, e.g., Huse et al., Science 246:1275-1281 (1989); Ward et al., Nature 341:544-546 (1989); and Vaughan et al., Nature Biotech. 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "$V_H$" refer to the variable region of an immunoglobulin heavy chain of an antibody, including the heavy chain of an Fv, scFv, or Fab. References to "$V_L$" or a "$V_L$" refer to the variable region of an immunoglobulin light chain, including the light chain of an Fv, scFv, dsFv or Fab.

An antibody having a constant region substantially identical to a naturally occurring class IgG antibody constant region refers to an antibody in which any constant region present is substantially identical, i.e., at least about 85-90%, and preferably at least 95% identical, to the amino acid sequence of the naturally occurring class IgG antibody's constant region.

As used herein, the term "monoclonal antibody" is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies useful with the present invention may be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow and Lane, "Antibodies: A Laboratory Manual," Cold Spring Harbor Laboratory Press, New York (1988); Hammerling et al., in: "Monoclonal Antibodies and T-Cell Hybridomas," Elsevier, N.Y. (1981), pp. 563-681 (both of which are incorporated herein by reference in their entireties).

Thus, in some embodiments, the antibodies of the invention may be chimeric, primatized, humanized, or human antibodies.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Methods for producing chimeric antibodies are known in the art. See e.g., Morrison, Science 229:1202-1207 (1985); Oi et al., BioTechniques 4:214-221 (1986); Gillies et al., J. Immunol. Methods 125:191-202 (1989); U.S. Pat. Nos. 5,807,715; 4,816,567; and 4,816,397, which are incorporated herein by reference in their entireties.

The term "humanized antibody" or "humanized immunoglobulin" refers to an immunoglobulin comprising a human framework, at least one and preferably all complementarity determining regions (CDRs) from a non-human antibody, and in which any constant region present is substantially identical to a human immunoglobulin constant region, i.e., at least about 85-90%, and preferably at least 95% identical. Hence, all parts of a humanized immunoglobulin, except possibly the CDRs, are substantially identical to corresponding parts of one or more native human immunoglobulin sequences. Accordingly, such humanized antibodies are chimeric antibodies (U.S. Pat. No. 4,816,567), wherein substantially less than an intact human variable domain has been substituted by the corresponding sequence from a non-human species. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., U.S. Pat. Nos. 5,530,101; 5,585,089; 5,693,761; 5,693,762; 6,180,370 (each of which is incorporated by reference in its entirety). Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, Mol. Immunol., 28:489-498 (1991); Studnicka et al., Prot. Eng. 7:805-814 (1994); Roguska et al., Proc. Natl. Acad. Sci. 91:969-973 (1994), and chain shuffling (U.S. Pat. No. 5,565,332), all of which are hereby incorporated by reference in their entireties.

In certain embodiments, completely "human" antibodies may be desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins, but which can express human immunoglobulin genes. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Abgenix, Inc. (Fremont, Calif.) and Medarex (Princeton, N.J.) can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., Biotechnology 12:899-903 (1988).

The term "primatized antibody" refers to an antibody comprising monkey variable regions and human constant regions. Methods for producing primatized antibodies are known in the art. See e.g., U.S. Pat. Nos. 5,658,570; 5,681,722; and 5,693,780, which are incorporated herein by reference in their entireties.

As used herein, the terms "epitope" or "antigenic determinant" refer to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

Antibodies of "IgG class" refers to antibodies of IgG1, IgG2, IgG3, and IgG4. The numbering of the amino acid residues in the heavy and light chains is that of the EU index (Kabat, et al., "Sequences of Proteins of Immunological Interest", 5th ed., National Institutes of Health, Bethesda, Md. (1991); the EU numbering scheme is used herein).

Methods of preparing polyclonal antibodies are known to the skilled artisan. Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein, such as the polypeptide shown in SEQ ID NO: 1, encoded by a nucleic acid or a functional fragment thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler & Milstein, Nature 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a polypeptide as shown in SEQ ID NO: 1 or a functional fragment thereof.

Human antibodies can be produced using various techniques known in the art, including phage display libraries (Hoogenboom & Winter, J. Mol. Biol. 227:381 (1991); Marks et al., J. Mol. Biol. 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., J. Immunol. 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., Bio/Technology 10:779-783 (1992); Lonberg et al., Nature 368: 856-859 (1994); Morrison, Nature 368:812-13 (1994); Fishwild et al., Nature Biotechnology 14:845-51 (1996); Neuberger, Nature Biotechnology 14:826 (1996); Lonberg & Huszar, Intern. Rev. Immunol. 13:65-93 (1995).

In some embodiments, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston et al., Proc. Nat'l Acad. Sci. USA 8:5879 (1988); Bird et al., Science 242:4236 (1988); Glockshuber et al., Biochemistry 29:1362 (1990); U.S. Pat. Nos. 4,946,778, 5,132,405 and Stemmer et al., Biotechniques 14:256-265 (1993). Generally the peptide linker will have no specific biological activity other than to join the regions or to preserve some minimum distance or other spatial relationship between the $V_H$ and $V_L$. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser (SEQ ID NO: 7), preferably 2, 3, 4, 5, or 6 such sequences. However, it is to be appreciated that some amino acid substitutions within the linker can be made. For example, a valine can be substituted for a glycine.

Methods of making scFv antibodies have been described. See, Huse et al., supra; Ward et al. supra; and Vaughan et al., supra. In brief, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell. The scFv that specifically bind to the desired antigen are typically found by panning of a phage display library. Panning can be performed by any of several methods. Panning can conveniently be performed using cells expressing the desired antigen on their surface or using a solid surface coated with the desired antigen. Conveniently, the surface can be a magnetic bead. The unbound phage are washed off the solid surface and the bound phage are eluted.

ZAG and/or fragments thereof has been previously shown to bring about a weight reduction or reduction in obesity in mammals, as disclosed in U.S. Pat. Nos. 6,890,899 and 7,550,429, and in U.S. Pub. No. 2010/0173829, the entire contents of each of which is incorporated herein by reference. In one embodiment, the present invention demonstrates that anti-ZAG antibodies and/or functional fragments thereof reduces weight loss in models of cachexia. It is therefore contemplated that the methods of the instant invention provide a detectable effect on symptoms associated with cachexia and/or diseases associated with muscle wasting disease.

Accordingly, in one aspect, the invention provides a method of ameliorating the symptoms of cachexia in a subject. The method includes administering to the subject in need of such treatment a therapeutically effective dosage of an inhibitor of the biological activity of a polypeptide having the sequence as shown in SEQ ID NO: 1. In one embodiment, the treatment regimen may be for months (e.g., 1, 2, 3, 4, 5, 6, 7, 8, 9, 10, 11, or 12 months), or years. In another embodiment, the polypeptide is administered for a period of up to 21 days or longer. In another embodiment, the amelioration of symptoms is detectable within days (e.g., 1, 2, 3, 4, 5, 6, or 7 days), weeks (e.g., 1, 2, 3, or 4 weeks), or months (e.g., 1, 2, 3, 4, 5, 6, 7, 8, 9, 10, 11, or 12 months) of initiating treatment. In another embodiment, the treatment regimen is about 10 days wherein there is amelioration of symptoms associated with cachexia following treatment. In another embodiment, the treatment regimen is about 21 days wherein there is amelioration of symptoms associated with cachexia following treatment.

In addition, it has been observed that a lipid mobilizing agent having similar characteristics of ZAG and/or fragments thereof has also been used to bring about a weight reduction or reduction in obesity in mammals, as disclosed in U.S. Published App. No. 2006/0160723, incorporated by herein by reference in its entirety. Finally, it has been shown that ZAG and/or functional fragments thereof increases the insulin responsiveness of adipocytes and skeletal muscle, and produces an increase in muscle mass through an increase in protein synthesis coupled with a decrease in protein degradation regardless of whether a weight reduction or reduction in obesity is observed during treatment (see U.S. Ser. No. 12/614,289, incorporated herein by reference).

Additionally, β3 agonists are reportedly effective insulin sensitizing agents in rodents and their potential to reduce blood glucose levels in humans has been a subject of investigation. Activation of β3 agonists adrenoceptors stimulates fat oxidation, thereby lowering intracellular concentrations of metabolites including fatty acyl CoA and diacylglycerol, which modulate insulin signaling. Furthermore, it is contemplated herein that certain β3 receptor agonists may not have found success in clinical trials given that one category of β3 receptors available to these agents is located in the digestive system and particularly in the mouth, pharynx, esophagus and stomach, resulting in minimal, if any, exposure of the agonist to most of these receptors. This theory is supported by the observation that several of the β3 agonist therapeutic agents were found to be efficacious but had limited bioavailability in the plasma space.

A number of formulations are provided herein. A formulation can be in any form, e.g., liquid, solid, gel, emulsion, powder, tablet, capsule, or gel cap (e.g., soft or hard gel cap). A formulation typically will include one or more compositions that have been purified, isolated, or extracted (e.g., from plants) or synthesized, which are combined to provide a benefit (e.g., a health benefit in addition to a nutritional benefit) when used to supplement food in a diet.

In certain embodiments, recommended amounts per day or per serving of a formulation or of ingredients provided in a formulation may be set forth herein. In certain cases, as will be recognized by one having ordinary skill in the art, one could vary the form of the formulation, e.g., by substituting a powder for a capsule, a tablet for a capsule, a gel-cap for a tablet, a gel-cap for a capsule, a powder for a gel-cap, or any such combination, in order to provide such recommended amounts per day or per serving of a formulation.

Any of the formulations can be prepared using well known methods by those having ordinary skill in the art, e.g., by mixing the recited ingredients in the proper amounts. Ingredients for inclusion in a formulation are generally commercially available.

Accordingly, in one aspect, the invention provides a formulation that includes ZAG or a functional fragment thereof. For example, the ZAG may be mammalian ZAG, such human ZAG as shown in SEQ ID NO: 1, or fragments thereof. However, it should be understood that the ZAG may be derived from any source provided that the ZAG retains the activity of wild-type ZAG. In one embodiment, the further includes a pharmaceutically acceptable carrier, which constitutes one or more accessory ingredients.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Cachexia is commonly associated with a number of disease states, including acute inflammatory processes associated with critical illness and chronic inflammatory diseases, cancer, AIDS, sepsis, COPD, renal failure, arthritis, congestive heart failure, muscular dystrophy, diabetes, sarcopenia of aging, severe trauma (e.g., orthopedic immobilization of a limb), metabolic acidosis, denervation atrophy, and weightlessness.

The term "therapeutically effective amount" or "effective amount" means the amount of a compound or pharmaceutical composition that will elicit the biological or medical response of a tissue, system, animal or human that is being sought by the researcher, veterinarian, medical doctor or other clinician.

In some embodiments, the formulations of the invention are intended to be orally administered daily. However, other forms of administration are equally envisioned. As used herein, the terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually orally or by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration. As such, in one embodiment, the anti-ZAG antibodies, fragments thereof, and/or formulations of the invention are administered to a subject via inhalation, intranasally, buccally, sublingually, intravenously, intramuscularly, and/or orally. In another embodiment, the antibodies or compositions thereof are formulated in rapid-melting compositions, extended release compositions, and the like.

As used herein, the term "ameliorating" or "treating" means that the clinical signs and/or the symptoms associated with cachexia are lessened as a result of the actions performed. The signs or symptoms to be monitored will be characteristic of cachexia and will be well known to the skilled clinician, as will the methods for monitoring the signs and conditions. In addition to adipose/muscle mass loss, exemplary symptoms associated with cachexia include, but are not limited to, fever, headache, chronic pain, body malaise, fainting, seizure associated with the fever, shock, palpitations, heart murmur, gangrene, epistaxis, hemoptysis, cough, difficulty in breathing, wheezing, hyperventilation and hypoventilation, mouth breathing, hiccup and chest pain, abdominal pain, nausea or vomiting, heartburn, halitosis, and flatulence, as compared to a normal subject or a subject that does not have cachexia. As such, an amelioration of the symptoms associate with cachexia includes but is not limited to, decreasing or reducing weight loss in the subject and reversing one or more of the above-listed symptoms.

As used herein, the terms "reduce" and "inhibit" are used together because it is recognized that, in some cases, a decrease can be reduced below the level of detection of a particular assay. As such, it may not always be clear whether the expression level or activity is "reduced" below a level of detection of an assay, or is completely "inhibited." Nevertheless, it will be clearly determinable, following a treatment according to the present methods, that amount of weight loss in a subject is at least reduced from the level prior to treatment.

ZAG has been attributed a number of biological roles, but its role as an adipokine regulating lipid mobilization and utilization is most important in regulating body composition. Previous studies suggested that the increase in protein synthesis was due to an increase in cyclic AMP through interaction with the β-adrenoreceptor, while the decrease in protein degradation was due to reduced activity of the ubiquitin-proteasome proteolytic pathway. Studies in db/db mice show that insulin resistance causes muscle wasting through an increased activity of the ubiquitin-proteasome pathway. An increased phosphorylation of both PKR and eIF2α will reduce protein synthesis by blocking translation initiation, while activation of PKR will increase protein degradation through activation of nuclear factor-κB (NF-κB), increasing expression of proteasome subunits. In vitro studies using myotubes in the presence of high extracellular glucose showed that activation of PKR led to activation of p38MAPK and formation of reactive oxygen species (ROS). p38MAPK can phosphorylate and activate cPLA2 at Ser-505 causing release of arachidonic acid, a source of ROS. Hyperactivation of p38MAPK in skeletal muscle has been observed in models of diet-induced obesity. In addition caspase-3 activity has been shown to be increased in skeletal muscle of diabetic animals, which may be part of the signaling cascade, since it can cleave PKR leading to activation. Without being bound to theory, the ability of ZAG to attenuate these signaling pathways provides an explanation regarding its ability to increase muscle mass. As such, an anti-ZAG antibody is demonstrated to decrease loss of muscle mass in cachexia situations.

Accordingly, in another aspect, the invention provides a method of supplementing a human or animal diet. The method includes administering to the subject a ZAG polypeptide or a fragment thereof. In another embodiment, the method includes ingesting a formulation that includes a ZAG polypeptide, such as the human ZAG polypeptide as set forth in SEQ ID NO: 1. A formulation can be ingested alone or in combination with any other known formulation, in any order and for varying relative lengths of time. In certain embodiments, certain formulations are used prior to other formulations, while other formulations are ingested concurrently.

Thus, ZAG is identified as a lipid mobilizing factor capable of inducing lipolysis in white adipocytes of the mouse in a GTP-dependent process, similar to that induced by lipolytic hormones. The data presented herein supports these findings by showing that ZAG has a similar lipolytic effect in rat adipocytes, and, moreover, produces a decrease in body weight and carcass fat in mature male rats, despite the fact that the sequence homology between rat and human ZAG is only 59.4%.

ZAG also counters some of the metabolic features of the diabetic state including a reduction of plasma insulin levels and improved response in the glucose tolerance test. Thus, in another aspect, the invention provides a method of decreasing plasma insulin levels in a subject. The method includes administering to the subject a therapeutically effective dosage of a polypeptide having the sequence as shown in SEQ ID NO: 1 or a fragment thereof. In one embodiment, the decrease in plasma insulin occurs within 3 days of initiating treatment. In another embodiment, the treatment regimen is administered for 10 days or longer. In another embodiment, the treatment regimen is administered for 21 days or longer.

In addition, ZAG has been shown to increase glucose oxidation and increase the tissue glucose metabolic rate in adult male mice. This increased utilization of glucose would explain the fall in both blood glucose and insulin levels in ob/ob mice administered ZAG. Triglyceride utilization was also increased in mice administered ZAG, which would explain the fall in plasma non-esterified fatty acids (NEFA) and triglycerides (TG) despite the increase in plasma glycerol, indicative of increased lipolysis. The increased utilization of lipid would be anticipated from the increased expression of UCP1 and UCP3 in BAT and UCP3 in skeletal muscle, resulting in an increase in body temperature. Thus, ZAG is identified as a lipid mobilizing factor capable of inducing lipolysis in white adipocytes of the mouse in a GTP-dependent process, similar to that induced by lipolytic hormones. As such, in one embodiment, amelioration of the symptoms associated with hyperglycemia also includes an increase in body temperature of about 0.5° C. to about 1° C. during treatment. In one embodiment, the increase in body temperature occurs within 4 days of initiating treatment. In another embodiment, amelioration of the symptoms associated with hyperglycemia also includes an increase in pancreatic insulin as compared to pancreatic insulin levels prior to treatment, since less insulin is needed to control blood glucose as a result of the presence of ZAG.

ZAG has also been shown to counter some of the metabolic features of the diabetic state including a reduction of plasma insulin levels and improved response in the glucose tolerance test. In addition ZAG increases the responsiveness of epididymal adipocytes to the lipolytic effect of a β3-adrenergic stimulant. ZAG also increases the expression of HSL and ATGL in epididymal adipose tissue which have been found to be reduced in the obese insulin-resistant state. Factors regulating the expression of HSL and ATGL are not known. However, the specific ERK inhibitor, PD98059 downregulated HSL expression in response to ZAG, suggesting a role for MAPK in this process. Mice lacking MAPK phosphatase-1 have increase activities of ERK and p38MAPK in WAT, and are resistant to diet-induced obesity due to enhanced energy expenditure. Previous studies have suggested a role for MAPK in the ZAG-induced expression of UCP3 in skeletal muscle. ERK activation may regulate lipolysis in adipocytes by phosphorylation of serine residues of HSL, such as Ser-600, one of the sites phosphorylated by protein kinase A.

The results presented herein show that ZAG administration to the rat also increases the expression of ATGL and HSL in the rat. ATGL may be important in excess fat storage in obesity, since ATGL knockout mice have large fat deposits and reduced NEFA release from WAT in response to isoproterenol, although they did display normal insulin sensitivity. In contrast HSL null mice, when fed a normal diet, had body weights similar to wild-type animals. However, expression of both ATGL and HSL are reduced in human WAT in the obese insulin-resistant state compared with the insulin sensitive state, and weight reduction also decreased mRNA and protein levels.

Figure 24:
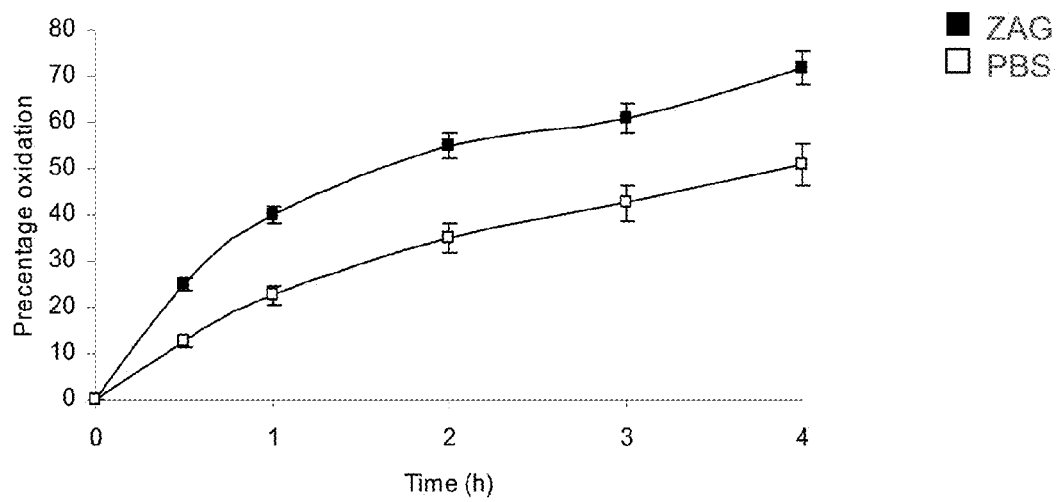
FIG. 24 is a graphical diagram showing the oxidation of D-[U-$^{14}$C glucose] to $^{14}CO_2$ in ob/ob mice.
Figure 25:
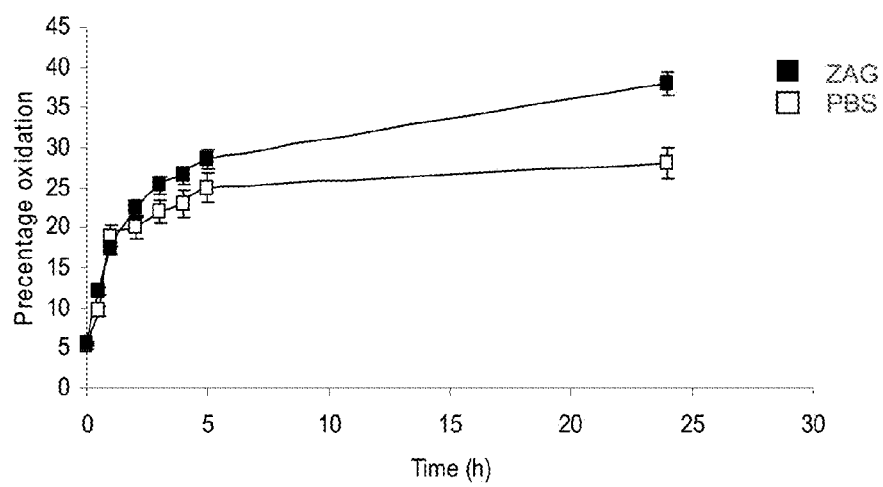
FIG. 25 is a graphical diagram showing production of $^{14}CO_2$ from [$^{14}$C carboxy] triolein in ob/ob mice.
Figure 26:
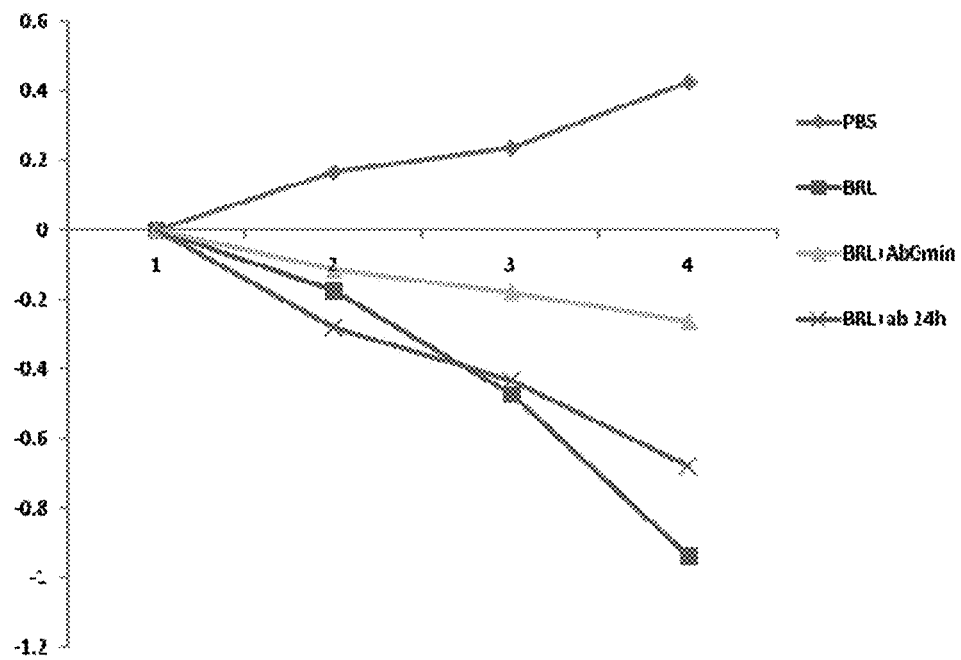
FIG. 26 is a graphical diagram showing reduction in weight loss in mice administered anti-ZAG, as compared to mice administered BRL37344 (cachexia model).
Figure 27:
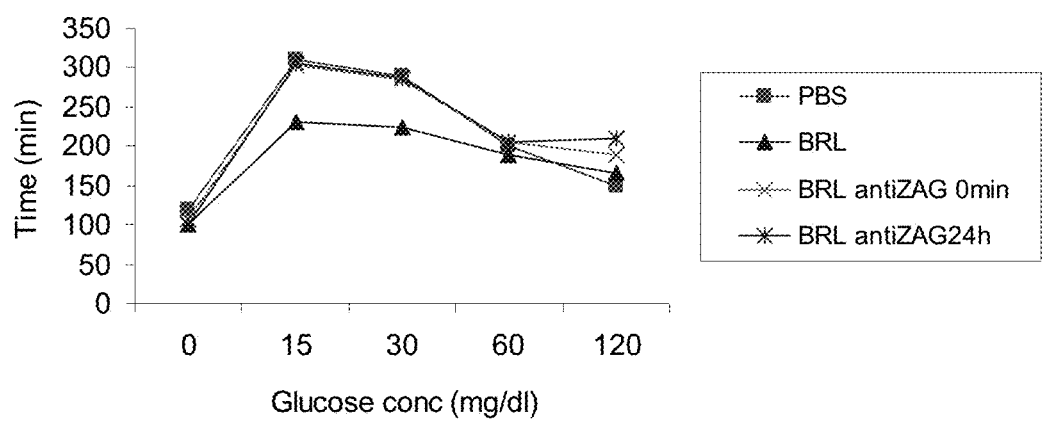
FIG. 27 is a graphical diagram showing glucose tolerance in ob/ob mice treated with the β3 agonist, BRL37344 in the absence and presence of an anti-ZAG antibody.
Figure 28:
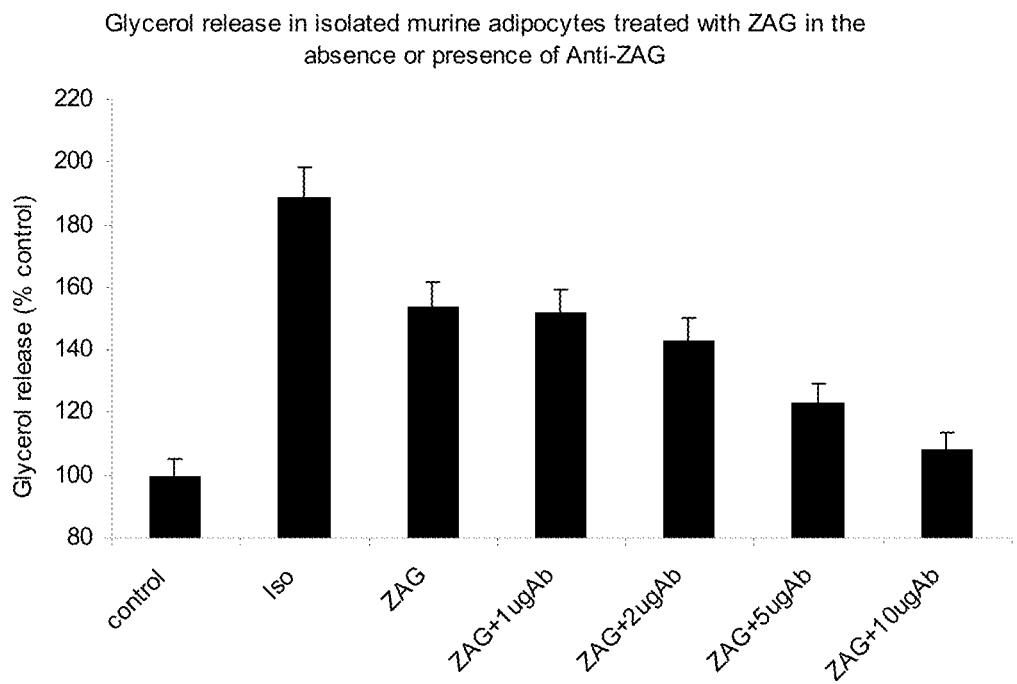
FIG. 28 is a graphical diagram showing the results of lipolysis in epididymal murine adipocytes in response to isoprenaline (Iso), ZAG, and an anti-ZAG antibody.
Figure 29:
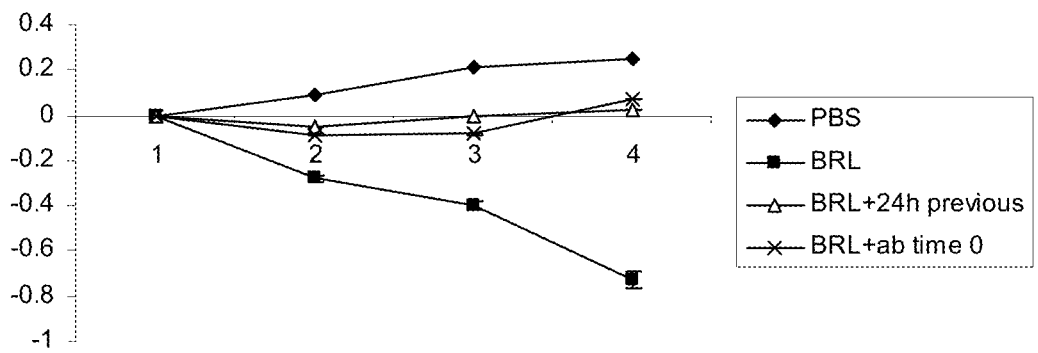
FIG. 29 is a graphical diagram showing weight change in ob/ob mice treated with BRL in the absence or presence of anti-ZAG where BRL was added either 24 h prior to anti-ZAG ab or at the same time.

Stimulation of lipolysis alone would not deplete body fat stores, since without an energy sink the liberated NEFA would be resynthesised back into triglycerides in adipocytes. To reduce body fat, ZAG not only increases lipolysis, as shown by an increase in plasma glycerol, but also increases lipid utilization, as shown by the decrease in plasma levels of triglycerides and NEFA. This energy is channeled into heat, as evidenced by the 0.4° C. rise in body temperature in rats treated with ZAG. The increased energy utilization most likely arises from the increased expression of UCP 1, which has been shown in both BAT and WAT after administration of ZAG. An increased expression of UCP1 would be expected to decrease plasma levels of NEFA, since they are the primary substrates for thermogenesis in BAT. BAT also has a high capacity for glucose utilization, which could partially explain the decrease in blood glucose. In addition there was increased expression of GLUT4 in skeletal muscle and WAT, which helps mediate the increase in glucose uptake in the presence of insulin. In mice treated with ZAG there was an increased glucose utilization/oxidation by brain, heart, BAT and gastrocnemius muscle, and increased production of $^{14}CO_2$ from D-[U-$^{14}$C] glucose, as well as [$^{14}$C carboxy] triolein (FIG. 24). There was also a three-fold increase in oxygen uptake by BAT of ob/ob mice after ZAG administration.

While ZAG increased expression of HSL in epididymal adipocytes there was no increase in either subcutaneous or visceral adipocytes. A similar situation was observed with expression of adipose triglyceride lipase (ATGL). Expression of HSL and ATGL correlated with expression of the active (phospho) form of ERK. Expression of HSL and ATGL in epididymal adipocytes correlated with an increased lipolytic response to the β3 agonist, BRL37344. This result suggests that ZAG may act synergistically with β3 agonists, and suggests that anti-ZAG antibodies may act synergistically with β3 antagonists.

As used herein, the term "agonist" refers to an agent or analog that is capable of inducing a full or partial pharmacological response. For example, an agonist may bind productively to a receptor and mimic the physiological reaction thereto. As used herein, the term "antagonist" refers to an agent or analog that does not provoke a biological response itself upon binding to a receptor, but blocks or dampens agonist-mediated responses. The methods and formulations of the invention may include administering anti-ZAG antibodies, or a functional fragment thereof, in combination with a β3 antagonist, such as but not limited to BRL37344, or a β3 agonist.

Examples of β3 agonists that may be used in the present invention include, but are not limited to: epinephrine (adrenaline), norepinephrine (noradrenaline), isoprotenerol, isoprenaline, propranolol, alprenolol, arotinolol, bucindolol, carazolol, carteolol, clenbuterol, denopamine, fenoterol, nadolol, octopamine, oxyprenolol, pindolol, [(cyano)pindolol], salbuterol, salmeterol, teratolol, tecradine, trimetoquinolol, 3'-iodotrimetoquinolol, 3',5'-iodotrimetoquinolol, Amibegron, Solabegron, Nebivolol, AD-9677, AJ-9677, AZ-002, CGP-12177, CL-316243, CL-317413, BRL-37344, BRL-35135, BRL-26830, BRL-28410, BRL-33725, BRL-37344, BRL-35113, BMS-194449, BMS-196085, BMS-201620, BMS-210285, BMS-187257, BMS-187413, the CONH2 substitution of SO3H of BMS-187413, the racemates of BMS-181413, CGP-20712A, CGP-12177, CP-114271, CP-331679, CP-331684, CP-209129, FR-165914, FR-149175, ICI-118551, ICI-201651, ICI-198157, ICI-D7114, LY-377604, LY-368842, KTO-7924, LY-362884, LY-750355, LY-749372, LY-79771, LY-104119, L-771047, L-755507, L-749372, L-750355, L-760087, L-766892, L-746646, L-757793, L-770644, L-760081, L-796568, L-748328, L-748337, Ro-16-8714, Ro-40-2148, (−)-RO-363, SB-215691, SB-220648, SB-226552, SB-229432, SB-251023, SB-236923, SB-246982, SR-58894A, SR-58611, SR-58878, SR-59062, SM-11044, SM-350300, ZD-7114, ZD-2079, ZD-9969, ZM-215001, and ZM-215967.

Examples of β-AR antagonists that may be used in the present invention include, but are not limited to: propranolol, (−)-propranolol, (+)-propranolol, practolol, (−)-practolol, (+)-practolol, CGP-20712A, ICI-118551, (−)-bupranolol, acebutolol, atenolol, betaxolol, bisoprolol, esmolol, nebivolol, metoprolol, acebutolol, carteolol, penbutolol, pindolol, carvedilol, labetalol, levobunolol, metipranolol, nadolol, sotalol, and timolol.

Induction of lipolysis in rat adipocytes by ZAG is suggested to be mediated through a β3-AR, and the effect of ZAG on adipose tissue and lean body mass may also be due to its ability to stimulate the β3-AR. Induction of UCP1 expression by ZAG has been shown to be mediated through interaction with a β3-AR. The increased expression of UCP1 in WAT may also be a β3-AR effect through remodeling of brown adipocyte precursors, as occurs with the β3-AR agonist CL316,243. Using knock-out mice the antiobesity effect of β3-AR stimulation has been mainly attributed to UCP1 in BAT, and less to UCP2 and UCP3 through the UCP1-dependent degradation of NEFA released from WAT. Glucose uptake into peripheral tissues of animals is stimulated by cold-exposure, an effect also mediated through the β3-AR. However, targeting the β3-AR has been more difficult in humans than in rodents, since β3-AR play a less prominent role than β1 and β2-AR subtypes in the control of lipolysis and nutritive blood flow in human subcutaneous abdominal adipose tissue. However, despite this the β3-AR agonist CL316,243 has been shown to increase fat oxidation in healthy young male volunteers. This may be due to the ability of β-adrenergic agonists to increase the number of β3-AR in plasma membranes from BAT.

Accordingly, in another aspect, the invention provides a method of treating a subject to bring about a reduction in weight loss due to cachexia or a disease associated with muscle wasting. The method includes administering to the subject in need of such treatment a therapeutically effective dosage of a β3 antagonist in combination with an antibody, or a fragment thereof, that binds to the polypeptide having the sequence as shown in SEQ ID NO: 1. In another embodiment, the method includes administering to the subject in need of such treatment a therapeutically effective dosage of a β3-AR antagonist in combination with an antibody, or a fragment thereof, that binds to the polypeptide having the sequence as shown in SEQ ID NO: 1.

Recent results suggest that ZAG expression in adipose tissue may be more important locally than circulating ZAG, by acting in a paracrine manner. Thus in humans, while mRNA levels of ZAG in visceral and subcutaneous fat correlated negatively with BMI, fat mass and insulin resistance, serum levels, determined by ELISA, correlated positively with parameters of adiposity (BMI and waist circumference) and insulin resistance. Thus the ability of ZAG to induce its own expression in gastrocnemius muscle, WAT and BAT may be critical for its ability to increase lipolysis and energy utilization.

In various embodiments of the invention, the purpose of combining ZAG, β-3AR agonists and β-AR antagonists varies depending on the purpose of the treatment and the status of the subject.

In one embodiment involving the treatment of obesity or diabetes in which it is desired to activate the β-3AR mechanism to achieve the desired lipolysis, glucose consumption, insulin sensitization, protein synthesis, increased energy expenditure, and the like. In this circumstance with some subjects it may be observed that the administered ZAG, or more likely the β-3AR agonist will exhibit some undesired activity at one or more of the β-1AR or the β-2AR, causing side effects or diminishment of desired efficacy. This circumstance would then call for the additional administration of β-AR antagonists, sometimes referred to as "classic beta blockers" so as to prevent the undesired activity at the β-1AR or β-2AR. These β-AR antagonists would preferably, but not necessarily, be selected to block the receptor subtype (one of β-1AR, β-2AR) that is associated with the side effect or mitigation of efficacy.

In another embodiment involving the treatment of cachexia. In cachexia caused by different diseases, and within populations of subjects with a given diseases, different degrees of cachexia are observed, and with different proportions of muscle loss and fat loss.

In another aspect, a cachectic subject may be suffering from loss of muscle mass, but with either no loss of fat, or some degree of fat loss. Because muscle loss is typically a more clinically undesireable outcome, utilizing ZAG to cause some of the muscle build-up that occurs in cachetic animals treated with ZAG, while also causing some degree of fat loss, may be desired. Thus treating such subjects with ZAG, a β-3AR agonist, and optionally as described above, β-AR antagonists, could increase muscle mass.

In another aspect, a cachectic subject may be suffering from loss of fat mass, with either no or some degree of loss of muscle mass. In this case, it may be desirable from a clinical standpoint to block the loss of fat, and so administration of antibodies specific to ZAG would be used, in order to block the action caused by ZAG and therefore decrease the downstream action of β-3AR.

In another embodiment, involving treatment of lipidystrophy, in which fat masses are disproportionate to the normal distribution within a subject, and in which loss of fat mass is desired. In this case, the administration of one or more of ZAG, a β-3AR agonist and a β-AR antagonist would be desired, with reasoning similar to the first circumstance.

All methods may further include the step of bringing the active ingredient(s) into association with a pharmaceutically acceptable carrier, which constitutes one or more accessory ingredients. As such, the invention also provides pharmaceutical compositions for use in treating subjects having symptoms associated with cachexia. In one embodiment, the composition includes as the active constituent a therapeutically effective amount of an anti-ZAG antibody as discussed above, or a functional fragment thereof, together with a pharmaceutically acceptable carrier, diluent of excipient.

Pharmaceutically acceptable carriers useful for formulating a composition for administration to a subject are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. In addition, such physiologically acceptable compounds may further be in salt form (i.e., balanced with a counter-ion such as Ca2+, Mg2+, Na+, NH4+, etc.), provided that the carrier is compatible with the desired route of administration (e.g., intravenous, subcutaneous, oral, etc.). One skilled in the art would know that the choice of a pharmaceutically acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second (or more) compound(s) such as a diagnostic reagent, additional nutritional substance, toxin, or therapeutic agent, for example, a cancer chemotherapeutic agent and/or vitamin(s).

Formulations of the present invention may also include one or more excipients. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; and glycine or other amino acids. Buffer systems for use with the formulations include citrate; acetate; bicarbonate; and phosphate buffers.

Formulations of the present invention suitable for oral administration may be presented as discrete units such as capsules, cachets, tablets or lozenges, each containing a predetermined amount of the active compound in the form of a powder or granules; or as a suspension of the active compound in an aqueous liquid or non-aqueous liquid such as a syrup, an elixir, an emulsion of a draught.

The nutritional supplement formulations can further include any number of additional ingredients that are known to promote health and/or weight reduction. Exemplary additional ingredients include, but are not limited to, low-glycemic ingredients such as carbohydrate sources, protein sources and sources of dietary fiber. Such low-glycemic ingredients have been shown to curb appetite and cause a reduction in daily caloric intake.

An important macronutrient of the nutritional supplement is carbohydrate because it has the greatest influence on satiety and subsequent weight loss. As used herein, satiety, refers to the sensation of fullness between one meal and the next and satiation refers to a sensation of fullness that develops during the progress of a meal and contributes to meal termination. Foods with low-glycemic-indexes evoke a smaller rise in blood glucose and insulin and a higher glucagon concentration, which promote satiety and prevent weight gain better than those carbohydrate-containing foods with higher ones because they take longer to digest and to be absorbed than carbohydrates with high-glycemic-indices.

The "glycemic index" is a system of predicting subsequent rises in blood glucose after ingestion of carbohydrate-containing foods (Anderson, J. S. et al., Modern Nutrition in Health and Disease, ch. 70: 1259-86 (1994); Wolever, T. M. S. et al., Am. J. Clin. Nutr., 54: 846-54 (1991); Wolever, T. M. S. et al., Diab. Care, 12: 126-32 (1990)). The glycemic index characterizes the rate of carbohydrate absorption after a meal. It is defined as the area under the glycemic response curve during a 2-hour period after consumption of 50 g of carbohydrate from a test food divided by the area under the curve of a standard, which is either white bread or glucose. The glycemic index carbohydrates have the highest peak circulating glucose in a 2 hour period following ingestion of food. Conversely, low-glycemic-index carbohydrates cause a lower peak glucose and smaller area under the curve.

Many factors determine the glycemic index of foods. These include carbohydrate type, fiber, protein and fat content and the method of preparation (overcooked foods evoke a higher response). Generally high-glycemic-index carbohydrates are highly refined, and have a relatively high amount of glucose or starch compared to lactose, sucrose or fructose. Also, they are low in soluble fiber. The inclusion of fiber is important due to the way fiber facilitates weight loss by forming a gel with the food in the stomach. This gelling action reduces the rate of gastric emptying and hence digestion rates which promote satiety. Other factors which affect satiety are the amount of carbohydrate, the complexity of the carbohydrate, and the other foods that are eaten simultaneously with the carbohydrate (e.g., fiber, protein, fat) (Ludwig, D. S., J Nutr., 130: 280S-3S (2000); Wolever, T. M. S. et al., Am. J. Clin. Nutr., 54: 846-54 (1991); Wolever, T. M. S. et al., Diab. Care, 12: 126-32 (1990)). Bread and potatoes raise blood glucose more than beans. Other foods containing no or non-digestible carbohydrate ingested at the same time as carbohydrates (e.g., fat, fiber and protein) reduces postprandial blood glucose and insulin levels (Wolever, T. M. S., et al., Am. J. Clin. Nutr., 54: 846-54 (1991)).

The low-glycemic-index carbohydrate source can be provided by a single carbohydrate or a combination. The carbohydrate source can further provide a source of fiber and may be a natural sweetener, fructose, barley, konjac mannan, psyllium and combinations thereof. The protein source is of a high biological value and is selected from at least one of the following: whey protein concentrate, casein, soy, milk, egg and combinations of these. Additionally, the nutritional supplement may contain, micronutrients, vitamins, minerals, dietary supplements (e.g., herb), nutrients, emulsifiers, flavorings and edible compounds.

In one embodiment, the nutritional supplement formulation may further include a carbohydrate for sweetening the nutritional supplement. Exemplary carbohydrates useful for sweetening the nutritional supplement include, but are not limited to, fructose, evaporated cane juice, inulin, agave, honey, maple syrup, brown rice syrup, malt syrup, date sugar, fruit juice concentrate, and mixed fruit juice concentrate.

Dietary fiber that may be suitable for use in the invention includes but is not limited to cellulose, seeds, hemicellulose (e.g., bran, whole grains), polyfructose (e.g., inulin and oligofructans), polysaccharide gums (e.g., Larch Arabinogalactan), oatmeal, barley, pectins, lignin, resistant starches. Examples of suitable fiber sources include but are not limited to wheat bran, cellulose, oat bran, corn bran, guar, pectin, and psyllium.

Sources of protein can be any suitable protein utilized in nutritional formulations and can include whey protein, whey protein concentrate, whey powder, egg, soy protein, soy protein isolate, caseinate (e.g., sodium caseinate, sodium calcium caseinate, calcium caseinate, and potassium caseinate), animal and vegetable protein and mixtures thereof. When choosing a protein source, the biological value of the protein should be considered first, with the highest biological values being found in caseinate, whey, lactalbumin, soy, delactosed milk solids, egg albumin and whole egg proteins. These proteins have high biological value; that is, they have a high proportion of the essential amino acids.

The nutritional supplement can also contain other ingredients such as one or a combination of other vitamins, minerals, antioxidants, fiber (e.g., ginkgo biloba, ginseng) and other nutritional supplements. Selection of one or several of these ingredients is a matter of formulation design, consumer and end-user preference. The amount of these ingredients added to the nutritional supplements of this invention are readily known to the skilled artisan and guidance to such amounts can be provided by the RDA and DRI (Dietary Reference Intake) doses for children and adults. Vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacin amide; zinc sulfate or oxide; calcium pantothenate; copper gluconate; riboflavin; beta-carotene; pyridoxine hydrochloride; thiamin mononitrate; folic acid; biotin; chromium chloride or picolinate; potassium iodide; selenium; sodium selenate; sodium molybdate; phylloquinone; Vitamin D3; cyanocobalamin; sodium selenite; copper sulfate; Vitamin A; Vitamin E; vitamin B6 and hydrochloride thereof. Vitamin C; inositol; Vitamin B12; potassium iodide.

The amount of other ingredients per unit serving is a matter of design and will depend upon the total number of unit servings of the nutritional supplement daily administered to the patient. The total amount of other ingredients will also depend, in part, upon the condition of the patient. Preferably the amount of other ingredients will be a fraction or multiplier of the RDA or DRI amounts. For example, the nutritional supplement will comprise 50% RDI (Reference Daily Intake) of vitamins and minerals per unit dosage and the patient will consume two units per day.

Flavors, coloring agents, spices, nuts and the like can be incorporated into the product. Flavorings can be in the form of flavored extracts, volatile oils, chocolate flavorings (e.g., non-caffeinated cocoa or chocolate, or chocolate substitutes, such as carob), peanut butter flavoring, cookie crumbs, crisp rice, vanilla or any commercially available flavoring. Flavorings can be protected with mixed tocopherols. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch or toffee. In a preferred embodiment, the nutritional supplement contains berry or other fruit flavors. The food compositions may further be coated, for example with a yogurt coating, if it is produced as a bar.

Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain artificial sweeteners, e.g., saccharides, cyclamates, aspartamine, aspartame, acesulfame K, and/or sorbitol. Such artificial sweeteners can be desirable if the nutritional supplement is intended for an overweight or obese individual, or an individual with type II diabetes who is prone to hyperglycemia.

The nutritional supplements of the present invention may be formulated using any pharmaceutically acceptable forms of the vitamins, minerals and other nutrients discussed above, including their salts. They may be formulated into capsules, tablets, powders, suspensions, gels or liquids optionally comprising a physiologically acceptable carrier, such as but not limited to water, milk, juice, sodas, starch, vegetable oils, salt solutions, hydroxymethyl cellulose, and carbohydrate. In one embodiment, the nutritional supplements may be formulated as powders, for example, for mixing with consumable liquids, such as milk, juice, sodas, water or consumable gels or syrups for mixing into other nutritional liquids or foods. The powdered form has particular consumer appeal, is easy to administer and incorporate into one's daily regimen, thus increasing the chances of patient compliance. The nutritional supplements of this invention may be formulated with other foods or liquids to provide premeasured supplemental foods, such as single serving breakfast bars, energy bars, breads, cookies, brownies, crackers, cereals, cakes, or beverages, for example.

Thus, the nutritional supplement formulation may be administered as a dietary supplement or as an additive to a consumable carrier such as a foodstuff. The composition may be incorporated into a foodstuff that is later cooked or baked. The components of the composition are structurally stable to remain un-oxidized and are heat stable at temperatures required for baking or cooking.

To manufacture such a beverage, the ingredients are dried and made readily soluble in water or other consumable liquids as described above. The beverage is a preferred nutritional supplement form due to its ability to aid in the sensation of satiety if consumed at least one half hour prior to meals.

To manufacture such a food bar, the dry ingredients are added with the liquid ingredients in a mixer and mixed until the dough phase is reached; the dough is put into an extruder and extruded; the extruded dough is cut into appropriate lengths; and the product is cooled.

For manufacture of other foods or beverages, the ingredients comprising the nutritional supplement of this invention can be added to traditional formulations or they can be used to replace traditional ingredients. Those skilled in food formulating will be able to design appropriate foods/beverages with the objective of this invention in mind.

The nutritional supplement can be made in a variety of forms, such as puddings, confections, (i.e., candy), nutritional beverages, ice cream, frozen confections and novelties, or baked or non-baked, extruded food products such as bars. In one embodiment, nutritional supplement is in the form of a powder for a beverage or a non-baked extruded nutritional bar.

In one embodiment, the consumable carrier is a meat product, such as natural or cultured meat. In vitro meat, also known as cultured meat, is animal flesh that has never been part of a complete, living animal. The process of developing in vitro meat involves taking muscle cells and applying a protein that helps the cells to grow into large portions of meat. Once the initial cells have been obtained, additional animals would not be needed—akin to the production of yogurt cultures. In one embodiment, the production of in vitro meat: loose muscle cells and structured muscle, the latter one being vastly more challenging than the former. Muscles consist of muscle fibers, long cells with multiple nuclei. Such cells do not proliferate by themselves, but arise when precursor cells fuse. Precursor cells can be embryonic stem cells or satellite cells, specialized stem cells in muscle tissue. Theoretically, it is relatively simple to culture them in a bioreactor and then make them fuse. For the growth of real muscle, however, the cells should grow "on the spot," which requires a perfusion system akin to a blood supply to deliver nutrients and oxygen close to the growing cells, as well as to remove the waste products. In addition, other cell types, such as adipocytes, need to be grown, and chemical messengers should provide clues to the growing tissue about the structure. Lastly, muscle tissue needs to be physically stretched or "exercised" to properly develop (see, e.g., U.S. Pat. No. 6,835,390 and published International application no. WO 99/31222, both of which are incorporated herein by reference). In yet another embodiment, the invention includes cultured meat that is engineered to express ZAG in sufficient quantities such that addition of recombinant ZAG is unnecessary.

The ingredients can be administered in a single formulation or they can be separately administered. For example, it may be desirable to administer a bitter tasting ingredient in a form that masks its taste (e.g., capsule or pill form) rather than incorporating it into the nutritional composition itself (e.g., powder or bar). Thus, the invention also provides a pharmaceutical pack or kit comprising one or more containers filled with one or more of the ingredients of the nutritional compositions of the invention. Optionally associated with such container(s) can be a notice in the form prescribed by a government agency regulating the manufacture, use or sale of pharmaceutical or dietary supplement products, which notice reflects approval by the agency of manufacture, use of sale for human administration. The pack or kit can be labeled with information regarding mode of administration, sequence of administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a formulation or tablet. Agents assembled in a blister pack or other dispensing means is preferred.

In one embodiment, the formulation includes about 1.0 mg to 1000 mg ZAG. In another embodiment, the formulation includes about 1.0 mg to about 500 mg ZAG. In another embodiment, the formulation includes about 1.0 mg to about 100 mg ZAG. In another embodiment, the formulation includes about 1.0 mg to about 50 mg ZAG. In another embodiment, the formulation includes about 1.0 mg to about 10 mg ZAG. In another embodiment, the formulation includes about 5.0 mg ZAG.

Accordingly, in another aspect, the invention provides the use of anti-ZAG antibodies, or functional fragments thereof, as herein defined, for the manufacture of a medicament useful in human medicine for treating symptoms and/or conditions associated with cachexia or diseases associated with muscle wasting disorders.

In one embodiment, the formulation of the present invention is administered orally. In such embodiments, the formulation is at least 70, 75, 80, 85, 90, 95 or 100% as effective as any other route of administration.

The total amount of formulation to be administered in practicing a method of the invention can be administered to a subject as a single dose, either as a bolus or by ingestion over a relatively short period of time, or can be administered using a fractionated treatment protocol, in which multiple doses are administered over a prolonged period of time (e.g., once daily, twice daily, etc.). One skilled in the art would know that the amount of formulation depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

Accordingly, in certain embodiments, the methods of the invention include an intervalled treatment regimen. It was observed that long-term daily administration of ZAG in ob/ob mice results in continuous weight loss. As such, in one embodiment, the treatment of ZAG or anti-ZAG antibodies, alone or in combination with one or more β-AR antagonists or β3-AR agonists, is administered every other day. In another embodiment, the treatment is administered every two days. In another embodiment, the treatment is administered every three days. In another embodiment, the treatment is administered every four days.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLE 1

Zinc-$\alpha_2$-glycoprotein Attenuates Hyperglycemia

To evaluate the ability of Zinc-$\alpha_2$-glycoprotein (ZAG) to attenuate obesity and hyperglycemia ob/ob mice were administered ZAG which induced a loss of body weight, and a rise in body temperature, suggesting an increased energy expenditure. Expression of uncoupling proteins-1 and -3 in brown adipose tissue were increased, while there was a decrease in serum levels of glucose, triglycerides and non-esterified fatty acids, despite an increase in glycerol, indicative of increased lipolysis. There was a decrease in plasma insulin and an improved response to intravenous glucose together with an increased glucose uptake into adipocytes and skeletal muscle. Expression of hormone-sensitive lipase in epididymal adipocytes was increased. There was an increase in skeletal muscle mass due to an increase in protein synthesis and decrease in degradation. This suggests that ZAG may be effective in the treatment of hyperglycemia.

Dulbeccos' Modified Eagle's (DMEM) and Freestyle media were purchased from Invitrogen (Paisley, UK) while fetal calf serum was from Biosera (Sussex, UK). 2-[1-$^{14}$C] Deoxy-D-glucose (sp.act.1.85 GBq mmol$^{-1}$) and L-[2,6-$^3$H] phenylalanine (sp.act.37Bq mmol$^{-1}$) were from American Radiolabeled Chemicals (Cardiff, UK). Rabbit polyclonal antibody to phospho (Thr-202) and total ERK1, total p38MAPK, phospho HSL (Ser-552), glucose transporter 4 (GLUT4), adipose triglyceride lipase, hormone sensitive lipase, and phospho PLA2 (Ser-505) and to human ATGL were purchased from Abcam (Cambridge, UK). Mouse monoclonal antibody to full length human ZAG was from Santa Cruz (California, USA), and mouse monoclonal antibody to myosin heavy chain type II was from Novacastra (via Leica Biosystems, Newcastle, UK). Mouse monoclonal antibodies to 20S proteasome α-subunits and p42 were from Affiniti Research Products (Exeter, UK). Mouse monoclonal antibody to phospho (Thr-180/Tyr-182) p38MAPK and rabbit polyclonal antisera to total and phospho (Thr-451) PKR, phospho (Ser-162) eIF2α and to total eIF2α were from New England Biosciences (Herts, UK). Polyclonal rabbit antibodies to UCP1, UCP3 and total PKR and PHOSPHO-SAFE™ Extraction Reagent were from Calbiochem (via Merk Chemicals, Nottingham, UK). Peroxidase-conjugated goat anti-rabbit and rabbit anti-mouse antibodies were purchased from Dako (Cambridge, UK). Polyclonal rabbit antibody to mouse β-actin and the triglyceride assay kit were purchased from Sigma Aldrich (Dorset, UK). Hybond A nitrocellulose membranes and enhanced chemiluminescence (ECL) development kits were from Amersham Pharmacia Biotech (Bucks, UK). A WAKO colorimetric assay kit for NEFA was purchased from Alpha Laboratories (Hampshire, UK), and a mouse insulin ELISA kit was purchased from DRG (Marburg, Germany). Glucose measurements were made using a Boots (Nottingham, UK) plasma glucose kit.

Production of Recombinant ZAG—HEK293F cells were transfected with full length human ZAG cDNA in the expression vector pcDNA 3.1, and maintained in FreeStyle medium under an atmosphere of 5% $CO_2$ in air at 37° C. ZAG was secreted into the medium, which was collected, and maximal protein levels (16 μgml$^{-1}$) were obtained after 14 days of culture. To purify ZAG, media (200 ml) was centrifuged at 700 g for 15 min to remove cells, and concentrated into a volume of 1 ml sterile PBS using an Amicon Ultra-15 centrifugal filter with a 10 kDa cut-off. The concentrate (about 2 mg protein) was added to 2 g DEAE cellulose suspended in 20 ml 10 mM Tris, pH 8.8 and stirred for 2 h at 4° C. The DEAE cellulose bound ZAG and it was sedimented by centrifugation (1500 g for 15 min) and the ZAG was eluted by stirring with 20 ml 10 mM Tris, pH8.8 containing 0.3M NaCl for 30 min at 4° C. The eluate was washed and concentrated into a volume of 1 ml in sterile PBS using an Amicon centrifugal filter. The purified ZAG was free of endotoxin, as determined with a LAL Pyrogent single test kit (Lonza, Bucks, UK).

Cell Culture and Purification of ZAG. Single-cell suspensions of white adipocytes were prepared from minced adipose deposits by incubation at 37° C. for 2 h in Krebs-Ringer bicarbonate buffer containing 1.5 mgml$^{-1}$ collagenase, and 4% bovine serum albumin under an atmosphere of 95% oxygen: 5% $CO_2$ as previously described. For time-course studies adipocytes were suspended in DMEM containing 10% fetal calf serum at a concentration of $10^5$ cells $ml^{-1}$ and maintained under an atmosphere of 10% $CO_2$ in air at 37° C. Human 293 cells transfected with a plasmid containing human ZAG were seeded at a concentration of $10^5$ cells $ml^{-1}$ in FreeStyle medium and maintained under an atmosphere of 5% $CO_2$ in air at 37° C. Maximal protein levels (16 µgml$^{-1}$) were obtained after 14 days of culture. The media (200 ml) was then centrifuged at 700 g for 15 min to remove cells and concentrated into a volume of 1 ml of sterile PBS using an Amicon Ultra-15 centrifugal filter with a 10 kDa cut-off After measurement of the protein concentration of the sample (about 2 mg) it was added to 2 g DEAE cellulose suspended in 20 ml of 10 mM Tris, pH8.8 and stirred at 4° C. for 2 h. ZAG being negatively charged binds to the DEAE cellulose, which was sedimented by centrifugation (1500 g for 15 min), and eluted by stirring with 20 ml 10 mM Tris, pH8.8 containing 0.3M NaCl for 30 min at 4° C. The supernatant was washed and concentrated to a volume of 1 ml in sterile PBS using the Amicon centrifugal filter.

Animals—Mice. Homozygous obese (ob/ob) mice from the colony maintained at Aston University were used in the present study. The origin and characteristics of Aston ob/ob mice have been previously described. Male mice (20-21 weeks old, weight 90-100 g) were grouped into three per cage in an air conditioned room at 22±2° C. with a 12 h-light:12 h-dark cycle and fed a rat and mouse breeding diet (Special Diet Services, Witham, UK) and tap water ad libitum. They were administered ZAG (35 µg) in PBS (100 µl) b.d. by i.v. administration and body weight and food and water intake were monitored daily. Control mice received PBS alone. Body temperature was measured daily by the use of a rectal thermometer (RS Components, Northants, UK). All animal experiments were carried out in accordance with the U.K. Animals (Scientific Procedures) Act 1986. No adverse effects were observed after administration of ZAG.

Animal—Rats. Mature male Wistar rats (one year old from our own colony) weighing 540±82.5 g were housed individually and treated once daily i.v., with either ZAG in PBS (100 µl) (50 µg per 100 g body weight), or with PBS (100 µl) as a control. Both food and water intake and body weight were measured daily. Animals were given free access to food (Special Diet Services, Essex, UK) and water ad libitum. The animal experiment was carried out under the welfare conditions imposed by the British Home Office. After 10 days treatment the animals were terminated and the body composition determined. Animals were heated to 80-90° C. for 7 days until constant weight was achieved. The water content was then determined from the difference between the wet and dry weight. Lipids were extracted from the dry carcass using a sequence of chloroform:methanol (1:1), ethanol/acetone (1:1) and diethyl ether (120 ml of each) as described by Lundholm et al (14). The solvents were evaporated and the fat weighed. The non-fat carcass mass was calculated as the difference between the initial weight of the carcass and the weight of water and fat.

Lipolytic assay. Samples to be assayed were incubated with $10^5$ to $2\times10^5$ adipocytes for 2 h in 1 ml Krebs-Ringer bicarbonate buffer, pH 7.2. The concentration of glycerol released was determined enzymatically by the method of Wieland (Wieland, O. Glycerol UV method. In Methods of Enzymatic Analysis (ed. Bergmeyer, H.U.) (Academic Press, London, UK, pp 1404-1409, 1974)). Control samples containing adipocytes alone were analysed to determine the spontaneous glycerol release. Activity was expressed as µmol glycerol released/$10^5$ adipocytes/2 h.

Serum Metabolite Determinations. Non-esterified fatty acids (NEFA) were determined using a Wako-ASC-ACOD kit (Wako Chemical GmbH, Neuss, Germany). Triglycerides were determined using a Triglyceride kit (Sigma Chemical Co., Poole, United Kingdom) and 3-hydroxybutyrate by a quantitative enzymatic determination kit (Sigma). Glucose was measured using a glucose analyser (Beckman, Irvine, Calif.) and glycerol was determined enzymatically using the method of Wieland as described in "Methods of Enzymatic Analysis" (Ed. Bergmeyer, H. U.) Vol. 3, pp1404-1409, published by Academic Press, London (1974).

Isolation of Mouse Adipocyte Plasma Membranes. In a typical procedure white adipocytes were isolated from mouse epididymal fat pads as referred to above except that the cells were washed in 250 mM sucrose, 2 mM ethyleneglycol bis(β-aminoethylether)-N,N,N',N'(EGTA), 10 mM Tris-HCl (pH 7.4). Adipocytes were resuspended in 20 ml of the above buffer and homogenised by aspirating through a Swinny filter at least 10 times. The cell homogenate was then centrifuged at 300 g for 5 min, the fat cake removed from the surface and the remaining pellet and infranatant transferred to clean tubes. These were centrifuged at 30,000 g for 1 h at 4° C. and the membrane pellet formed was resuspended in the sucrose buffer (200 to 400 µl). Plasma membranes were separated from other organelle membranes on a self-forming gradient of PERCOLL™ colloidial silica particles. The constituents were 250 mM sucrose, 2 mM EGTA, 10 mM Tris-HCl, pH 7.4; PERCOLL™; and 2M sucrose, 8 mM EGTA, 80 mM Tris-HCl, pH 7.4, mixed in a ratio of 32:7:1 together with the membrane suspension (in a total volume of 8 ml). This mixture was centrifuged at 10,000 g for 30 min at 4° C. The gradient was fractionated into 0.75 ml portions and each portion was assayed for the presence of succinate dehydrogenase, NADH-cytochrome c reductase, lactate dehydrogenase and 5'-nucleotidase to locate the plasma membrane fraction. The membrane fractions were resuspended in 150 mM NaCl, 1 mM EGTA, 10 mM Tris-HCl, pH 7.4 and centrifuged at 10,000 g at 4° C. for 2 min. The process was repeated twice. The washed plasma membranes were then diluted in 10 mM Tris-HCl, pH 7.4, 250 mM sucrose, 2 mM EGTA and 4 µM phenylmethylsulfonyl fluoride (PMSF) at 1-2 mg/ml, snap frozen in liquid nitrogen and stored at −70° C. until use.

Lipolytic Activity in Rat Adipocytes—White adipocytes were prepared from finely minced epididymal adipose tissue of male Wistar rats (400 g) using collagenase digestion, as described (Beck S A, et al. Production of lipolytic and proteolytic factors by a murine tumor-producing cachexia in the host. Cancer Res 47:5919-5923, 1987). Lipolytic activity was determined by incubating $10^5$-$2\times10^5$ adipocytes for 2 h in 1 ml Krebs-Ringer bicarbonate buffer, pH 7.2, and the extent of lipolysis was determined by measuring the glycerol released (Wieland O. Glycerol UV method. Methods of Enzymatic Analysis, edited by Bergmeyer H U. Academic Press, London, pp 1404-1409, 1974). Spontaneous glycerol release was measured by incubating adipocytes alone. Lipolytic activity was expressed as µmol glycerol released/$10^5$ adipocytes/2 h.

Gel Electrophoresis. Gels were prepared according to the method of Laemmli and generally consisted of a 5% stacking gel and a 15% SDS-PAGE resolving gel (denaturing or reducing conditions) or a 10% SDS-PAGE resolving gel (non-denaturing or non-reducing conditions). Samples were loaded at 1-5 µg/lane. Bands were visualized by staining either with Coomassie brilliant blue R-250 or by silver. Samples were prepared for reducing conditions by heating for 5 min at 100° C. in 0.0625M Tris-HCl, pH 6.8, 10% glycerol, 1% SDS, 0.01% bromophenol blue and 5% 2-mercaptoethanol.

Glucose Uptake into Adipocytes. Isolated adipocytes ($5 \times 10^4$) were washed twice in 1 ml Krebs-Ringer bicarbonate buffer, pH 7.2 (KRBS) and further incubated for 10 min at room temperature in 0.5 ml KRBS containing 18.5 MBq 2-[1-$^{14}$C] deoxy-D-glucose and non-radioactive 2-deoxy-D-glucose to a final concentration of 0.1 mM. Uptake was terminated by the addition of 1 ml ice-cold glucose-free KRBS, and the cells were washed three times with 1 ml KRBS, lysed by addition of 0.5 ml 1M NaOH and left for at least 1 h at room temperature before the radioactivity was determined by liquid scintillation counting.

Glucose Uptake into Gastrocnemius Muscle—Gastrocnemius muscles were incubated in Krebs-Henseleit bicarbonate buffer for 45 min at 37° C. and then incubated for a further 10 min in 5 ml Krebs-Henseleit buffer containing 185M Bq 2-[1-$^{14}$C] deoxy-D-glucose and non-radioactive 2-deoxy-D-glucose to a final concentration of 0.1 mM. The muscles were then removed and washed in 0.9% NaCl for 5 min followed by dissolution in 0.5 ml 1M NaOH and the radioactivity was determined by liquid scintillation counting.

Glucose Uptake into Soleus Muscle. Soleus muscles were incubated in Krebs-Henseleit bicarbonate buffer for 45 min at 37° C. and then incubated for a further 10 min in 5 ml Krebs-Henseleit buffer containing 185 MBq 2-[1-$^{14}$C] deoxy-D-glucose and non-radioactive 2-deoxy-D-glucose to a final concentration of 0.1 mM. The muscles were then removed and washed in 0.9% NaCl for 5 min, followed by dissolution in 0.5 ml 1MNaOH and the radioactivity was determined by liquid scintillation counting.

Protein Synthesis and Degradation in Muscle. The method for the determination of protein synthesis and degradation in muscle has been previously described (Smith, K. L. & Tisdale, M. J. Increased protein degradation and decreased protein synthesis in skeletal muscle during cancer cachexia. Br. J. Cancer 67, 680-685 (1993)). Gastrocnemius muscles were excised using ligatures and incubated for 30 min at 37° C. in RPMI 1640 medium lacking phenol red and saturated with $O_2$:$CO_2$ (19:1) and then washed with PBS. Protein synthesis was measured by the incorporation of L-[2,6-$^3$H] phenylalanine (640 MBq) into acid-insoluble material using a 2 h period in which the muscles were incubated at 37° C. in RPMI/640 without phenol red and saturated with $O_2$:$CO_2$ (19:1). Muscles were then rinsed in non-radioactive medium, blotted and homogenised in 2% perchloric acid. The rate of protein synthesis was calculated by dividing the amount of protein-bound radioactivity by the amount of acid soluble radioactivity. Protein degradation was determined by the release of tyrosine from gastrocnemius muscle over a 2 h period in 3 ml of oxygenated Krebs-Henseleit buffer, pH7.4, containing 5 mM glucose and 0.5 mM cycloheximide.

Measurement of Proteasome and Caspase Activity. The 'chymotrypsin-like' activity of the proteasome was determined fluorometrically by measuring the release of 7-amido-4-methylcoumarin (AMC) at an excitation wavelength of 360 nm and an emission wavelength of 460 nm from the fluorogenic substrate N-succinyl Lys Lys Val Tyr.AMC (SEQ ID NO: 2) as previously described for myotubes (Whitehouse, A. S. & Tisdale, M. J. Increased expression of the ubiquitin-proteasome pathway in murine myotubes by proteolysis-inducing factor (PIF) is associated with activation of the transcription factor NF-κB. Br. J. Cancer 89, 1116-1122 (2003)). Gastrocnemius muscle was homogenised in 20 mM Tris, pH7.5, 2 mM ATP, 5 mM $MgCl_2$ and 50 mM DTT at 4° C., sonicated and centrifuged at 18,000 g for 10 min at 4° C. to pellet insoluble material, and the resulting supernatant was used to measure 'chymotrypsin-like' enzyme activity in the presence or absence of the proteasome inhibitor lactacystin (10 μM). Only lactacystin suppressible activity was considered as true proteasome activity. The activity of caspase-3 was determined by the release of AMC from AcAsp.Gly.Val.Asp.AMC (SEQ ID NO: 3), and the activity of caspase-8 was determined by the release of 7-amino-4-trifluromethylcoumarin (AFC) from the specific substrate Z-Ile Glu Phe Thr Asp-AFC (SEQ ID NO: 4), using the supernatant from above (50 μg protein), and either the caspase-3 or -8 substrate (10 μM) for 1 h at 37° C., in the presence or absence of the caspase-3 (AcAspGlu-ValAsp-CHO) (SEQ ID NO: 5) or caspase-8 (Ile Glu Phe Thr Asp-CHO) (SEQ ID NO: 6) inhibitors (100 μM). The increase in fluorescence due to AFC was determined as above, while the increase in fluorescence due to AFC was measured with an excitation wavelength of 400 nm and an emission wavelength of 505 nm. The difference in values in the absence and presence of the caspase inhibitors was a measure of activity.

Western Blot Analysis. Freshly excised gastrocnemius muscles were washed in PBS and lysed in PHOSPHO-SAFE™ Extraction Reagent for 5 min at room temperature followed by sonication at 4° C. The lysate was cleared by centrifugation at 18,000 g for 5 min at 4° C. and samples of cytosolic protein (5 μg) were resolved on 12% sodium dodecyl sulfate-polyacrylamide gel electrophoresis at 180V for approximately 1 h. This was followed by transference to 0.45 μm nitrocellulose membranes, which were then blocked with 5% Marvel in Tris-buffered saline, pH 7.5, at 4° C. overnight. Both primary and secondary antibodies were used at a dilution of 1:1000 except anti-myosin (1:250). Incubation was for 1 h at room temperature, and development was by ECL. Blots were scanned by a densitometer to quantify differences.

Samples of epididymal WAT, BAT and gastrocnemius muscle excised from rats treated with ZAG or PBS for 5 days were homogenized in 0.25M sucrose, 1 mM HEPES, pH 7.0 and 0.2M EDTA, and then centrifuged for 10 min at 4,500 rpm. Samples of cytosolic protein (10 μg) were resolved on 12% sodium dodecylsulphate polyacrylamide gel electrophoresis and the proteins were then transferred onto 0.45 μm nitrocellulose membranes, which had been blocked with 5% Marvel in Tris-buffered saline, pH 7.5, at 4° C. overnight, and following four 15 min washes with 0.1% Tween in PBS, incubation with the secondary antibody was performed for 1 h at room temperature. Development was by ECL.

Statistical Analysis. The results are shown as means±SEM for at least three replicate experiments. Difference in means between groups was determined by one-way analysis of variance (ANOVA) followed by the Tukey-Kramer multiple comparison test. P values less than 0.05 were considered significant.

Figure 1B:
FIG. 1B is a pictorial diagram showing the results of a Western blot showing expression of ZAG in culture medium and purified ZAG.
Figure 1C:
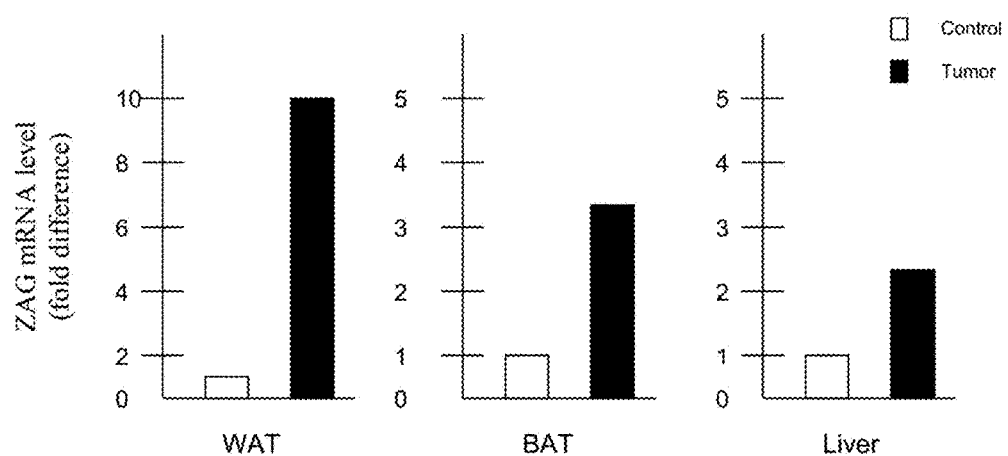
FIG. 1C is a graphical diagram showing ZAG mRNA levels in adipose tissue and liver tissue in MAC16 mice undergoing weight loss. $P<0.01$.
Figure 1D:
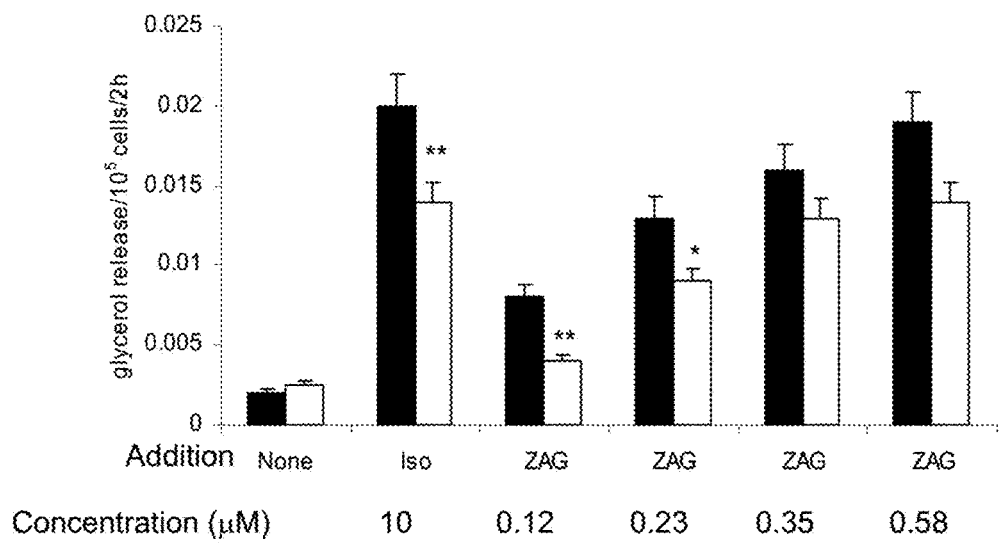
FIG. 1D is a graphical diagram showing the results of lipolysis in epididymal adipocytes from non-obese (■) and ob/ob mice (□) in response to isoprenaline (Iso) and ZAG. Differences from non-obese mice are shown as * $p<0.05$,  $p<0.01$ and * $p<0.001$.
Figure 1E:
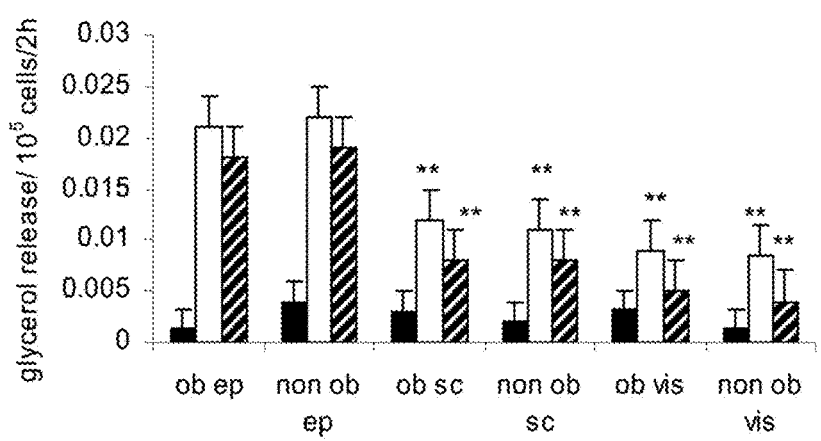
FIG. 1E is a graphical diagram showing the results of lipolysis in adipocytes from epididymal (ep), subcutaneous (s.c.) and visceral (vis) deposits from obese (ob/ob) and non-obese (non ob) mice with either no treatment (■), isoprenaline (10 μM) (□) or ZAG (0.46 μM) (◨). Differences from epididymal adipocytes are shown as ** $p<0.01$.
Figure 1F:
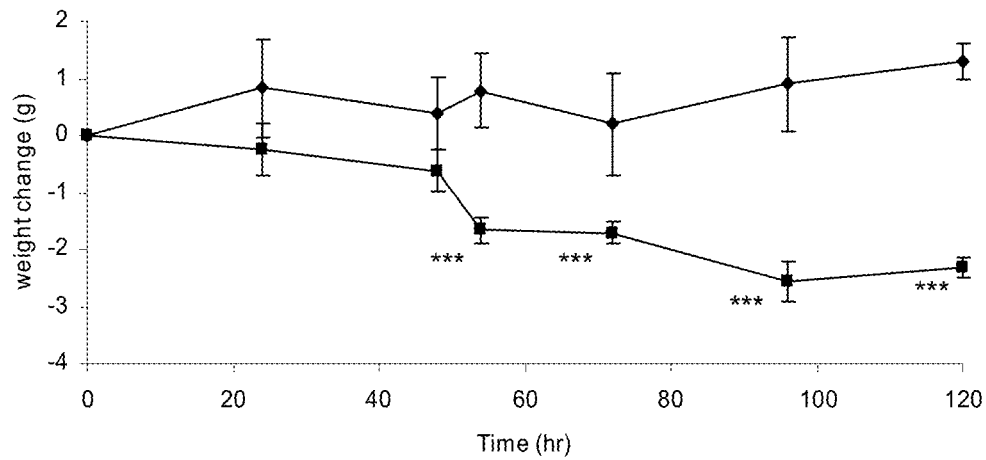
FIG. 1F is a graphical diagram showing the effect of ZAG (■) on body weight of ob/ob mice in comparison with PBS (◆) as described in the methods. Differences in weight form time zero and PBS controls are shown as *** $p<0.001$.

Results—Mice. Purification of ZAG resulted in a product that was greater than 95% pure (FIG. 1A), confirmed as ZAG by immunoblotting (FIG. 1B). ZAG stimulated lipolysis in epididymal adipocytes (FIG. 1D) but the lipolytic effect was considerably reduced in adipocytes from both subcutaneous and visceral deposits, although it was significantly elevated over basal levels (FIG. 1E). There was no significant difference in the extent of stimulation of lipolysis between isoprenaline and ZAG in any adipocyte group, although ZAG was more potent at inducing lipolysis than isoprenaline on a molar basis. The effect of ZAG on the body weight of ob/ob mice over a 5 day period is shown in FIG. 1F. While control animals remained weight stable, animals treated with ZAG showed a progressive weight loss, such that after 5 days there was a 3.5 g weight difference between the groups, despite equal food (PBS 32±3.1 g; ZAG 30±2.5 g) and water (PBS 140±8.2 ml; ZAG 135±3.2 ml) intake over the course of the experiment. There was a significant rise of body temperature of 0.4° C. after 4 days of ZAG administration (FIG. 1G), indicative of an increase in basal metabolic rate. Measurement of plasma metabolite levels suggest an increase in metabolic substrate utilization in ZAG treated animals (Table 1). Thus there was a significant decrease in plasma glucose, triglycerides (TG) and non-esterified fatty acids (NEFA) in ZAG-treated animals, despite an increased glycerol concentration indicative of an increased lipolysis. There was a 36% decrease in plasma insulin levels suggesting that ZAG is effective in reducing the diabetic state. ZAG mRNA levels in various tissues are shown in FIG. 1C.

TABLE 1

Plasma metabolite and insulin levels in ob/ob mice treated with ZAG for 120 h

|  | PBS | ZAG |
|---|---|---|
| Glucose (mmol/L) | 24.5 + 0.4 | 20.3 + 0.8 p < 0.01 |
| TG (mmol/L) | 1.2 + 0.3 | 0.9 + 0.1 p < 0.05 |
| Glycerol (µmol/L) | 359 + 23 | 429 + 36 p < 0.001 |
| Insulin (ng/mL) | 41.2 + 0.6 | 26.3 + 0.52 p < 0.001 |
| BAT (g) | 0.35 ± 0.09 | 0.73 ± 0.12 p < 0.01 |
| NEFA (mEq/L) | 0.6 + 0.12 | 0.23 + 0.05 p < 0.001 |
| Soleus (g) | 0.52 ± 0.13 | 0.80 ± 0.09 p < 0.01 |
| Gastrocnemius (g) | 0.85 ± 0.12 | 1.12 ± 0.14 p < 0.01 |
| Insulin Pancreas (pg/g pancrease) | 4.52 ± 2.91 | 16.3 ± 3.1 p = 0.0042 |

Figure 2A:
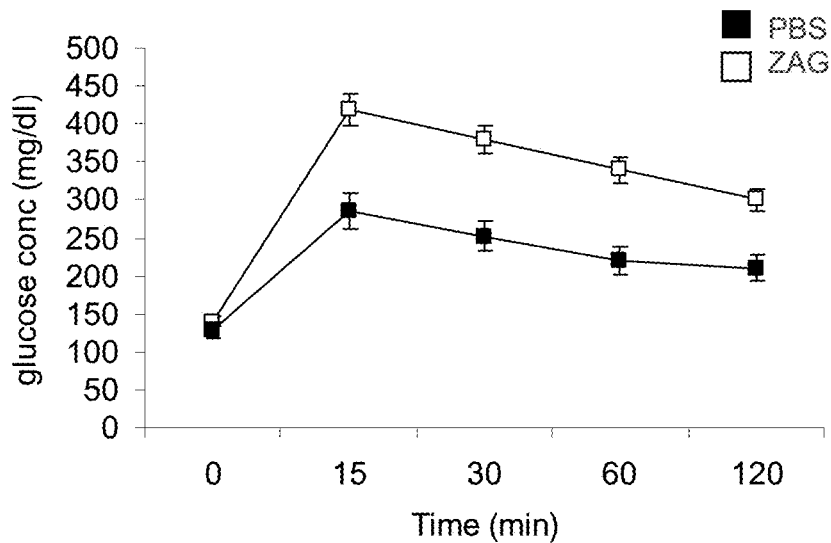
FIG. 2A is a graphical diagram showing glucose tolerance of ob/ob mice treated with ZAG. Plasma glucose levels in ob/ob mice in the fed state either treated with ZAG (■) or PBS (◆) for 3 days after i.v. administration of glucose (2 g/kg). $p<0.001$ from PBS. Blood samples were removed from the tail vein at intervals after glucose administration and used for the measurement of glucose and insulin.
Figure 2B:
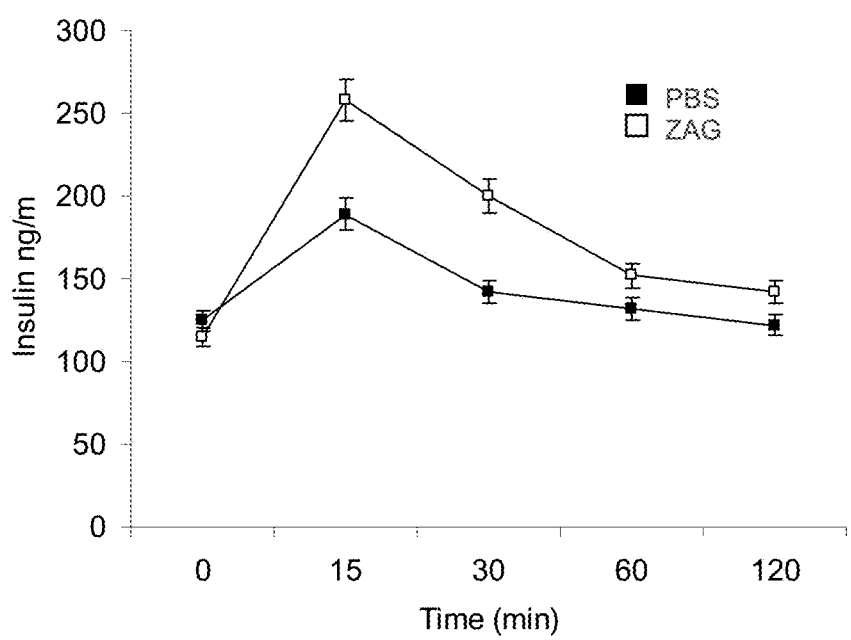
FIG. 2B is a graphical diagram showing plasma insulin levels in ob/ob mice treated with ZAG after oral administration of glucose (1 g/kg). $p<0.001$ from PBS.
Figure 2C:
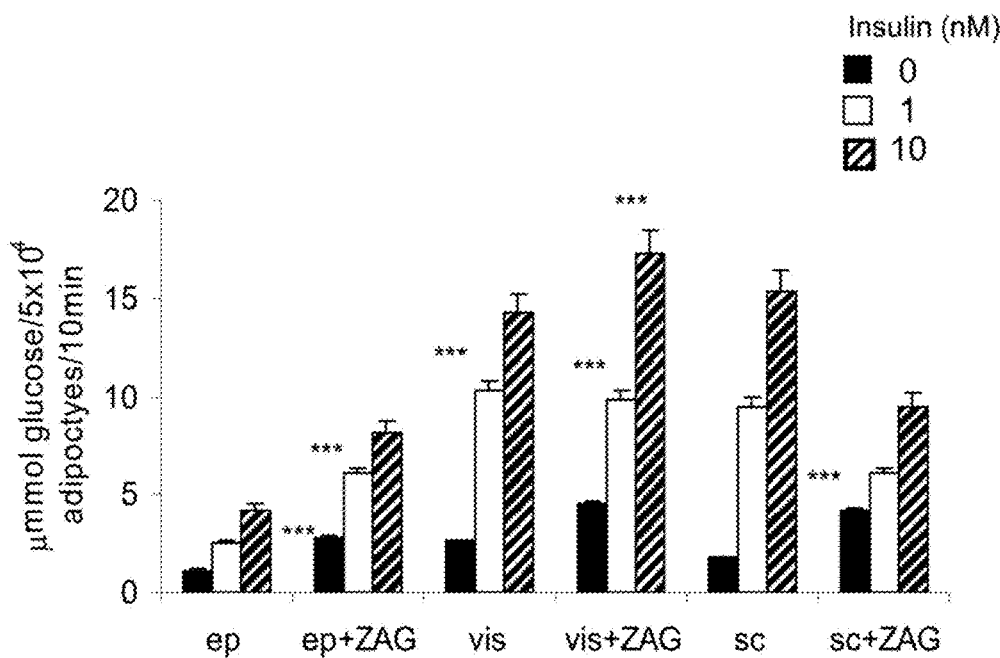
FIG. 2C is a graphical diagram showing glucose uptake into epididymal (ep), visceral (vis) and subcutaneous (s.c.) adipocytes of ob/ob mice treated with ZAG for 5 days in the presence of 0 (■), 1(□) or 10 nM insulin (◨). Differences in the presence of ZAG are indicated as *** $p<0.001$.
Figure 2D:
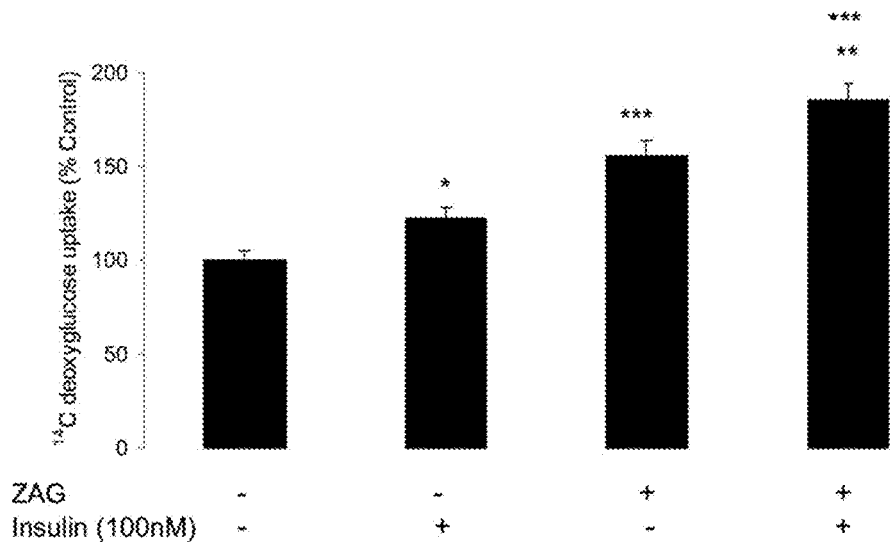
FIG. 2D is a graphical diagram showing uptake of 2-deoxy-D-glucose into gastrocnemius muscle of ob/ob mice treated with either ZAG or PBS for 5 days in the absence or presence of insulin (100 nM). Differences in the presence of insulin are shown as * p<0.05 or  p<0.01, while differences in the presence of ZAG are shown as * p<0.001.
Figure 2E:
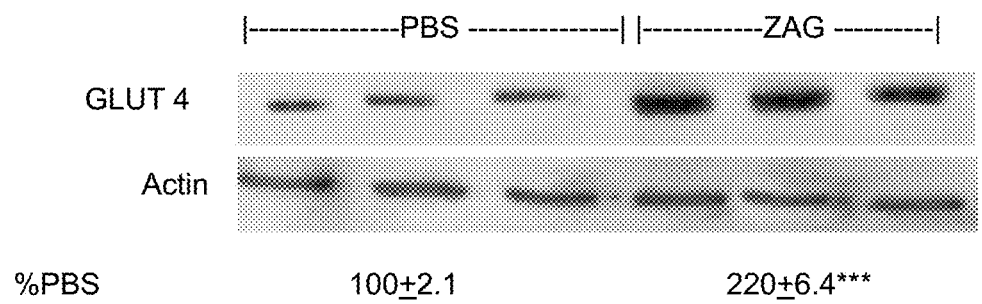
FIG. 2E is a pictorial diagram showing the effect of ZAG on the expression of GLUT4 glucose transporter in skeletal musclein of ob/ob mice. After treatment of ob/ob mice for 5 days skeletal muscle was removed and Western blotted for expression of GLUT4.

To investigate this, a glucose tolerance test was performed, on fed animals, after 3 days of ZAG administration (FIG. 2A). While blood glucose levels were significantly elevated in PBS controls, there was only a small rise in ZAG treated animals, which remained significantly below the control group throughout the course of the study. In addition plasma insulin levels were significantly lower in ZAG treated animals at the onset of the study and remained so during the 60 min of observation (FIG. 2B). ZAG administration increased glucose uptake into epididymal, visceral and subcutaneous adipocytes in the absence of insulin and also increased glucose uptake into epididymal and visceral adipocytes in the presence of low (1 nM) insulin (FIG. 2C). Glucose uptake into gastrocnemius muscle was also significantly enhanced in ZAG treated animals both in the absence and presence of insulin (100 nM) (FIG. 2D). The glucose uptake in gastrocnemius muscle of ZAG treated mice was greater than the response to insulin in non-treated animals.

Figure 3A:
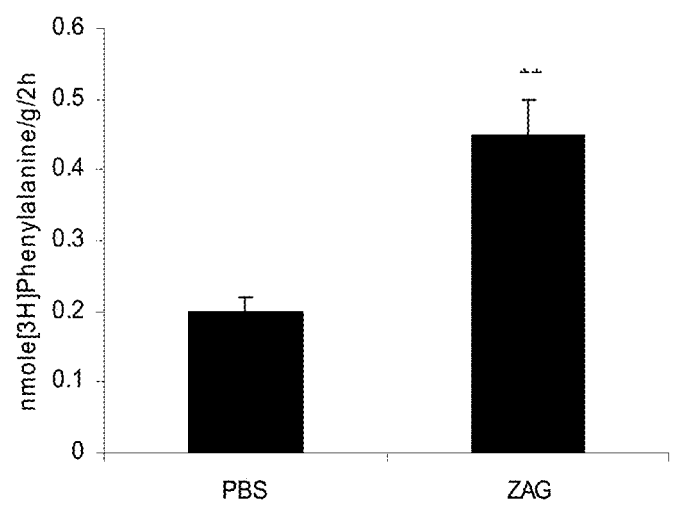
FIG. 3A is a graphical diagram showing the effect of ZAG on protein synthesis and degradation in skeletal muscle of ob/ob mice. After treatment of ob/ob mice for 5 days skeletal muscle was removed and used for the measurement of protein synthesis. Differences from PBS controls, or non-obese animals are shown as *** p<0.001.
Figure 3B:
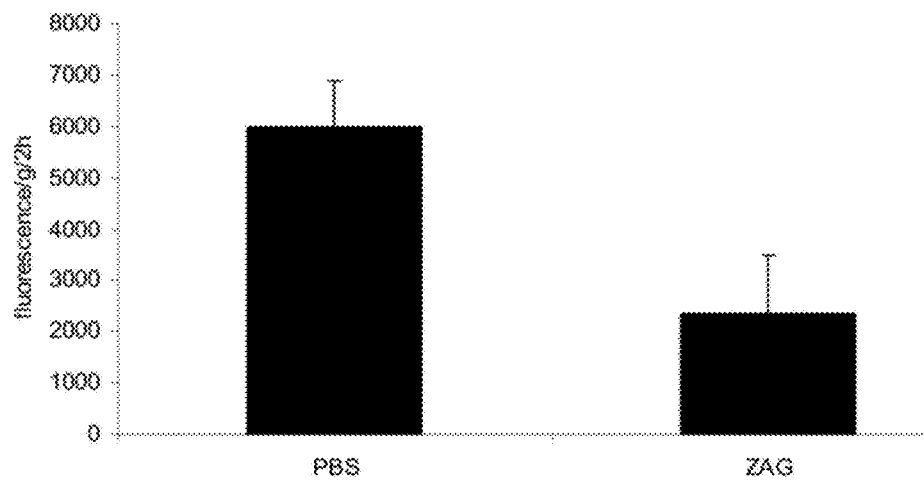
FIG. 3B is a graphical diagram showing the effect of ZAG on protein synthesis and degradation in skeletal muscle of ob/ob mice. After treatment of ob/ob mice for 5 days skeletal muscle was removed and used for the measurement of protein degradation. Differences from PBS controls, or non-obese animals are shown as *** p<0.001.
Figure 3C:
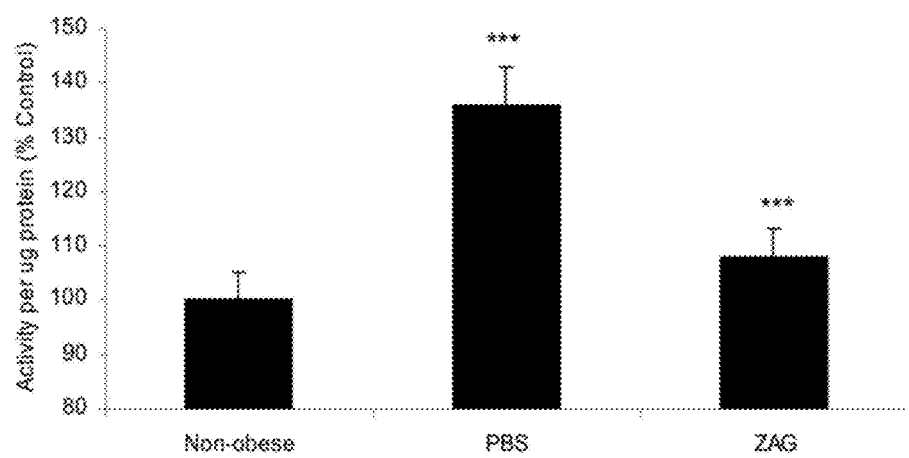
FIG. 3C is a graphical diagram showing the effect of ZAG on protein synthesis and degradation in skeletal muscle of ob/ob mice. After treatment of ob/ob mice for 5 days skeletal muscle was removed and used for the measurement of chymotrypsin-like enzyme activity. Differences from PBS controls, or non-obese animals are shown as *** p<0.001.
Figure 3D:
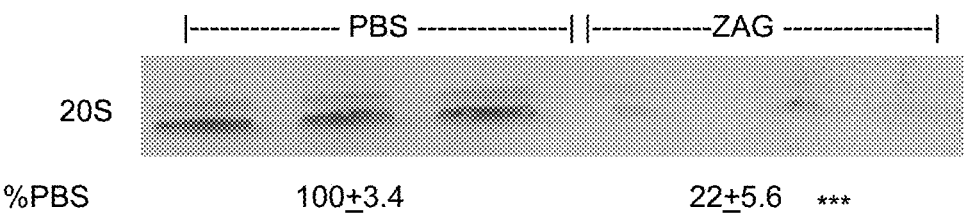
FIG. 3D is a pictorial diagram showing the effect of ZAG on protein synthesis and degradation in skeletal muscle of ob/ob mice. After treatment of ob/ob mice for 5 days skeletal muscle was removed and Western blotted for expression of 20S-proteasome $\alpha$-subunits.
Figure 3E:
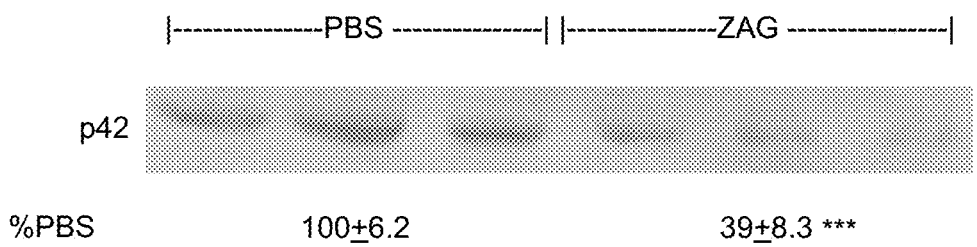
FIG. 3E is a pictorial diagram showing the effect of ZAG on signaling pathwasy in skeletal muscle of ob/ob mice. After treatment of ob/ob mice for 5 days skeletal muscle was removed and Western blotted for expression of p42.
Figure 3F:
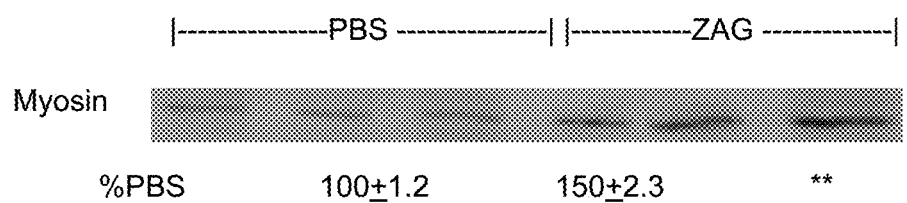
FIG. 3F is a pictorial diagram showing the effect of ZAG on protein synthesis and degradation in skeletal muscle of ob/ob mice. After treatment of ob/ob mice for 5 days skeletal muscle was removed and Western blotted for expression of myosin.
Figure 3G:
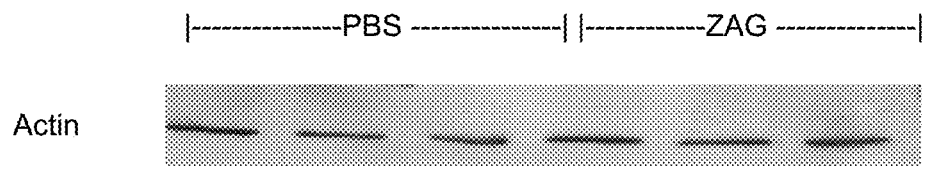
FIG. 3G is a pictorial diagram showing the effect of ZAG on protein synthesis and degradation in skeletal muscle of ob/ob mice. After treatment of ob/ob mice for 5 days skeletal muscle was removed and Western blotted for expression of actin as a control.
Figure 4A:
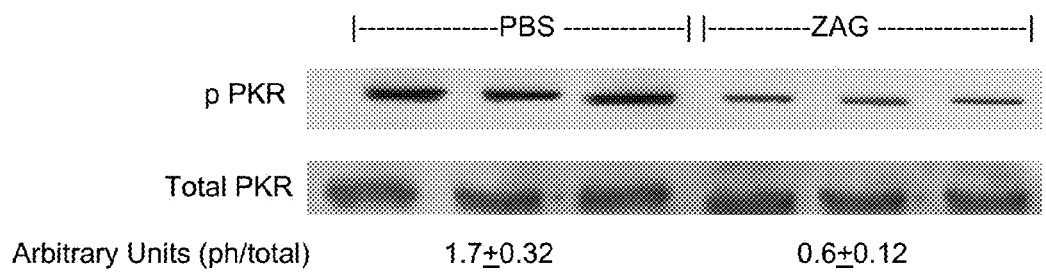
FIG. 4A is a pictorial diagram showing the effect of ZAG on catabolic signaling pathways in skeletal muscle by Western blotting of phospho PKR in gastrocnemius muscle of ob/ob mice after treatment with either PBS or ZAG for 5 days. The total forms of the proteins serve as loading controls. Differences from PBS controls are shown as *** p<0.001 while differences from non-obese mice are shown as # p<0.001.
Figure 4B:
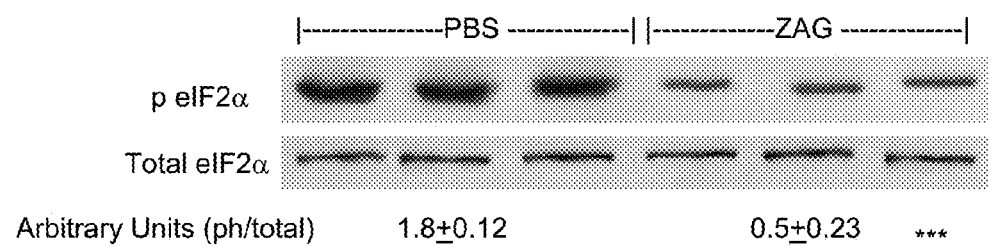
FIG. 4B is a pictorial diagram showing the effect of ZAG on catabolic signaling pathways in skeletal muscle by Western blotting of phospho eIF2a in gastrocnemius muscle of ob/ob mice after treatment with either PBS or ZAG for 5 days. The total forms of the proteins serve as loading controls. Differences from PBS controls are shown as *** p<0.001 while differences from non-obese mice are shown as # p<0.001.
Figure 4C:
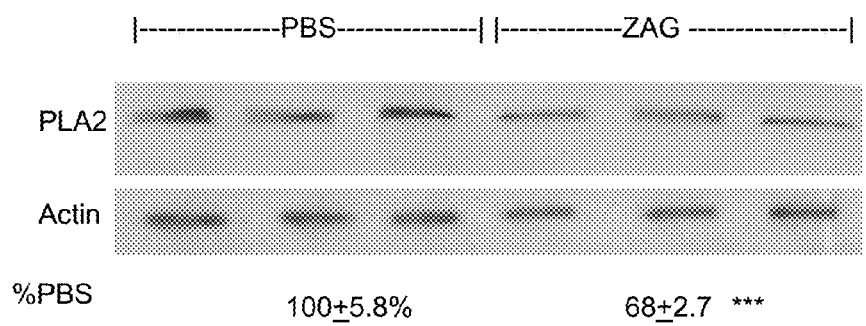
FIG. 4C is a pictorial diagram showing the effect of ZAG on catabolic signaling pathways in skeletal muscle by Western blotting of phospho PLA$_2$ in gastrocnemius muscle of ob/ob mice after treatment with either PBS or ZAG for 5 days. The total forms of the proteins serve as loading controls. Differences from PBS controls are shown as *** p<0.001 while differences from non-obese mice are shown as # p<0.001.
Figure 4D:
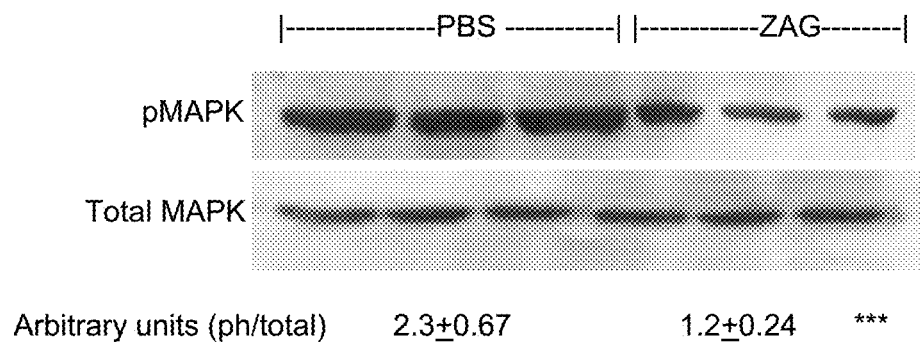
FIG. 4D is a pictorial diagram showing the effect of ZAG on catabolic signaling pathways in skeletal muscle by Western blotting of phospho p38MAPK in gastrocnemius muscle of ob/ob mice after treatment with either PBS or ZAG for 5 days. The total forms of the proteins serve as loading controls. Differences from PBS controls are shown as *** p<0.001 while differences from non-obese mice are shown as # p<0.001.
Figure 4E:
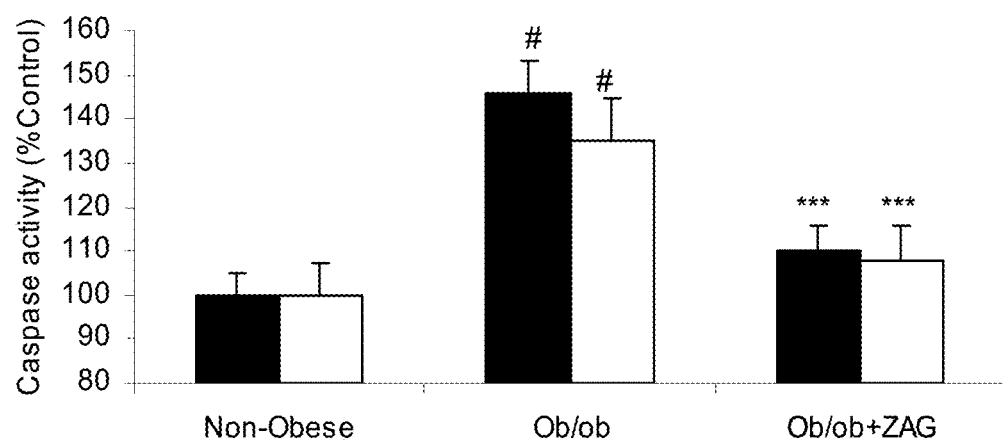
FIG. 4E is a graphical diagram showing the effect of ZAG on catabolic signaling pathways in skeletal muscle by activity of caspase-3 (■) and caspase-8 (□) in gastrocnemius muscle of ob/ob mice after treatment with either PBS or ZAG for 5 days.

ZAG administration also attenuated the effect of hyperglycemia on skeletal muscle atrophy. Thus ob/ob mice treated with ZAG showed a significant increase in the wet weight of both gastrocnemius and soleus muscles (Table 1). This was associated with over a two-fold increase in protein synthesis in soles muscle (FIG. 3A), and a 60% decrease in protein degradation (FIG. 3B). Gastrocnemius muscles from mice treated with ZAG showed a decreased activity of the proteasome 'chymotrypsin-like' enzyme activity (FIG. 3C), which was not significantly different from that found in non-obese mice, and a decreased expression of both the 20S proteasome α-subunits (FIG. 3D), and p42, an ATPase subunit of the 19S regulator (FIG. 3E), suggesting a reduced activity of the ubiquitin-proteasome pathway. Myosin levels were increased in ZAG-treated mice (FIG. 3F), while actin levels did not change (FIG. 3G). In addition there was a reduction in the level of phosphorylated forms of the dsRNA-dependent protein kinase (PKR) (FIG. 4A) and eukaryotic initiation factor 2α (eIF2α) (FIG. 4B), which have been shown to be responsible for muscle atrophy induced by tumor catabolic factors, and high levels of extracellular glucose. Other enzymes in this pathway including phospholipase $A_2$ ($PLA_2$) (FIG. 4C), p38 mitogen activated protein kinase (FIG. 4D) and caspases-3 and -8 (FIG. 4E) were also attenuated in gastrocnemius muscles of ob/ob mice treated with ZAG. These changes were commensurate with a decrease in catabolic signaling in muscle in response to ZAG.

Figure 5A:
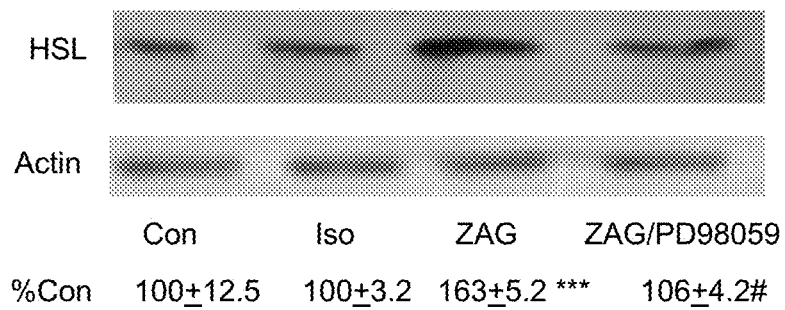
FIG. 5A is a pictorial diagram showing expression of HSL in response to ZAG. Western blots show expression of phospho HSL in adipocytes of non-obese mice 3 h after no treatment (Con), or treatment with isoprenaline (10 µM) or ZAG (0.46 µM) alone, or in the presence of PD98059 (25 µM) after 5 days treatment with ZAG.
Figure 5B:
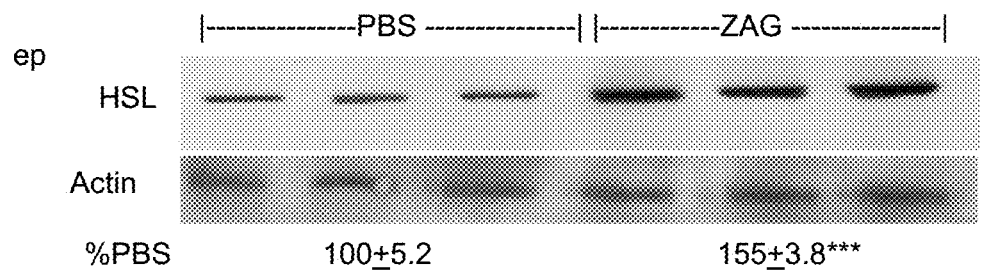
FIG. 5B is a pictorial diagram showing expression of HSL by immunoblotting in epididymal (ep) adipocytes after 5 days treatment with ZAG.
Figure 5C:
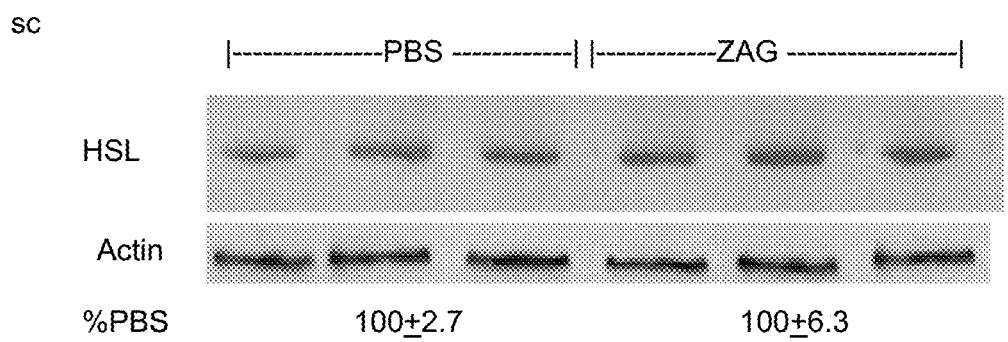
FIG. 5C is a pictorial diagram showing expression of HSL by immunoblotting in subcutaneous (sc) adipocytes after 5 days treatment with ZAG.
Figure 5D:
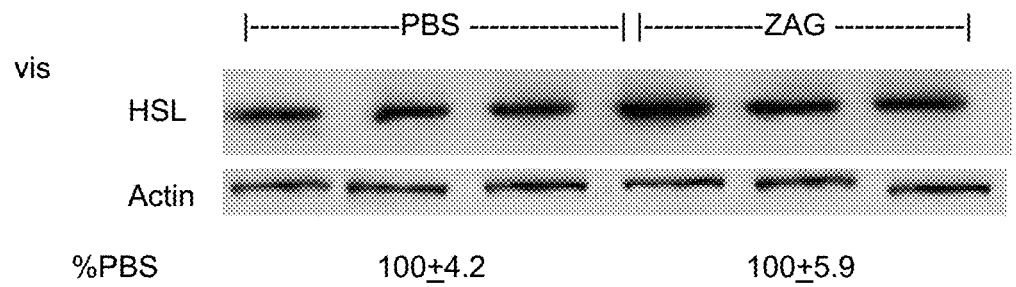
FIG. 5D is a pictorial diagram showing expression of HSL by immunoblotting in visceral (vis) adipocytes after 5 days treatment with ZAG.
Figure 5E:
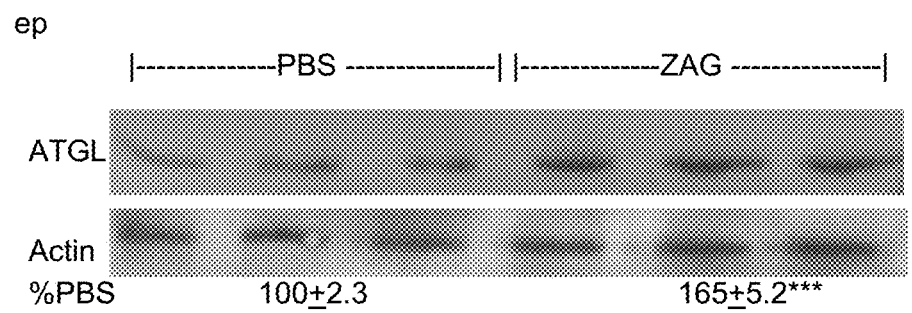
FIG. 5E is a pictorial diagram showing expression of ATGL in epididymal adipocytes after 5 days treatment with ZAG.
Figure 5F:
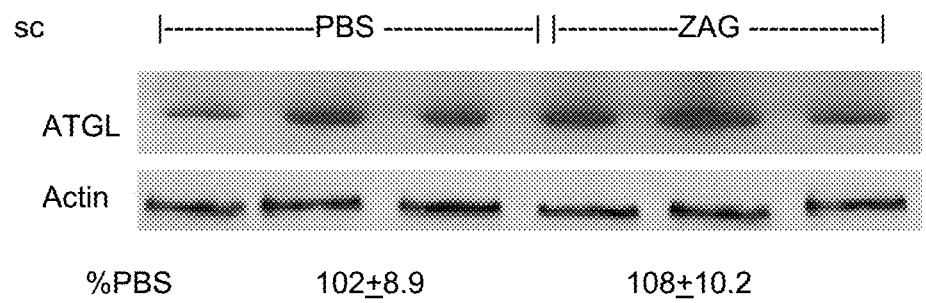
FIG. 5F is a pictorial diagram showing expression of ATGL in subcutaneous adipocytes after 5 days treatment with ZAG.
Figure 5G:
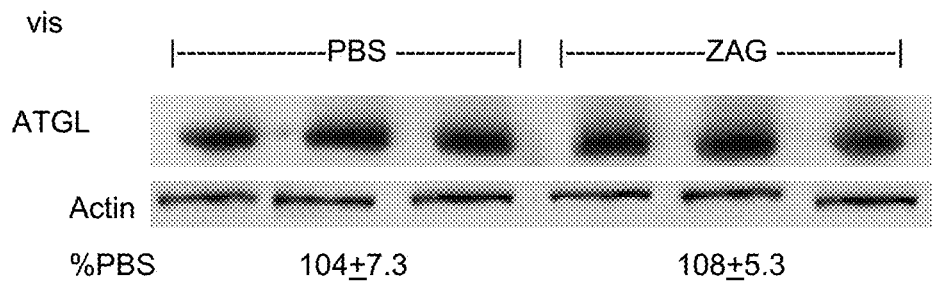
FIG. 5G is a pictorial diagram showing expression of ATGL in visceral adipocytes after 5 days treatment with ZAG.
Figure 5H:
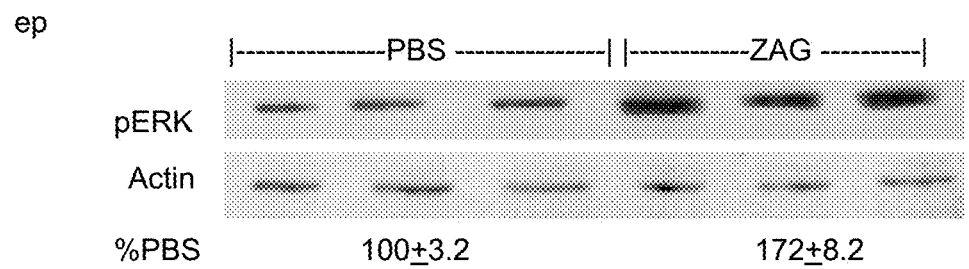
FIG. 5H is a pictorial diagram showing expression of pERK in epididymal adipocytes after 5 days treatment with ZAG.
Figure 5I:
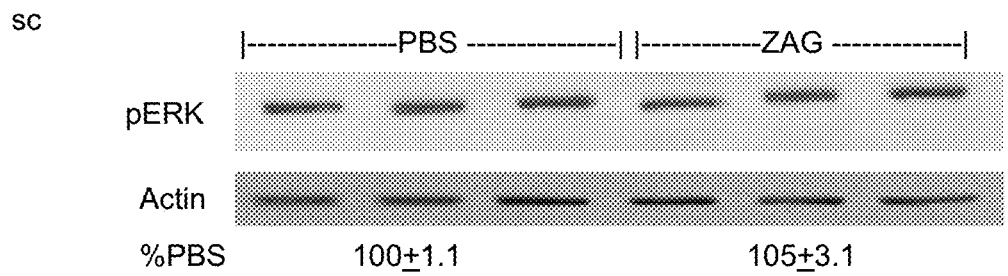
FIG. 5I is a pictorial diagram showing expression of pERK in subcutaneous adipocytes after 5 days treatment with ZAG.
Figure 5J:
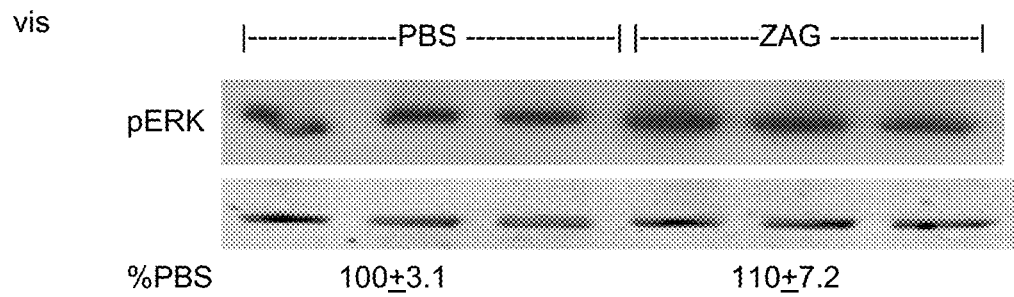
FIG. 5J is a pictorial diagram showing expression of pERK in visceral adipocytes after 5 days treatment with ZAG.
Figure 5K:
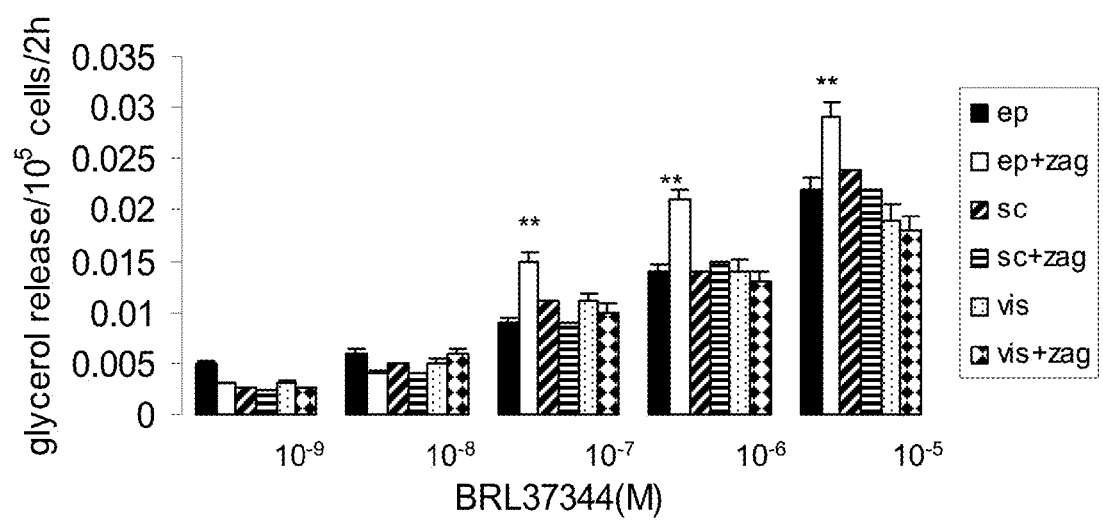
FIG. 5K is a graphical diagram showing the response of adipocytes from epididymal (ep), subcutaneous (sc) and visceral (vis) deposits from ob/ob mice treated with either PBS or ZAG for 5 days to the lipolytic effect of BRL37344. Differences from PBS controls are indicated as *** p<0.01, while differences in the presence of PD98059 is shown as # p<0.001.

ZAG, but not isoprenaline increased expression of phospho HSL in adipocytes which was completely attenuated by the extracellular signal-regulated kinase (ERK) inhibitor PD98059[14]. While ZAG increased expression of HSL in epididymal adipocytes there was no increase in either subcutaneous or visceral adipocytes (FIGS. 5B-5D). A similar situation was observed with expression of adipose triglyceride lipase (ATGL) (FIGS. 5E-5G). Expression of HSL and ATGL correlated with expression of the active (phospho) form of ERK (FIGS. 5H-5J). Expression of HSL and ATGL in epididymal adipocytes correlated with an increased lipolytic response to the β3 agonist, BRL37344 (FIG. 5K). This result suggests that ZAG may act synergistically with β3 agonists.

Figure 1G:
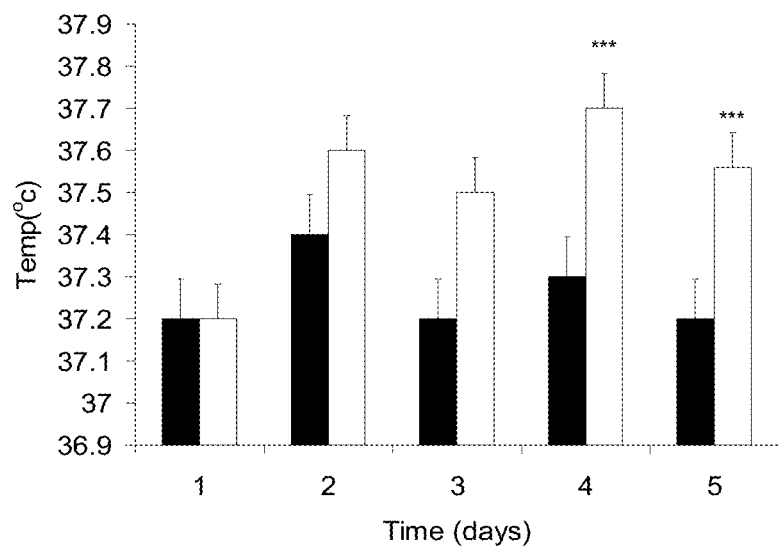
FIG. 1G is a graphical diagram showing the effect of ZAG (□) on body temperature of the mice shown in e in comparison with PBS controls (■). Differences from control are shown as *** $p<0.001$.
Figure 6A:
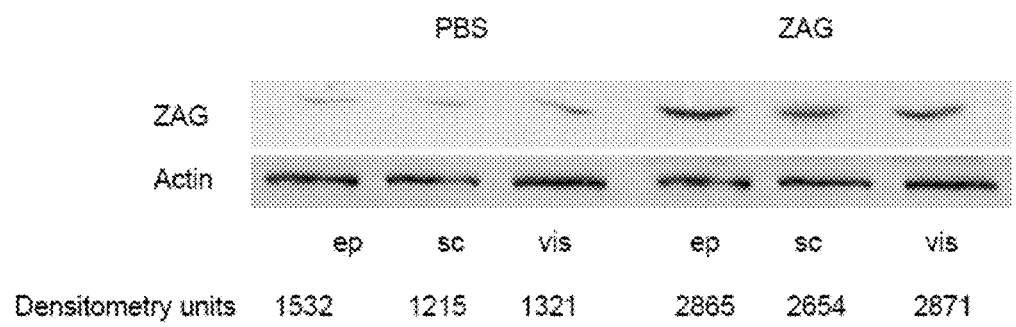
FIG. 6A is a pictorial diagram showing the Effect of treatment of ob/ob mice for 5 days with ZAG on the expression of ZAG in WAT. Western blot showing expression of ZAG in ep, sc, and vis adipocytes. Day 0 represents the day the adipocytes were removed from the mice.
Figure 6B:
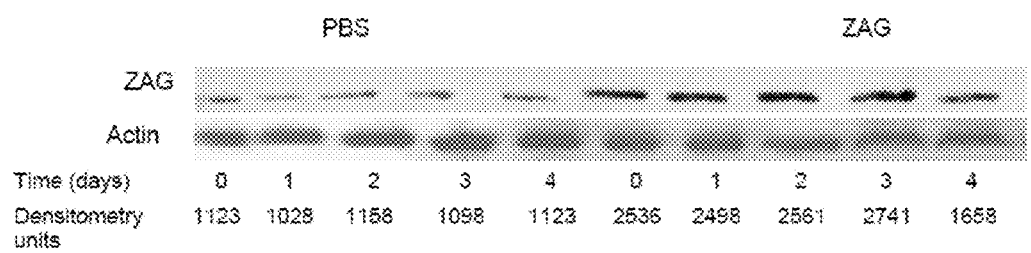
FIG. 6B is a pictorial diagram showing expression of ZAG in epididymal adipocytes that were suspended in RMPI medium as described in methods. The samples were then taken out at daily intervals and Western blotted for ZAG expression. Day 0 represents the day the adipocytes were removed from the mice.
Figure 6C:
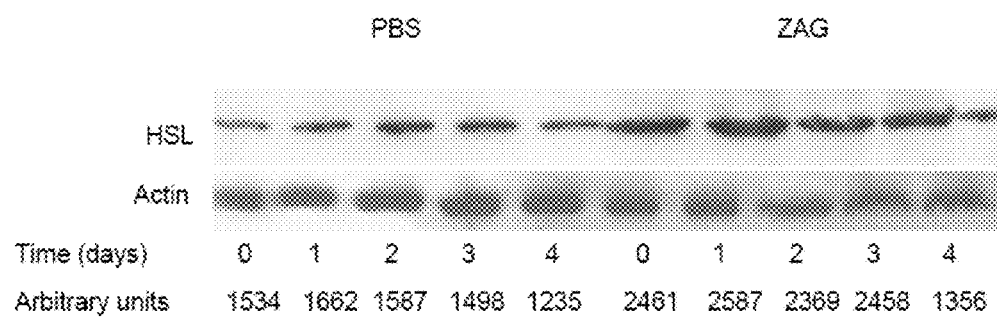
FIG. 6C is a pictorial diagram showing expression of HSL in epididymal adipocytes that were suspended in RMPI medium as described in methods. The samples were then taken out at daily intervals and Western blotted for HSL expression. Day 0 represents the day the adipocytes were removed from the mice.
Figure 6D:
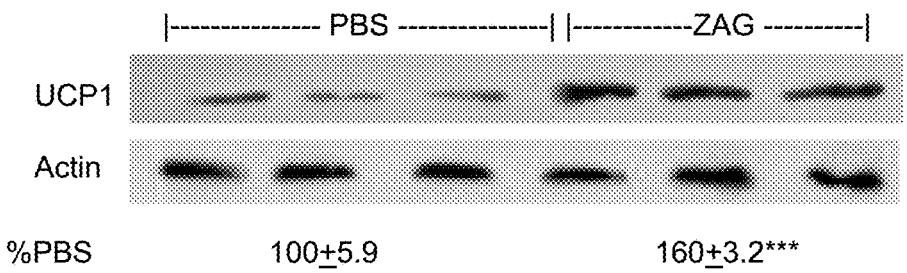
FIG. 6D is a pictorial diagram showing expression of UCP1 in BAT removed from mice. Differences from PBS treated mice are shown as *** p<0.001.
Figure 6E:
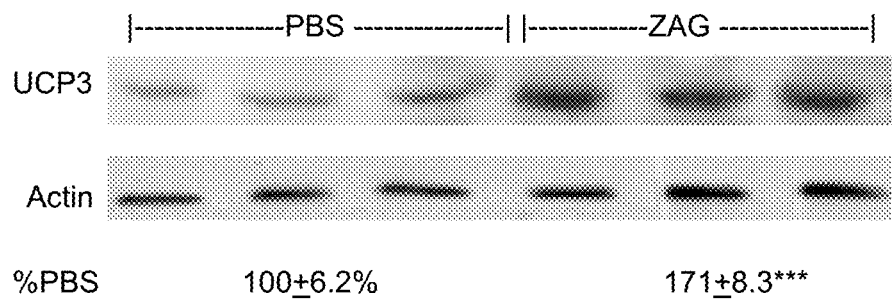
FIG. 6E is a pictorial diagram showing expression of UCP3 in BAT removed from mice. Differences from PBS treated mice are shown as *** p<0.001.
Figure 6F:
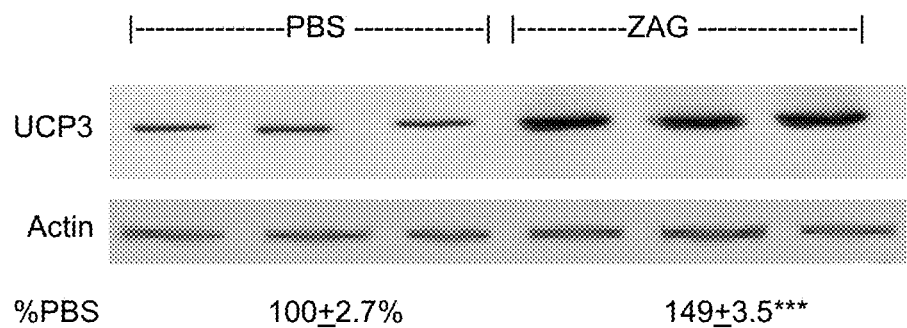
FIG. 6F is a pictorial diagram showing expression of UCP3 in gastrocnemius muscle removed from mice. Differences from PBS treated mice are shown as *** p<0.001.

As previously reported, ZAG administration increased its expression in adipose tissue (FIG. 6A). ZAG expression remained elevated, for a further 3 days in tissue culture in the absence of ZAG (FIG. 6B). Expression of HSL was also elevated in adipocytes for 3 days in tissue culture in the absence of ZAG (FIG. 6C). Administration of ZAG increased the expression of UCP1 (FIG. 6D) and UCP3 (FIG. 6E) in BAT (FIG. 6D) and UCP3 in skeletal muscle (FIG. 6F). An increased expression of uncoupling proteins would be expected to channel metabolic substrates into heat as observed (FIG. 1G).

After 21 days, the plasma metabolite levels in the ob/ob mice were observed (Table 2), with monitored parameters shown in Table 3. A further drop in blood glucose (from 2.03 to 15.2 mM) and a rise in glycerol were observed, which seems greater since the control is lower than before. No change in NEFA, TG or insulin was observed at Day 21, as compared to Day 5 (Table 1). It was noted that there is much more insulin in the pancreas in ZAG treated animals showing the drop in plasma insulin, which is not due to lower insulin production (e.g., as would happen with a toxin to pancreatic beta cells), but rather due to the fact that less insulin is needed to control blood glucose in the ZAG treated animals.

TABLE 2

Plasma metabolite and insulin levels in ob/ob mice treated with ZAG at Day 21.

|  | PBS | ZAG |  |
|---|---|---|---|
| Glucose (mmol/l) | 24.1 ± 2.3 | 15.2 ± 2.1 | p = 0.0085 |
| NEFA(mEq/l) | 0.62 ± 0.008 | 0.22 ± 0.06 | p = 0.0025 |
| Glycerol | 290 ± 25.2 | 450 ± 36.2 | p = 0.0058 |
| Triglycerides (mmol/l) | 1.72 ± 0.05 | 0.89 ± 0.08 | p = 0.0072 |
| Insulin (ng/ml) | 39.5 ± 0.96 | 28.5 ± 0.34 | p = 0.0056 |

TABLE 2-continued

Plasma metabolite and insulin levels in ob/ob
mice treated with ZAG at Day 21.

|  | PBS | ZAG |  |
|---|---|---|---|
| Insulin Pancreas (pg/g pancerase) | 6.2 ± 3.2 | 14.5 ± 2.5 | p = 0.0035 |

TABLE 3

Parameters monitored in ob/ob mice treated with ZAG at Day 21.

| Parameter | PBS | ZAG | p |
|---|---|---|---|
| Start weight | 92.5 ± 3.1 | 93.1 ± 1.9 |  |
| Finish weight | 89.9 ± 1.3 | 83.95 ± 2.2 |  |
| Food (g) | 135 ± 6 | 145 ± 4 |  |
| Water (ml) | 268 ± 15 | 259 ± 20 |  |
| BAT (g) | 0.36 ± 0.21 | 0.41 ± 0.35 |  |
| Gastrocnemius (g) | 0.26 ± 0.15 | 0.39 ± 0.12 | 0.01 |
| Soleus (g) | 0.15 ± 0.06 | 0.18 ± 0.07 |  |

Figure 7A:
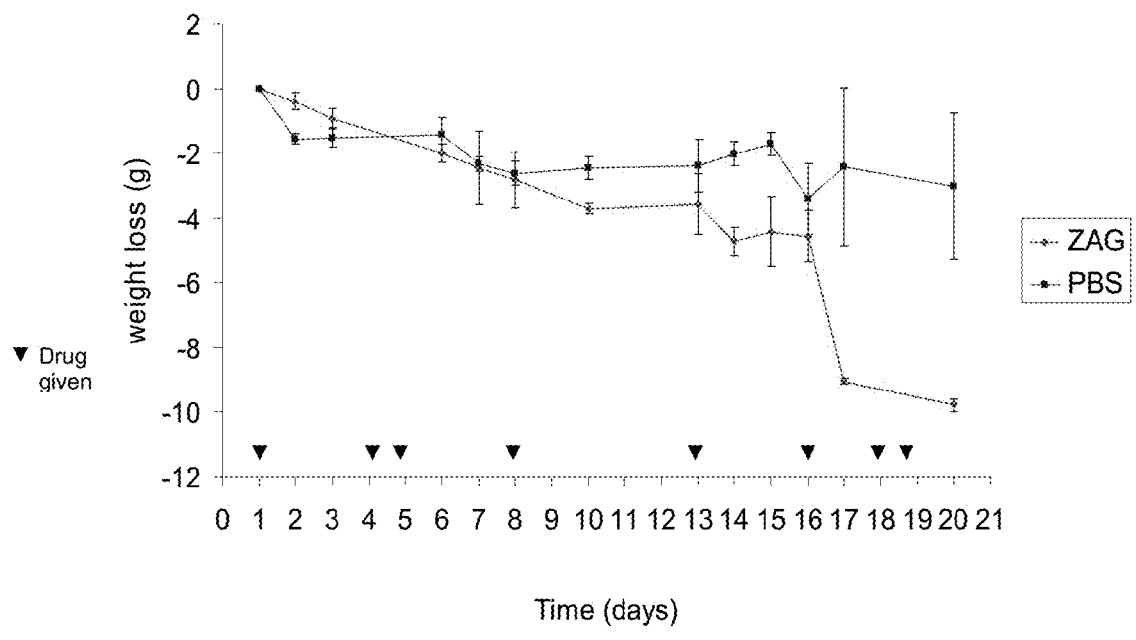
FIG. 7A is a graphical diagram showing weight loss of the ob/ob mice during the 21 day study. ZAG was injected at days 1, 4, 5, 8, 13, 16, 18, and 19; PBS was injected at the same time points.
Figure 7B:
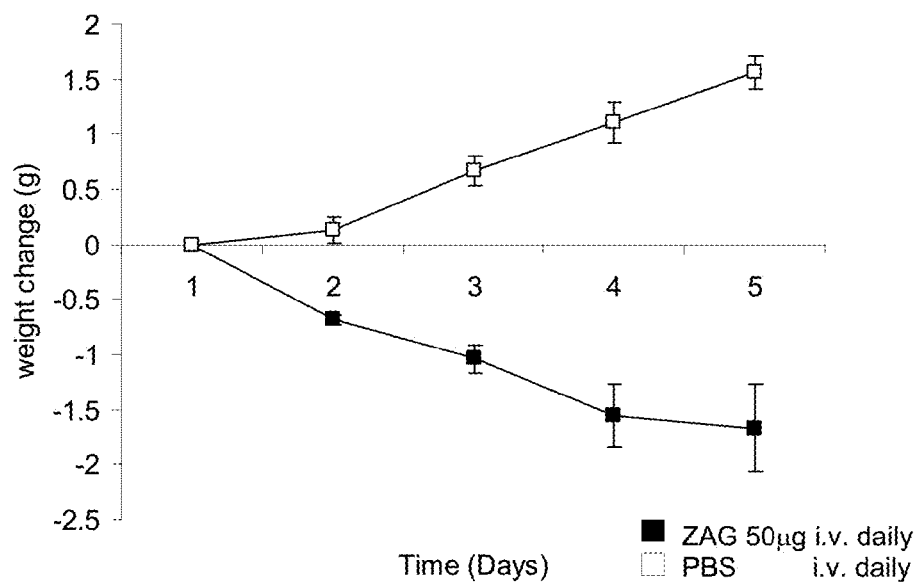
FIG. 7B is a graphical diagram showing weight change (g) of the ob/ob mice (weight 80-90 g) during treatment with ZAG.
Figure 7C:
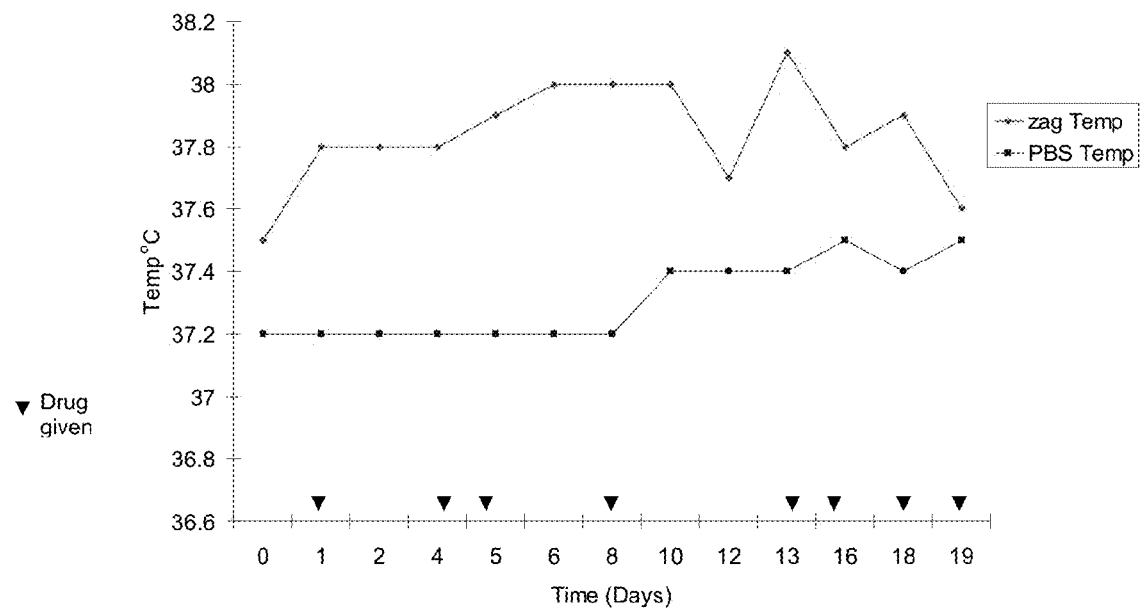
FIG. 7C is a graphical diagram showing increased body temperature of the ob/ob mice during the 21 day study. ZAG was injected at days 1, 4, 5, 8, 13, 16, 18, and 19; PBS was injected at the same time points.
Figure 8A:
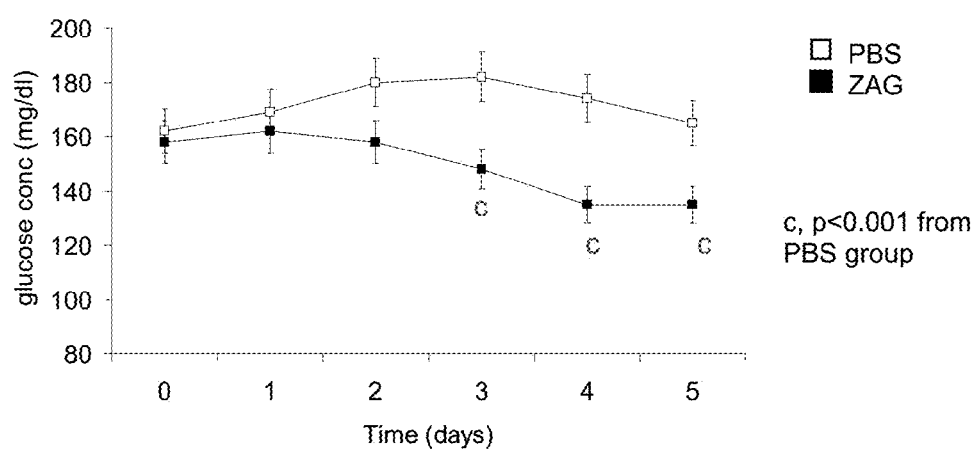
FIG. 8A is a graphical diagram showing a progressive decrease in urinary glucose excretion during the first 5 days of treatment.
Figure 8B:
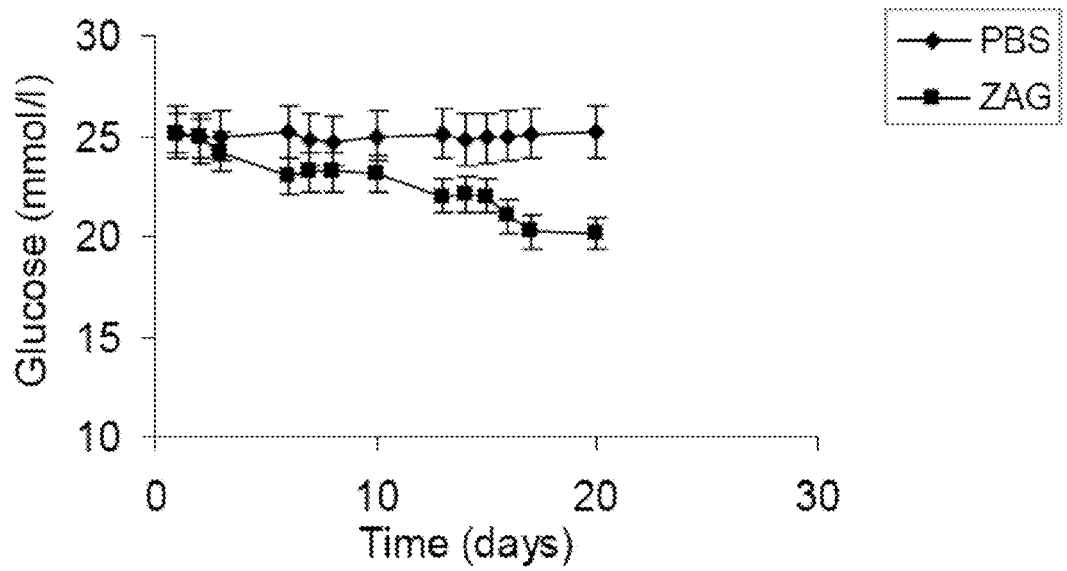
FIG. 8B is a graphical diagram showing a progressive decrease in urinary glucose excretion during the 21 day study.

In addition, body temperature of the ob/ob mice increased 0.5° to 1° C. (FIG. 1G) within four days and peaked at 38.1° C. (FIG. 7) just before they lost the maximum amount of weight. This would correlate with the weight of brown adipose tissue which increases from 0.33±0.12 g in the control to 0.52±0.08 g in the ZAG treated animals (FIG. 7). The weight of the gastrocnemius muscles was also increased from 0.2±0.05 g to 0.7±0.1 g, while there was a progressive decrease in urinary glucose excretion (FIGS. 8A and 8B).

Figure 11:
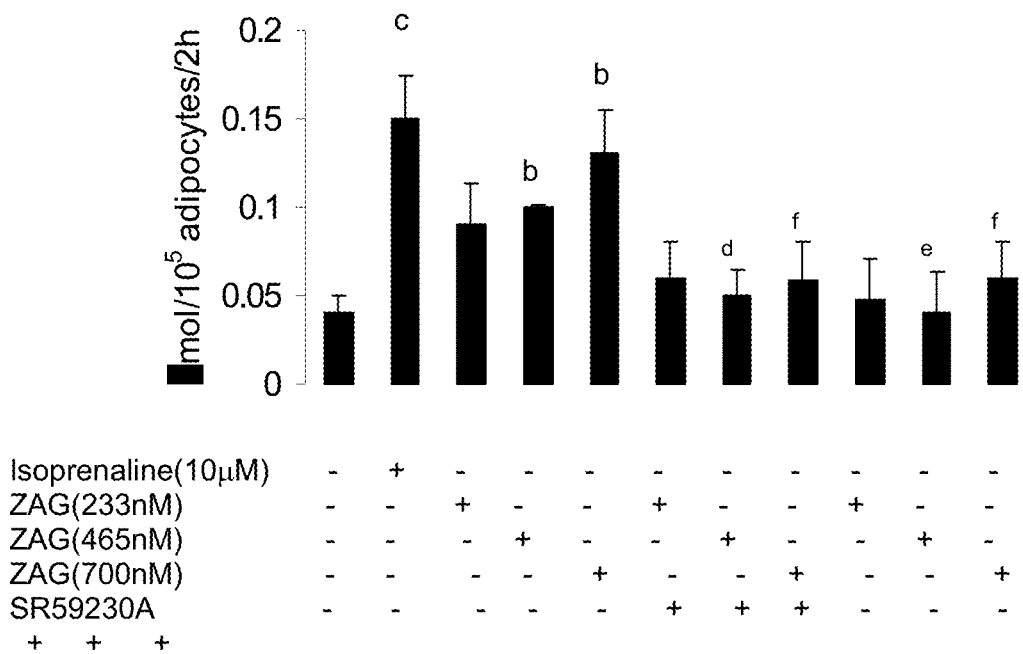
FIG. 11 is a graphical diagram showing lipolytic activity of human ZAG in isolated rat epididymal adipocytes, compared with isoprenaline (10 µM) in the absence or presence of SR59230A (10 µM) or anti-ZAG antibody (1:1000) (IgG). Each value is an average of 5 separate studies. Differences from control are shown as b, p<0.01 or c, p<0.001, while differences from ZAG alone are indicated as e, p<0.01 or f, p<0.001.

Results—Rats. The lipolytic effect of human ZAG towards rat epididymal adipocytes in comparison with isoprenaline is shown in FIG. 11. At concentrations between 233 and 700 nM ZAG produced a dose-related increase in glycerol release, which was attenuated by anti-ZAG monoclonal antibody, showing the specificity of the action. The extent of lipolysis in rat adipocytes was similar to that previously reported in the mouse. As in the mouse, the lipolytic effect of ZAG was completely attenuated by the β3-adrenergic receptor (β3-AR) antagonist SR59230A, suggesting that the action of ZAG was mediated through β3-AR. These results suggest that ZAG may be effective in inducing fat loss in rats.

Figure 12A:
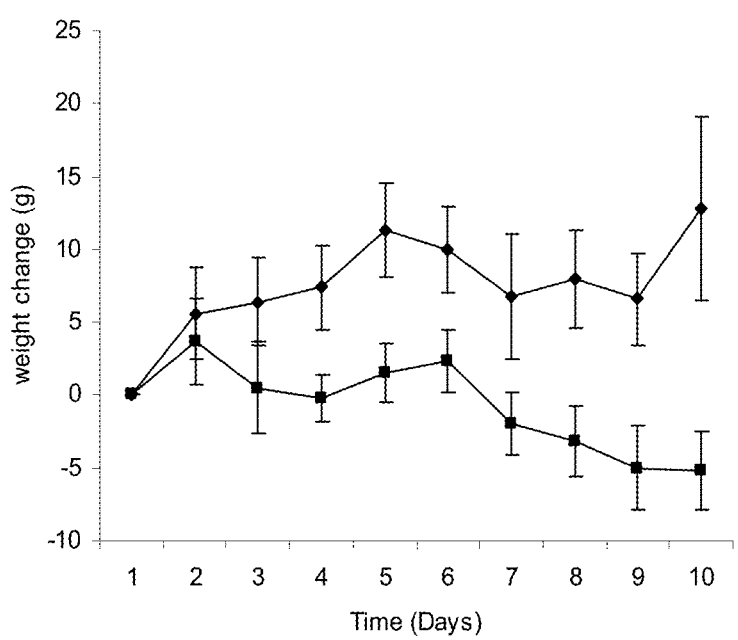
FIG. 12A is a graphical diagram showing the effect of daily i.v. administration of either ZAG (50 µg/100 g b.w.) in 100 µl PBS (■) or PBS alone (♦) on body weight of male Wistar rats over a 10 day period. The protocol for the experiment is given in the methods section.
Figure 12B:
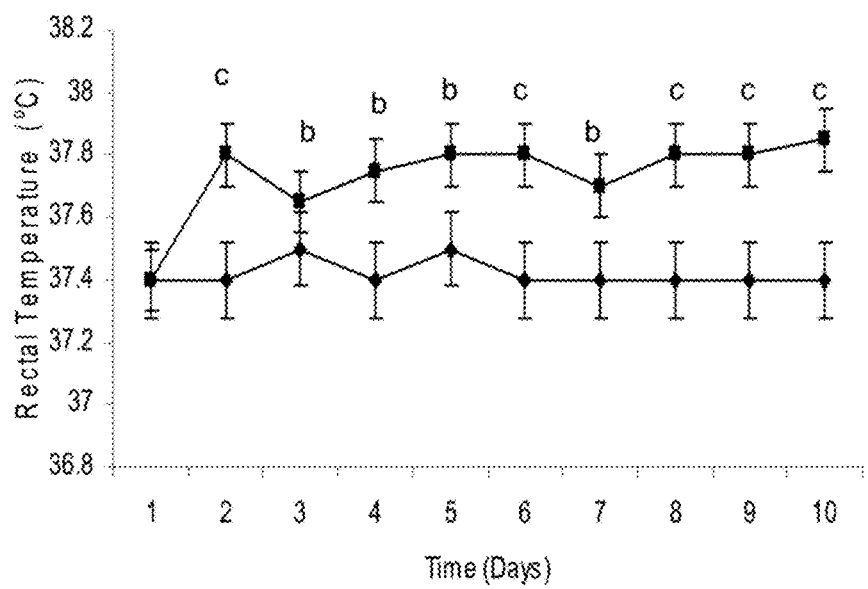
FIG. 12B is a graphical diagram showing the body temperature of male Wistar rats administered either ZAG (■) or PBS (♦) as described in FIG. 12A.
Figure 12C:
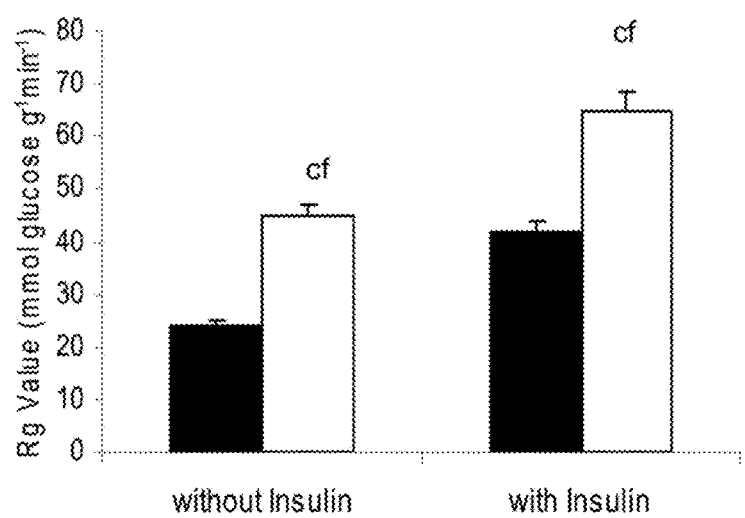
FIG. 12C is a graphical diagram showing the uptake of 2-deoxy-D-glucose into epididymal adipocytes of male Wistar rats after 10 days treatment with either ZAG (open box) or PBS (closed box) for 10 days, as shown in FIG. 12A, in the absence or presence of insulin (60 µU/ml).
Figure 12D:
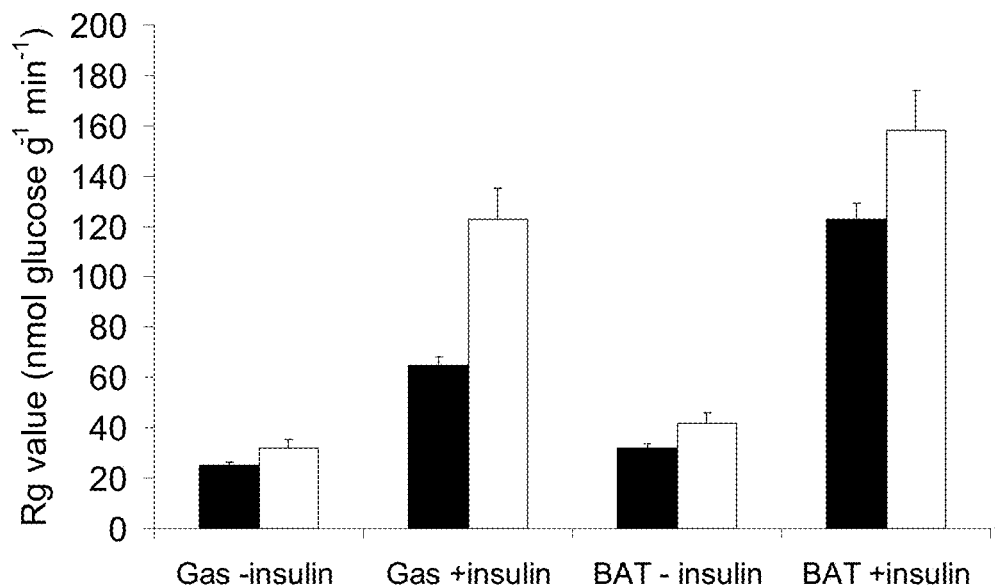
FIG. 12D is a graphical diagram showing glucose uptake into gastrocnemius muscle and BAT of male Wistar rats after 10 days treatment with either ZAG or PBS, in the absence or presence of insulin (60 µU/ml). Differences between ZAG and PBS treated animals are shown as a, p<0.05, b, p<0.01 or c, p<0.001, while differences in the presence of insulin are shown as or f, p<0.001.
Figure 12E:
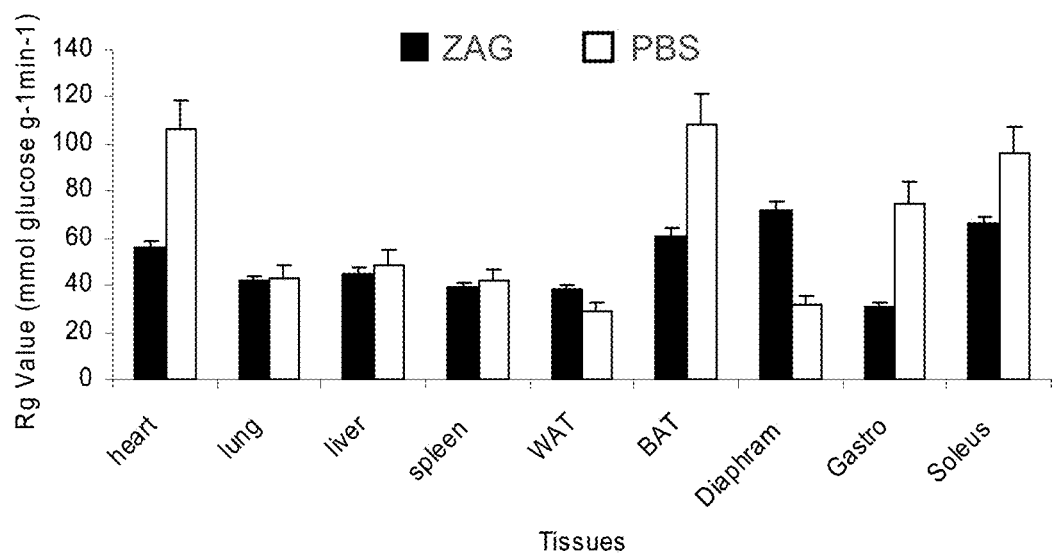
FIG. 12E is a graphical diagraph showing tissue Rg in ob/ob mice administered ZAG. c, p<0.001 from PBS.
Figure 13A:
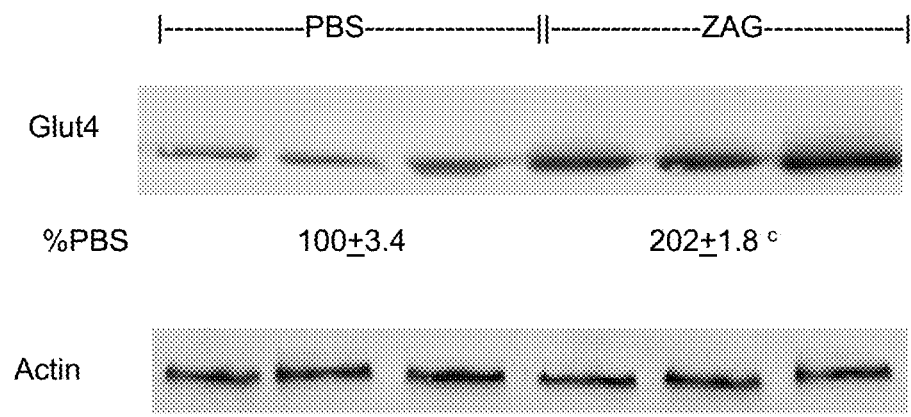
FIGS. 13A-13C are pictorial diagrams of Western blots showing expression of GLUT4 in BAT (FIG. 13A) and WAT (FIG. 13B) and gastrocnemius muscle (FIG. 13C) of male Wistar rats treated with either PBS or ZAG for 10 days as shown in FIG. 12. Differences between ZAG and PBS treated animals are shown as c, p<0.001.
Figure 13B:
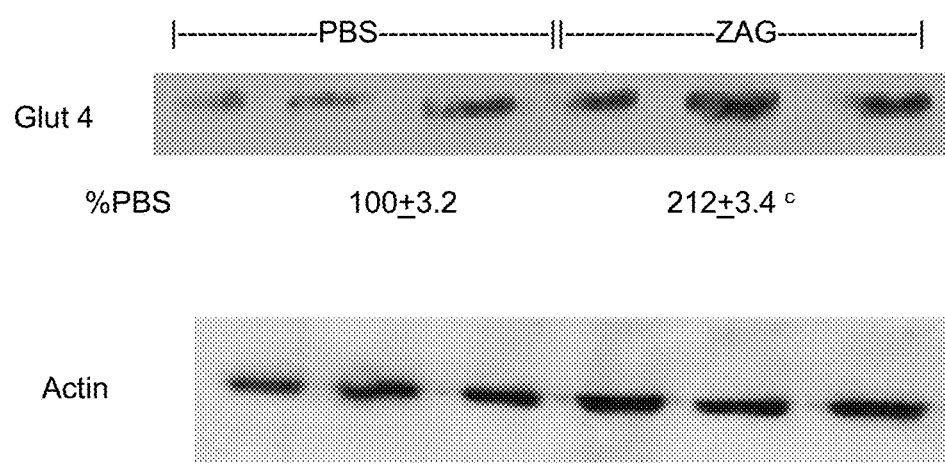
Figure 13C:
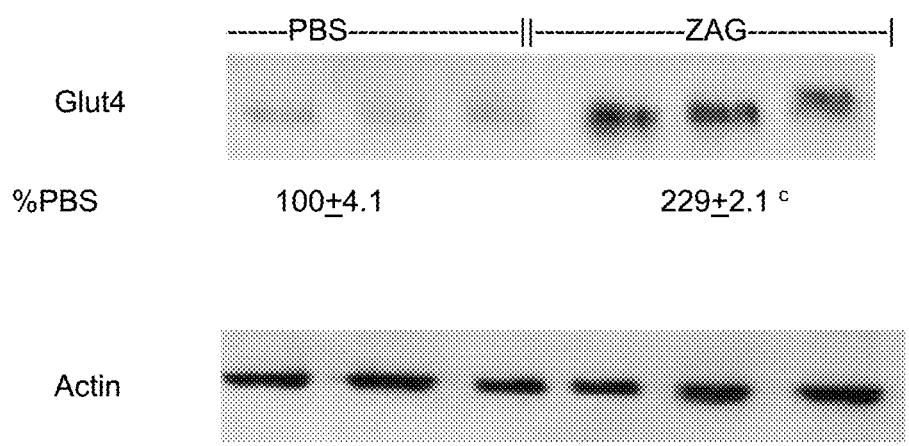
Figure 14A:
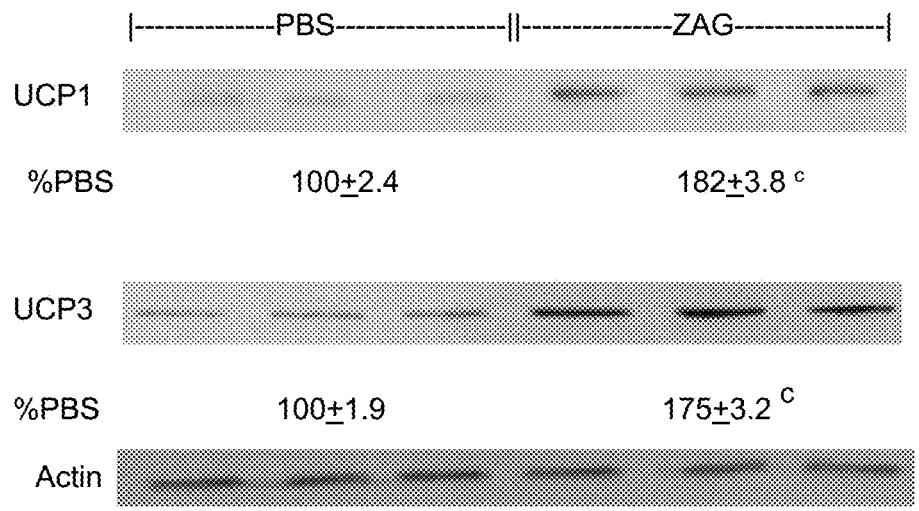
FIGS. 14A and 14B are pictorial diagrams of Western blots showing expression of UCP1 and UCP3 in BAT (FIG. 14A) and WAT (FIG. 14B) of male Wistar rats treated with either PBS or ZAG for 10 days as shown in FIG. 12. Differences between ZAG and PBS treated animals are shown as c, p<0.001.
Figure 14B:
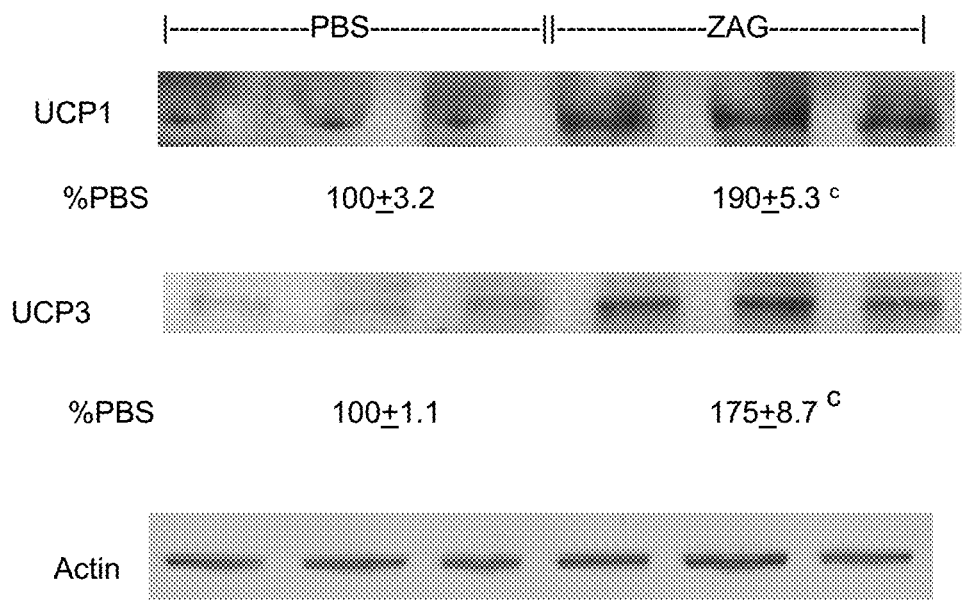

The effect of single daily i.v. injection of ZAG (50 μg/100 g b.w.) on the body weight of mature male Wistar rats (540±83 g) is shown in FIG. 12A. Compared with control rats administered the same volume of solvent (PBS), rats administered ZAG showed a progressive decrease in body weight, such that after 10 days, while rats treated with PBS showed a 13 g increase in body weight, animals treated with ZAG showed a 5 g decrease in body weight (Table 4). There was no difference in food (ZAG: 102±32 g; PBS:98±25 g) or water (ZAG: 135±35 ml; PBS: 125±25 ml) intake between the two groups during the course of the study, but ZAG-treated animals showed a consistent 0.4° C. elevation in body temperature, which was significant within 24 h of the first administration of ZAG (FIG. 12B), indicating an elevated energy expenditure. Body composition analysis (Table 4) showed that the loss of body weight induced by ZAG was due to a loss of carcass fat, which was partially offset by a significant increase in lean body mass. There was a 50% increase in plasma glycerol concentration in rats treated with ZAG (Table 5), indicative of an increased lipolysis, but a 55% decrease in plasma levels of nonesterified fatty acids (NEFA), suggesting an increased utilisation. Plasma levels of glucose and triglycerides were also reduced by 36-37% (Table 5), also suggesting an increased utilization. There was a significant increase in the uptake of 2-deoxygluocse into epididymal adipocytes of rats treated with ZAG for 10 days, which was increased in the presence of insulin (FIG. 12C). However, there was no significant difference in glucose uptake into adipocytes from ZAG or PBS treated animals in the presence of insulin (FIG. 12C). There was a small, non-significant increase in glucose uptake into gastrocnemius muscle and BAT of rats treated with ZAG in comparison with PBS controls, but a significant increase in uptake in the presence of insulin (FIG. 12D). These results suggest that the decrease in blood glucose is due to increased utilization by BAT, WAT and skeletal muscle, and this is supported by an increased expression of glucose transporter 4 (GLUT4) in all three tissues (FIG. 13).

TABLE 4

Body composition of male rats after treatment with either PBS or ZAG

| Treatment | Starting weight (g) | Final weight (g) | Weight change (g) | Water (g) | Water (%) | Fat (g) | Fat (%) | Non fat (g) | Non fat (%) |
|---|---|---|---|---|---|---|---|---|---|
| PBS | 510 ± 30 | 523 ± 2 | +13 ± 3 | 326 ± 32 | 62 ± 2 | 105 ± 14 | 20 ± 3 | 90 ± 6 | 17 ± 3 |
| ZAG | 530 ± 45 | 525 ± 1 | −5 ± 1 | 331 ± 5 | 63 ± 3 | 92 ± 5$^b$ | 18 ± 1 | 96 ± 2$^a$ | 18 ± 2 |

Differences from animals treated with PBS are shown as
$^a$p < 0.05 or
$^b$p < 0.01

TABLE 5

Plasma metabolite and insulin levels in rats treated with either PBS or ZAG for 10 days

| Metabolite | PBS | ZAG |
|---|---|---|
| Glucose (mmol/l) | 25.5 ± 2.3 | 16.2 ± 2.1$^c$ |
| Trigylcerides (mmol/l) | 1.75 ± 0.01 | 1.1 ± 0.09$^a$ |
| Glycerol (umol/l) | 300 ± 52 | 450 ± 51$^c$ |
| NEFA (mEq/l) | 0.58 ± 0.008 | 0.26 ± 0.06$^b$ |

Differences from animals treated with PBS are shown as either $^a$p < 0.05; $^b$p < 0.01 or $^c$p < 0.001

Figure 15A:
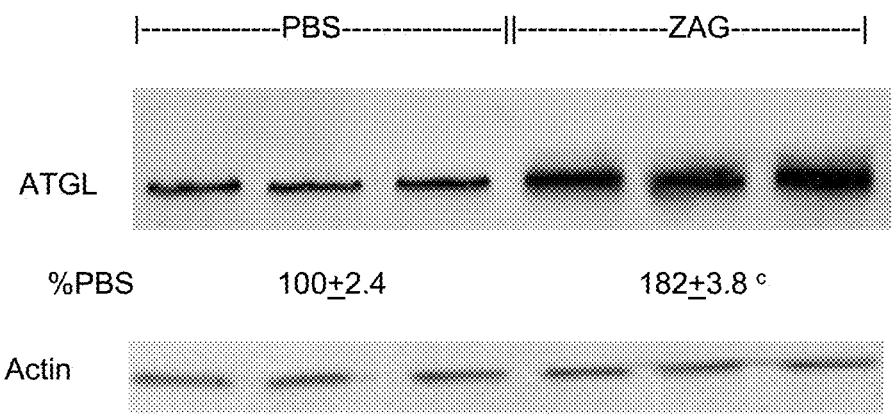
FIGS. 15A and 15B are pictorial diagrams of Western blots showing expression of ATGL (FIG. 15A) and HSL (FIG. 15B) in epididymal adipose tissue of male Wistar rats treated with either PBS or ZAG for 10 days as shown in FIG. 12. Differences between ZAG and PBS treated animals are shown as c, p<0.001.
Figure 15B:
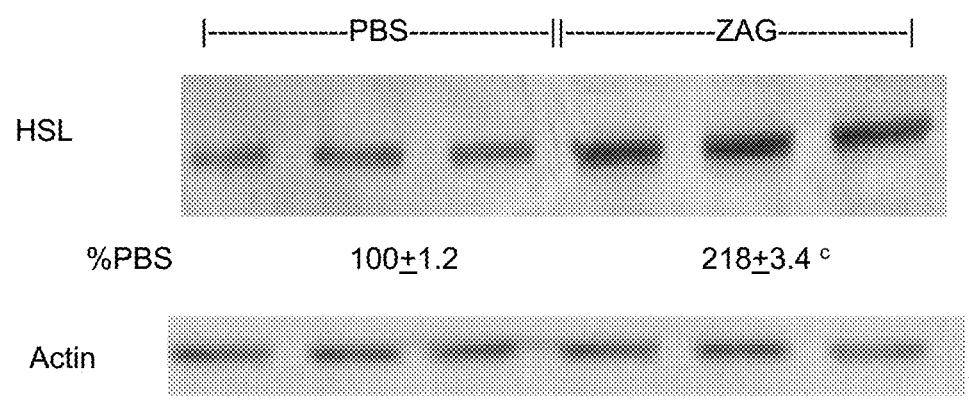
Figure 16A:
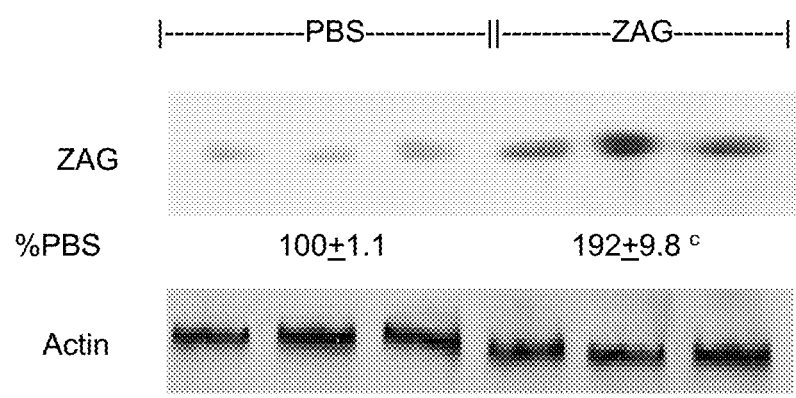
FIGS. 16A-16C are pictorial diagrams of Western blots showing expression of ZAG in gastrocnemius muscle (FIG. 16A), WAT (FIG. 16B) and BAT (FIG. 16C). Tissues were excised from male Wistar rats treated with either PBS or ZAG for 10 days as shown in FIG. 12. Differences between ZAG and PBS treated animals are shown as c, p<0.001.
Figure 16B:
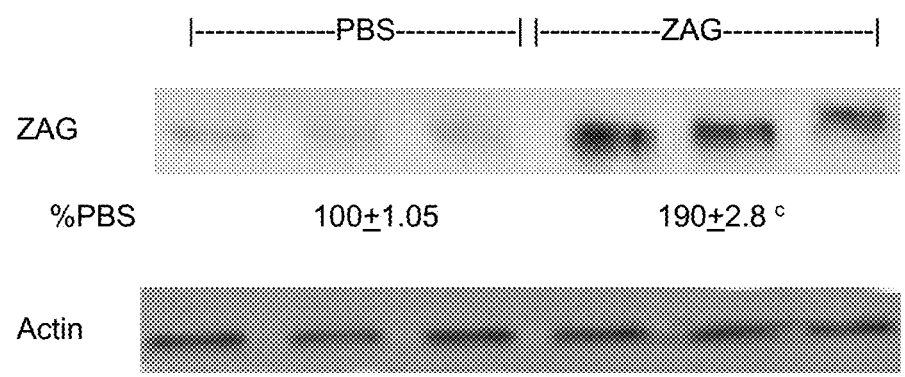
Figure 16C:
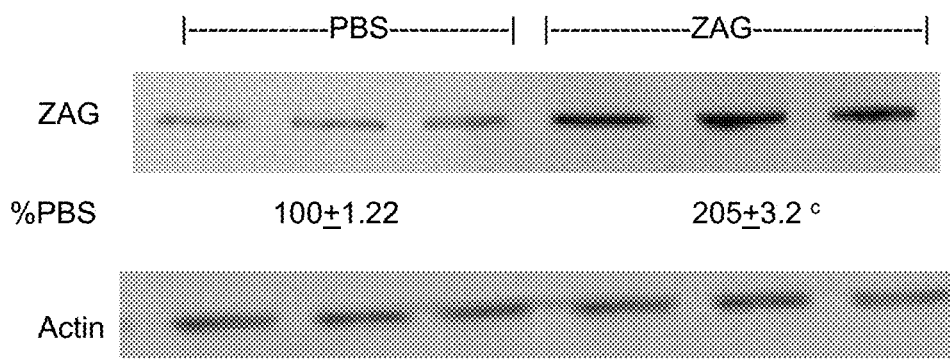

ZAG administration increased expression of the uncoupling proteins (UCP)-1 and -3 in both BAT and WAT by almost two-fold (FIGS. 13A and 13B), which would contribute to increased substrate utilization. In rats treated with ZAG there was also an increased expression of the lipolytic enzymes adipose triglyceride lipase (ATGL) and hormone sensitive lipase (HSL) in epididymal adipose tissue (FIG. 15), again with a two-fold increase. ATGL is mainly responsible for the hydrolysis of the first ester bond in a triacylglycerol molecule forming diacylgylcerol, while its conversion to monacylgylcerol is carried out by HSL. Expression of ZAG was also significantly increased in skeletal muscle, (FIG. 16A), WAT (FIG. 16B) and BAT (FIG. 16C) of rats treated with ZAG for 10 days, showing that exogenous ZAG boosts its own production in peripheral tissues.

Figure 17A:
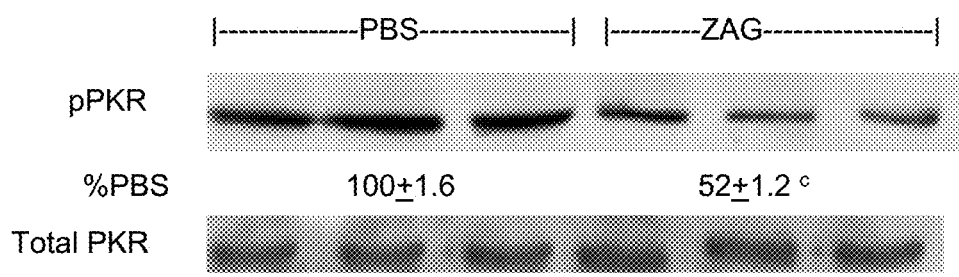
FIGS. 17A and 17B are pictorial diagrams of Western blots showing expression of phosphorylated and total forms of pPKR (FIG. 17A) and peIF2α (FIG. 17B) in gastrocnemius muscle of male Wistar rats treated with either PBS or ZAG for 10 days as shown in FIG. 12. The densitometric analysis is the ratio of the phosphor to total forms, expressed as a percentage of the value for rats treated with PBS.
Figure 17B:
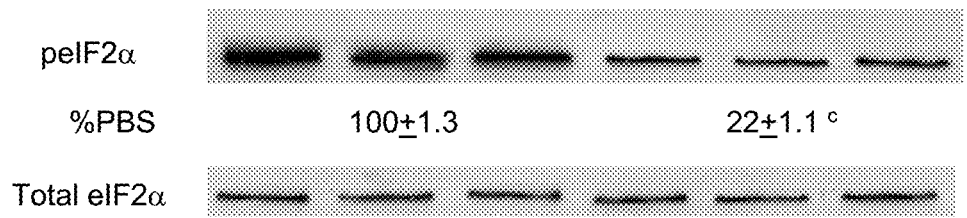

There was a significant reduction in the expression of the phosphorylated forms of both dsRNA-dependent protein kinase (PKR) and eukaryotic initiation factor 2 (eIF2) on the α-subunit in gastrocnemius muscle of rats administered ZAG, while the total amount did not change (FIGS. 17A and 17B). Similar changes have been observed in ob/ob mice administered ZAG (unpublished results) and were consistent with a depression of protein degradation and increase in protein synthesis in skeletal muscle.

EXAMPLE 2

Interval Administration of Zinc-$\alpha_2$-glycoprotein

It was observed that long-term daily administration of ZAG in ob/ob mice results in a cessation of weight loss. As such, it was determined that a break of 3-4 days followed by re-infusion ZAG resulted in continued weight loss and amelioration of the symptoms associated with hyperglycemia.

While not wanting to be limited by theory, it may be that the subjects are receiving too much ZAG or that there is receptor desensitization as is seen with TNF. A pilot study was performed with 2 mice in each group to determine optimal scheduling of ZAG delivery. An 8-10 g weight loss from a 90 g mouse was observed in about 3 weeks.

Figure 9:
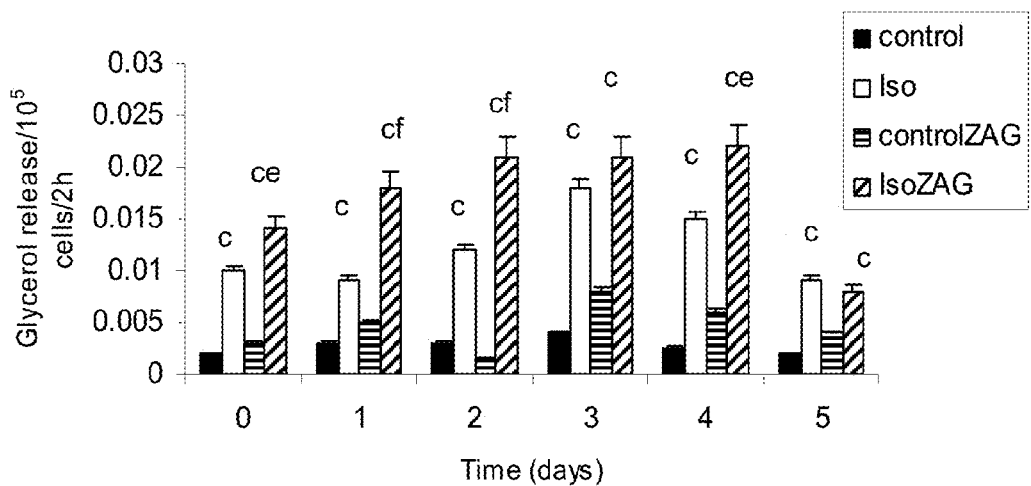
FIG. 9 is a graphical diagram showing glycerol release stimulated by isoprenaline (iso) isolated adipocytes which have been in culture up to 5 days from ob mice treated with and without ZAG.

Adipocytes were removed from mice after 5 days of ZAG and their responsiveness to isoprenaline (iso) was measured after culture in the absence of ZAG (FIG. 9). The responsiveness to iso is higher in ZAG treated mice and this continues for a further 4 days (which was when expression of ZAG and HSL were increased) and then falls on day 5 (when expression was not increased) down to values of PBS control.

EXAMPLE 3

Zinc-$\alpha_2$-glycoprotein Attenuates Muscle Atrophy in Ob/Ob Mouse

Figure 18A:
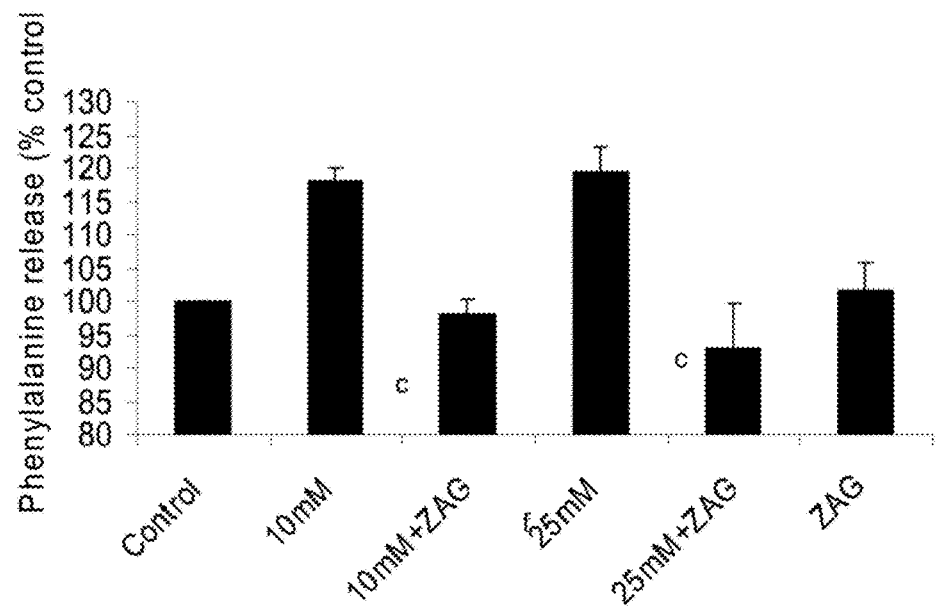
FIGS. 18A and 18B is a graphical diagram showing phenylalanine release (FIG. 18A) and protein synthesis (FIG. 18B) in C2Cl2 myotubes treated with and without ZAG for 4 h in the presence of various concentrations of glucose. Statistically significant c, P<0.001 from control; f, P<0.001 from glucose alone.
Figure 18B:
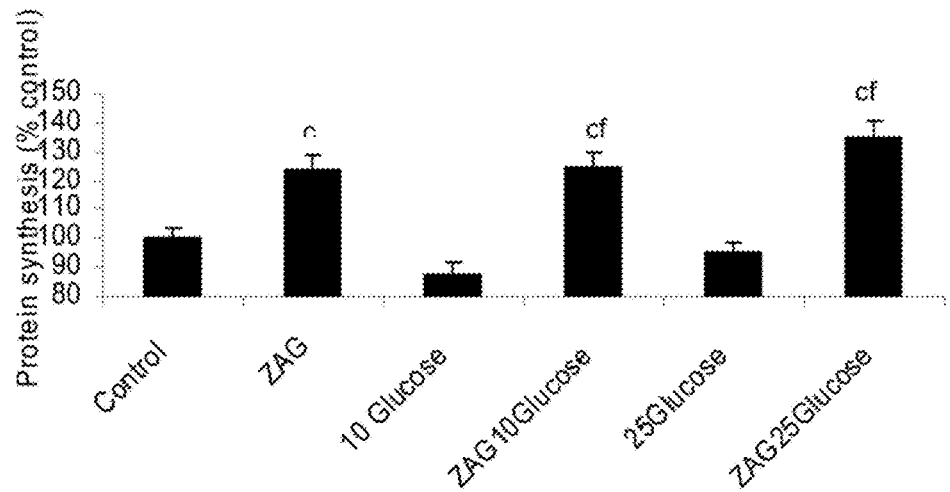
Figure 19:
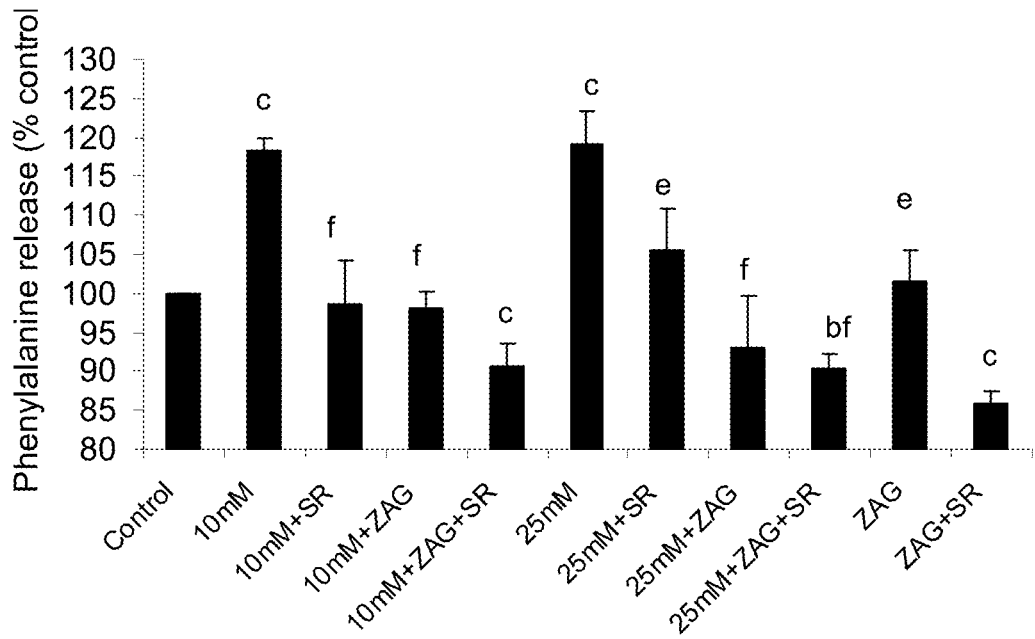
FIG. 19 is a graphical diagram showing pheylalanine release in C2Cl2 myotubes treated with and without ZAG in the presence of various concentrations of glucose and with and without SR59230A. Statistically significant b, P<0.01 and c, P<0.001 from control; e, P<0.05 and f, P<0.001 from glucose alone.
Figure 20:
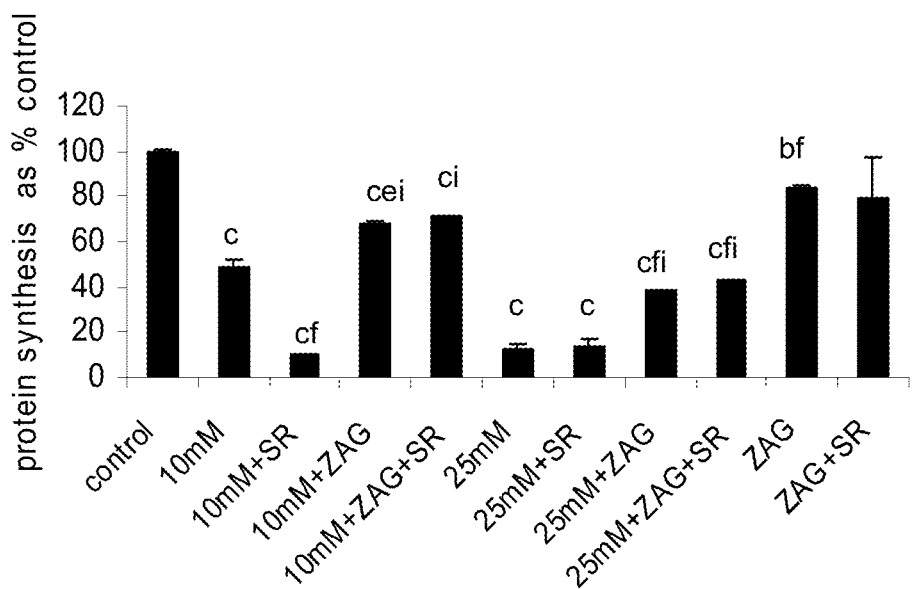
FIG. 20 is a graphical diagram showing protein synthesis in C2Cl2 myotubes treated with and without ZAG in the presence of various concentrations of glucose and with and without SR59230A. Statistically significant b, P<0.01 and c, P<0.001 from control; e, P<0.05 and f, P<0.001 from glucose alone; I, P<0.001 from glucose+SR.

This example demonstrates the mechanism by which ZAG attenuates muscle atrophy in the ob/ob mouse using a newly developed in vitro model (Russell et al, Exp. Cell Res. 315, 16-25, 2009). This utilizes murine myotubes subjected to high concentrations of glucose (10 or 25 mM). As shown in FIG. 18 high glucose stimulates an increase in protein degradation (FIG. 18A), and depresses protein synthesis (FIG. 18B), and both of these effects were completely attenuated by ZAG (25 μg/ml). It was therefore determined if the effect of ZAG was mediated through a β3-AR using the antagonist SR59230A. However the SR compound (i.e., SR59230A) can also act as a β-agonist, which it seemed to do in these experiments. Thus protein degradation induced by both 10 and 25 mM glucose was attenuated by both ZAG and the SR compound, and the combination was additive rather than antagonistic (FIG. 19). For protein synthesis (FIG. 20) the SR compound seems to be similar to ZAG with no evidence of reversal, while with 10 mM glucose the SR compound causes an increase in the depression of protein synthesis.

EXAMPLE 4

Zinc-$\alpha_2$-glycoprotein Attenuates ROS Formation

Figure 21:
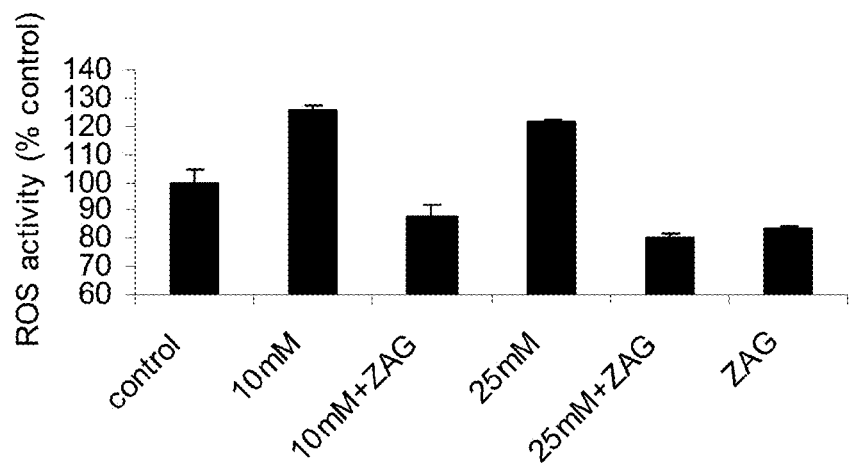
FIG. 21 is a graphical diagram showing ROS activity in C2Cl2 myotubes treated with various concentrations of glucose with and without ZAG. Statistically significant c, P<0.001 from control f, P<0.001 from glucose alone.
Figure 22A:
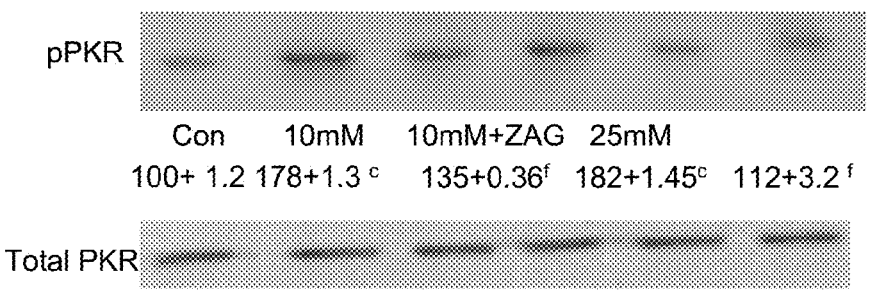
FIG. 22A is a pictorial diagram of a Western blot showing pPKR in C2Cl2 myotubes treated with glucose with and without ZAG. Statistically significant c, P<0.001 from control f, P<0.001 from glucose alone.
Figure 22B:
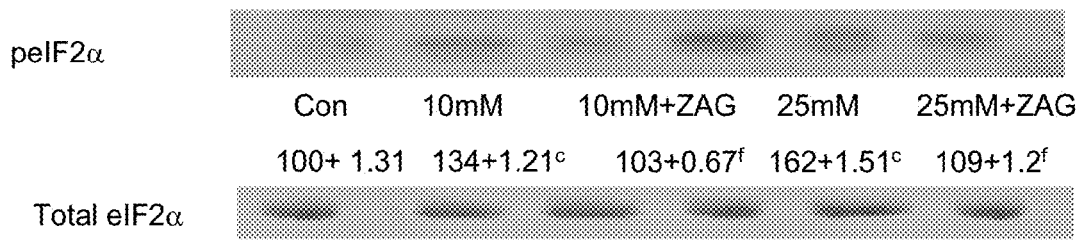
FIG. 22B is a pictorial diagram of a Western blot showing peIF2α in C2Cl2 myotubes treated with glucose with and without ZAG. Statistically significant c, P<0.001 from control f, P<0.001 from glucose alone.

It has been shown that formation of reactive oxygen species (ROS) is important in protein degradation induced by high glucose load. The data in FIG. 21 shows that ZAG completely attenuates the increase in ROS produced by glucose, corresponding with the decrease in protein degradation (FIG. 18A). High glucose also induces activation (phosphorylation) of PKR (FIG. 22A) and the subsequent phosphorylation of eIF2α (FIG. 22B) as is seen in skeletal muscle of ob/ob mice, which was also attenuated by ZAG. These results suggest that this in vitro model will be useful to study how ZAG affects muscle mass at the molecular level.

EXAMPLE 5

Zinc-$\alpha_2$-glycoprotein Increases Insulin Tolerance

Figure 23A:
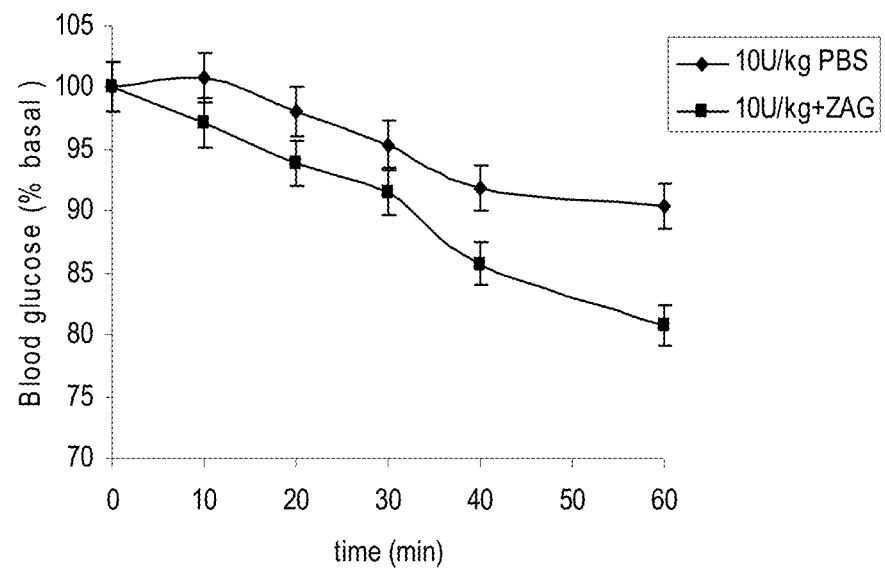
FIGS. 23A and 23B are graphical diagrams showing the results of an insulin tolerance test in ob/ob mice treated with and without ZAG. Statistically significant b, $P<0.05$ and c, $P<0.001$ from with ZAG.
Figure 23B:
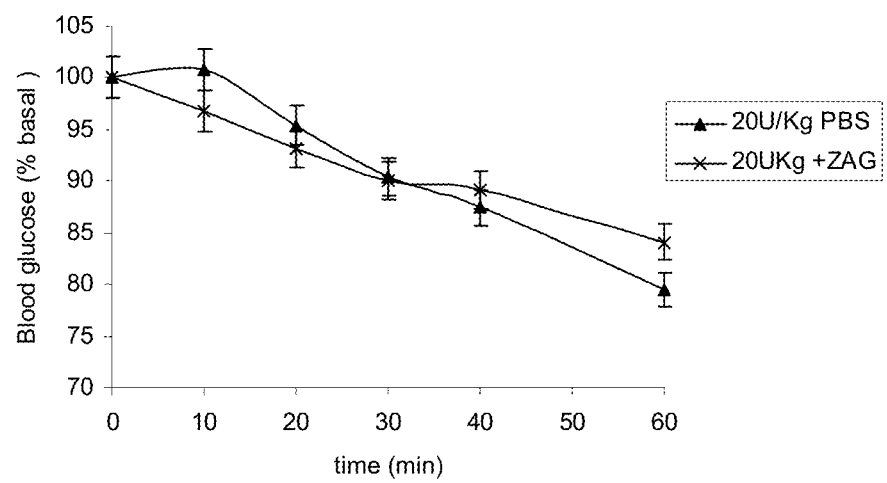

An insulin tolerance test was also carried out in ob/ob mice administered ZAG for 3 days (FIG. 23). Animals were administered two doses of insulin (10 and 20 U/kg) by i.p. injection and blood glucose was measured over the next 60 min. As can be seen (FIG. 23A) animals treated with ZAG showed an increased sensitivity to insulin (10 U/kg) than those given PBS. At the higher concentration of insulin (20 U/kg) this difference disappeared (FIG. 23B). The glucose disappearance curve for 20 U/kg+PBS was almost identical to 10 U/kg+ZAG, so at this dose level ZAG is reducing the requirement for insulin by 50%, but this can be overcome by giving more insulin.

EXAMPLE 6

Anti-Zinc-$\alpha_2$-glycoprotein Antibodies Reduce Weight Loss

The data shown in FIGS. 26-29 is from a study where the β3 agonist, BRL37344 was administered alone and in combination with an anti-ZAG antibody at 50 μg per day on a daily basis. Within 24 hours of administration, mice that were administered the antibody showed significant reduction in weight loss, as compared to mice administered BRL37344.

EXAMPLE 7

5-Day Administration of Zinc-$\alpha_2$-glycoprotein

A 5 day study was performed where ZAG was administered at 35 μg per day i.v. on a daily basis for 5 days. At the end of the experiment tissues were removed and blotted, or functional assays were carried out with isolated adipocytes. As can be seen in FIG. 6A, ZAG administration increased its expression in epididymal (ep), subcutaneous (sc) and visceral (vis) fat about two-fold. When ep adipocytes were prepared and maintained in tissue culture (RPMI 1640+10% FCS) ZAG expression was maintained for a further 3 days, even though no ZAG was added to the culture medium (FIG. 6B). In addition adipocytes from ZAG treated mice showed an increased response to isoprenaline (10 μM), and this was also maintained for 4 days in tissue culture in the absence of ZAG (FIG. 9). The increased response to isoprenaline is due to an increased expression of HSL by ZAG, and this was also maintained in tissue culture for 4 days in the absence of ZAG (FIG. 6C). These results show that the effects of ZAG are maintained for a further 3 days when ZAG is withdrawn and therefore it need not be administered on a daily basis. In fact, as discussed above, too much ZAG is more likely to lead to resistance rather than an increased response.

An increased expression of HSL was only seen in ep adipocytes after 5 days ZAG (FIGS. 5B-5D), as was ATGL (FIGS. 5E-5G). There was an increase in expression of pERK only in ep adipose tissue (FIGS. 5H-5J), and an inhibitor of pERK (PD98059 10 µM) attenuated the increase in expression of HSL in ep adipocytes incubated with ZAG for 3 h (FIG. 5A). ZAG increased expression of UCP1 and UCP3 in BAT (FIGS. 6D and 6E) and muscle (FIG. 6F) which would account for the increase in body temperature and fall in TG and NEFA in serum despite the increase in lipolysis.

EXAMPLE 8

Role of β-Adrenergic Receptors in the Anti-obesity and Anti-diabetic Effects of Zinc-$α_2$-glycoprotein The goal of the study was to determine whether the β-adrenoreceptor (β-AR) plays a role in the anti-obesity and anti-diabetic effects of zinc-α2-glycoprotein (ZAG). This has been investigated in CHO-K1 cells transfected with the human β1-, β2-, β3-AR and in ob/ob mice. In CHO-K1 cells transfected with the β3-AR the lowest concentration of ZAG to stimulate cyclic AMP production was 350 nM, while higher concentrations (580 nM) were required for cells transfected with the β2-AR, and there was no increase in cyclic AMP in cells transfected with the β1-AR. This correlated with the Kd values for binding to the β3-AR (46±4 nM) and β2-AR (71±2 nM), while there was no binding to the β1-AR. Freeze-thawing of ZAG, which destroyed its biological activity eliminated binding to β2- and β3-AR. Treatment of ob/ob mice with ZAG increased protein expression of β3-AR in gastrocnemius muscle, and in white and brown adipose tissue, but had no effect on expression of β1- and β2-AR. The effect of ZAG on reduction of body weight and urinary glucose excretion, increase in body temperature, reduction in maximal plasma glucose and insulin levels in the oral glucose tolerance test, and stimulation of glucose transport into skeletal muscle and adipose tissue, was completely attenuated by the non-specific β-AR antagonist propanolol. These results evidence that the effect of ZAG on body weight and insulin sensitivity in ob/ob mice are manifested through a β-3AR, or possibly a β2-AR.

Zinc-$α_2$-glycoprotein (ZAG) was first recognised to play a role in lipid metabolism when tryptic fragments of a lipid mobilizing factor (LMF), thought to be responsible for loss of adipose tissue in cancer cachexia, were shown to be identical in amino acid sequence to ZAG. Both ZAG and LMF were shown to be immunologically identical, and both stimulated lipolysis in murine adipocytes by the same amount, at the same concentration, by activation of adenylyl cyclase in a GTP-dependent process. Initial studies suggested that ZAG originated from the tumour, since tumours initiating cachexia showed high levels of expression, while other tumours which did not induce cachexia showed no expression. Later studies showed that ZAG was also produced in normal tissues including liver, brown adipose tissue (BAT) and white adipose tissue (WAT), so that ZAG can be classified as an adipokine. Moreover, in both cachectic mice and humans expression of ZAG mRNA in WAT was found to be increased 10-fold and 2.7-fold respectively. In cachectic cancer patients ZAG mRNA showed a negative correlation with body mass index (BMI), but a positive correlation with weight loss and serum glycerol levels. In contrast ZAG mRNA levels in WAT have been shown to be downregulated in obesity and correlated negatively with fat mass, BMI, plasma insulin and leptin. Treatment of ob/ob mice with ZAG decreased body weight and fat mass and improved the parameters of insulin resistance including decreasing plasma levels of glucose, insulin and non-esterified fatty acids (NEFA), improving insulin sensitivity, and increasing muscle mass. Serum ZAG levels have been found to be significantly lower in mice fed a high fat diet than those fed a normal diet, as well as in obese humans and mice. While ZAG overexpression in mice reduced both the body weight and weight of epididymal fat, ZAG knock-out animals showed an increased body weight, especially when fed a high fat diet. These results suggest that ZAG, like leptin, is closely associated with fat mass. However, while leptin is positively correlated with fat mass, ZAG is negatively correlated.

The lipolytic effect of ZAG was shown to be attenuated by the β3-adrenoreceptor (β3-AR) antagonist, SR59230A, while LMF has been shown to bind to the β3-AR through a high affinity binding site (Kd 78±4.5 nM). These results suggest that lipolysis mediated by ZAG is manifested through a β3-AR. This study examined the role of the β3-AR in the action of ZAG, as well as determine the binding to $β_1$- and $β_2$-AR, and the role of the β-AR in the anti-obesity and anti-diabetic effects of ZAG.

FCS (foetal calf serum) was from Biosera (Sussex, UK), while DMEM (Dulbecco's modified Eagle's medium) was from PAA (Somerset, UK) and Freestyle media and Superscript II reverse transcriptase were purchased from Invitrogen (Paisley, UK). 2-[1-$^{14}$C] deoxy-D-glucose sp.act. 1.85 GBq mmol$^{-1}$) was purchased from American Radiolabeled Chemicals (Cardiff, UK). Na [$^{125}$I] (specific radioactivity >17Ci mg$^{-1}$) was purchased from Perkin Elmer Limited. Chicken polyclonal antibody to β3-AR and rabbit polyclonal antibodies to β1-AR and β2-AR were purchased from Abcam (Cambridge, UK) and peroxidise-conjugated goat anti-chicken antibody was from Santa Cruz (USA). Polyclonal rabbit antibodies to UCP1 and UCP3 were from Calbiochem (via Merck Chemicals, Nottingham, UK). Peroxidase-conjugated goat anti-rabbit antibody was from Dako (Cambridge, UK). Polyclonal rabbit antibody to mouse β-actin, Tri-Reagent and propanolol were from Sigma Aldrich (Dorset, UK). Hybond A nitrocellulose membranes were from GE Healthcare (Bucks, UK). The Parameter cyclic AMP assay kit was purchased from New England Biolabs (Hitchin, UK). The iodo beads and enhanced chemiluminescence (ECL) development kits were purchased from Thermo Scientific (Northumberland, UK). A mouse insulin ELISA kit was purchased from DRG (Marburg, Germany) and glucose measurements were made using a Boots (Nottingham, UK) plasma glucose kit. Primers for reverse transcription and Easy-A one tube RT.PCR system were from Agilent Technologies (Cheshire, UK).

Animals. Obese (ob/ob) hyperglycaemic mice having an average weight of 71 g were bred. The background of these animals has been previously described (Bailey C J, et al. Influence of genetic background and age on the expression of the obese hyperglycaemic syndrome in Aston ob/ob mice. Int J Obes 6: 11-21, 1982), and they exhibit a more severe form of diabetes than C57BL/6J ob/ob mice. Male mice (about 20 weeks of age) were grouped into three per cage and kept in an air conditioned room at 22±2° C., with ad libitum feeding of a rat and mouse breeding diet (Special Diet Services, Witham, UK) and tap water. Mice were administered ZAG (50 μg, i.v. in 100 μl PBS) or PBS daily with or without propanolol (40 mgkg$^{-1}$, po, daily) and body weight and food and water intake were determined, as well as urinary glucose excretion and body temperature, determined by the use of a rectal thermometer (RS Components, Northants, UK). A glucose tolerance test was performed on day 3. Glucose (1 gkg$^{-1}$ in a volume of 100 μl) was administered orally to animals which had been fasted for 12 h. Blood samples were removed from the tail vein at 15, 30, 60 and 120 min after glucose administration and used for the measurements of glucose and insulin. At the end of the experiment the animals were terminated by cervical dislocation, tissues removed and rapidly frozen in liquid nitrogen, and maintained at −80° C.

Production of Recombinant Human ZAG. Human HEK293F cells, which had been transfected with pcDNA3.1 containing human ZAG were maintained in Freestyle medium, containing neomycin (50 μgml$^{-1}$), under an atmosphere of 5% $CO_2$ in air. After 2 weeks of growth cells were removed by centrifugation (700 g for 15 min) and the medium was concentrated into a volume of 1 ml sterile PBS using an Amicon Ultra-15 centrifugal filter with a M.W. cut-off of 10 kDa. The ZAG was purified as described (Russell S T and Tisdale M J, Antidiabetic properties of zinc-α2-glycoprotein in ob/ob mice. Endocrinol 151: 948-957, 2010), by binding to DEAE cellulose, since ZAG has a high electronegativity, and was eluted with 0.3MNaCl. The ZAG produced by this method was greater than 95% pure and was free of endotoxin, as determined by the LAL Pyrogent single test kit (Lonza). The purified ZAG was stored at 4° C. in PBS.

[$^{125}$I] labelling of ZAG. One iodo bead that had been washed and dried was incubated with Na [$^{125}$I] (1 mCi per 100 μg protein) for 5 min in PBS, then ZAG (100 μg protein) was added and left for a further 15 min. The reaction was terminated by removal of the iodo bead, while free Na [$^{125}$I] was removed using a Sephadex G25 column eluted with 0.1MNaI. The [$^{125}$I] ZAG was concentrated against PBS using a Microcon microconcentrator with a filter cut-off of Mr 10,000. The specific activity of the [$^{125}$I] ZAG was 8 Cimg protein$^1$.

Binding Studies and Cyclic AMP Determination. CHO-K1 cells transfected with the human β1- and β2-AR obtained from University of Nottingham, UK, while CHOK1 cells transfected with the β3-AR were obtained from Astra Zeneca, Macclesfield, Cheshire, UK. Gene expression was under the control of hygromycin, together with a β-gal reporter construct, selected for resistance to G418. They were maintained in DMEM supplemented with 2 mM glutamine, hygromycin B (50 mgml$^{-1}$), G418 (200 mgml$^{-1}$), and 10% FCS, under an atmosphere of 10% $CO_2$ in air. To determine the effect of agonists on cyclic AMP production, cells were grown in 24-well plates containing 1 ml of nutrient medium. ZAG or isoproterenol at the concentrations shown in FIG. 51 were added to the cells and incubation was continued for 30 min. The medium was removed and replaced with 0.5 ml of 20 mM HEPES, pH 7.5, 5 mM EDTA and 0.1 mM isobutylmethylxanthine, and the plates were heated on a boiling water bath for 5 min and cooled on ice for 10 min. The concentration of cyclic AMP was determined with an ELISA assay.

For binding studies cells were sonicated in 2 mM Tris HCl, pH7.5, containing 0.5M $MgCl_2$ and crude total membranes were pelleted by centrifugation (13,000 g; 15 min) at 4° C. Binding studies were carried out at 37° C. by incubating membranes (500 μg protein) in 0.4 ml 50 mM Tris HCl, pH 7.5, containing 0.5 mM $MgCl_2$ for 60 min with various concentrations of [$^{125}$I] ZAG (3,000 to 15,000 cpm) in the absence or presence of 100 μM non-labelled ZAG. The membranes were then precipitated by centrifugation at 13000 g for 20 min, the supernatant was removed and the [$^{125}$I] bound to the pellet was quantitated using a Packard Corbra Model 5005 Auto-gamma counter. Binding was analysed using non-linear regression analysis (GraphPad Prism, Version 5.04). Specific binding was regarded as the amount of labelled ZAG displaced by non-radioactive ZAG.

RNA Isolation and RT-PCR. Quantitation of the mRNA transcripts for β1-, β2- and β3-AR in the three CHO-K1 cells was based on the methodology already described (Moniotte S, et al. Real-time RT-PCR for the detection of beta-adrenoceptor messanger RNAs in small human endomyocardial biopsies. J Mol Cell Cardiol 33: 2121-2133, 2001). Total RNA was extracted with Tri Reagent and quantitated by spectrophotometry, 800±34 ng total RNA was reverse transcribed, together with 2000 pmol random hexamers as primers using Superscript II reverse transcriptase at 43° C. for 50 min. The probe sequences were selected to obtain $T_mS$ approximately 10° C. lower than the matching primer pair. PCR was carried out using Easy-A one tube RT.PCR system according to the manufacturer's instructions. The PCR conditions included a denaturing at 95° C. for 10 min, an annealing step at 42-65° C., and an extension step at 68° C. for 2 min, and with a final extension at 68° C. for 10 min. There were 40 cycles of amplification. Expression of β-AR mRNA was determined by the Δ-CT method using Stratagenes MxPro, QPCR software v3.00.

Western Blot Analysis. WAT, BAT, heart and gastrocnemius muscle were thawed, washed in PBS, and lysed in Phosphsafe™ Extraction reagent for 5 min at room temperature, followed by sonication at 4° C. The supernatant formed by centrifugation at 18,000 g for 5 min at 4° C. was used for Western blotting. Cytosolic protein (5 μg for UCP's and 20 μg for β-AR) was resolved on 12% sodium dodecylsulphate polyacrylamide gels by electrophoresis at 180V for about 1 h and transferred on to 0.45 μm nitrocellulose membranes, which had been blocked with 5% (w/v) non-fat dried milk (Marvel) in Tris-buffered saline, pH 7.5, at 4° C. overnight. Prior to adding the primary antibodies membranes were washed for 15 min in 0.1% Tween 20-buffered saline. Both primary and secondary antibodies were used at a dilution of 1:1000. Incubation was for 1 h at room temperature and development was by ECL. Blots were scanned by a densitometer to quantify differences.

Glucose Uptake into Adipose Tissue and Skeletal Muscle. Uptake of 2-[1-$^{14}$C] deoxy-D-glucose (2-DG) into freshly isolated epididymal adipocytes and gastrocnemius muscle was determined as previously described (Russell S T and Tisdale M J, Antidiabetic properties of zinc-α2-glycoprotein in ob/ob mice. Endocrinol 151: 948-957, 2010).

Statistical Analyses. Results are shown as mean±SEM for at least three replicate experiments. Differences in means between groups was determined by one-way analysis of variance (ANOVA) followed by Tukey-Kramer multiple comparison test. p values <0.05 were considered significant.

Figure 51:
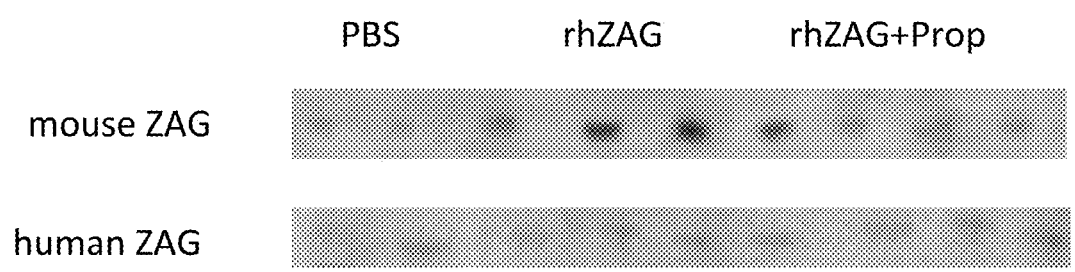
FIG. 51 is a pictorial diagram of a Western blot. Propranolol blocks the increase in murine serum ZAG due to treatment with rhZAG p.o., but the administered human ZAG is not found in plasma. Western blot of ZAG using Anti-mouse ZAG in mouse serum from Mice treated with and without ZAG in the absence or presence of propranonol (top). Human ZAG is not detected in mouse serum. Western blot of ZAG using Anti-human ZAG in mouse serum from Mice treated with and without ZAG in the absence or presence of propranonol (bottom).

The effect of human ZAG on cyclic AMP production in CHO cells transfected with human β1, β2 and β3-AR is shown in FIG. 51. At low concentrations (up to 460 nM) there was specific stimulation of cyclic AMP production only in cells transfected with the β3-AR (FIG. 51A). However, at 580 nM there was also a significant increase in cyclic AMP level in CHO cells transfected with the β2-AR, although the magnitude of the change was less than in cells transfected with the β3-AR. There was no increase in cyclic AMP in CHO cells transfected with the β1-AR at any concentration of ZAG (FIG. 51A). In contrast isoprenaline (10 μM) showed significant increases in cyclic AMP level in CHO cells transfected with β1-, β2- and β3-AR, showing the lack of specificity to the three isoforms of the β-AR (FIG. 51B). The increase in cyclic AMP by isoprenaline through β1-, β2- and β3-AR was attenuated by SR59230A, showing a lack of specificity of this agent to the β3-AR.

To determine whether expression of the β-AR was the same in the three cell lines mRNA levels of β1-AR, β2-AR and β3-AR was determines by RT-PCR as described (Moniotte S, et al. Real-time RT-PCR for the detection of beta-adrenoceptor messanger RNAs in small human endomyocardial biopsies. J Mol Cell Cardiol 33: 2121-2133, 2001). The data in FIG. 51C show that the level of expression of each β-AR is the same in relation to the housekeeping gene GAPDH. Moreover, the level of adenylate cyclase, as determined by cyclic AMP production in the presence of forskolin, was also similar in the three cell lines (FIG. 51D). These results suggest that a comparison between the β-AR in the three cell lines is valid.

The affinity of binding of ZAG to the three β-AR was determined using $^{125}I$ labelled ZAG and crude membranes from CHO-K1, β1, β2 and β3 cells (FIGS. 51E, F and G). The data was evaluated using non-linear regression analysis and the Kd and Bmax values are shown. The binding data reflect the stimulation of cyclic AMP production by ZAG as shown in FIG. 51A. Thus ZAG bound predominantly to β3-AR (high Bmax and lowest Kd), less so to β2-AR (Bmax 20% of β3-AR and Kd twice β3-AR), and not at all to β1-AR (no Bmax and high Kd). Non-specific binding was determined by the binding of $[^{125}I]$ ZAG in the presence of 100 μM non-labelled ZAG, and these values were subtracted from the total binding to give the specific binding values. The lipolytic activity of ZAG was shown to be destroyed by a single freezing and thawing cycle (FIG. 51H), probably due to a change in conformation of the protein. To determine whether this disrupted binding to β-AR two experiments were performed: (i) Freeze-thaw $[^{125}I]$ ZAG was used in the binding studies, which completely attenuated binding to the β2- and β3-AR (FIGS. 51F and G). (ii) Freeze/thawed non-labelled ZAG was used in a competition assay with $[^{125}I]ZAG$, as in the determination of non-specific binding above. In contrast with fresh non-labelled ZAG this had no effect on either the Kd or Bmax for binding to β2-AR or β3-AR. These results suggest that freeze/thawing ZAG destroys biological activity by preventing binding to β-AR.

Figure 52A:
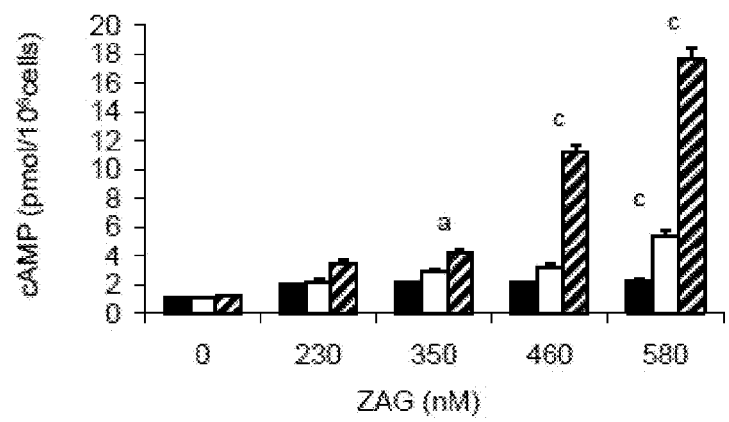
FIG. 52A is a graphical diagram showing the effect of ZAG concentration on cyclic AMP production in CHO cells transfected with β1-AR (■), β2-AR (□) and β3-AR (hashed).
Figure 52B:
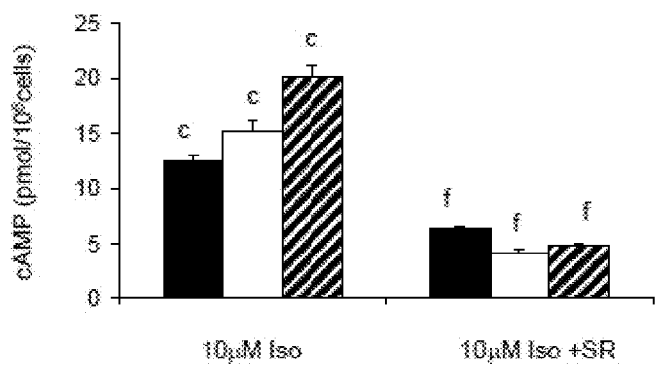
FIG. 52B is a graphical diagram showing effect of isoprenaline (10 μM) on cyclic AMP production in β1-(■), β2-(□) and β3-AR (hashed) transfected CHO cells in the absence or presence of SR59230A (10 μM). Differences from basal levels of cyclic AMP are indicated as either a, $p<0.05$ or c, $p<0.001$.
Figure 52C:
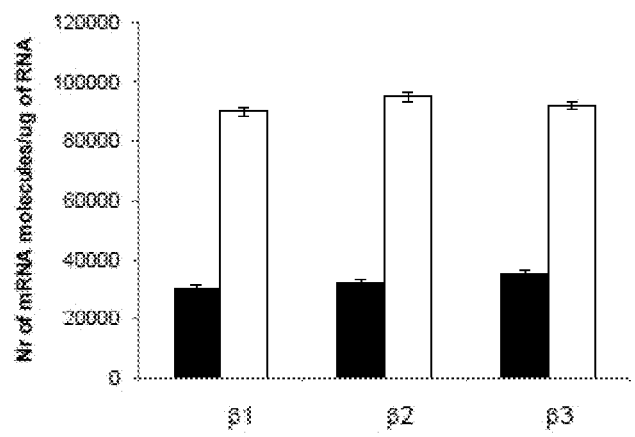
FIG. 52C is a graphical diagram showing mRNA levels. Expression of β1-, β2- and β3-AR in CHO-K1 cells transfected with the respective human genes as absolute numbers of β-AR mRNA molecules/μg of total RNA, measured by RT-real time PCR (closed boxes) in comparison with expression of GAPDH in the same sample (open boxes).
Figure 52D:
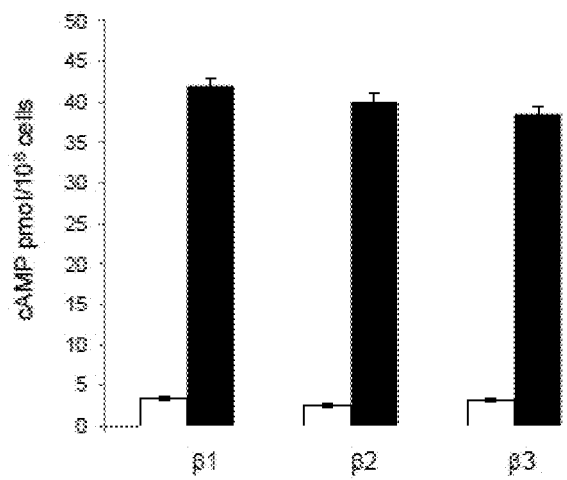
FIG. 52D is a graphical diagram showing cyclic AMP production in CHO-K1 cells transfected with human β1-, β2- and β3-AR in response to forskolin (20 μM) (closed boxes) in relation to basal levels (open boxes).
Figure 52E:
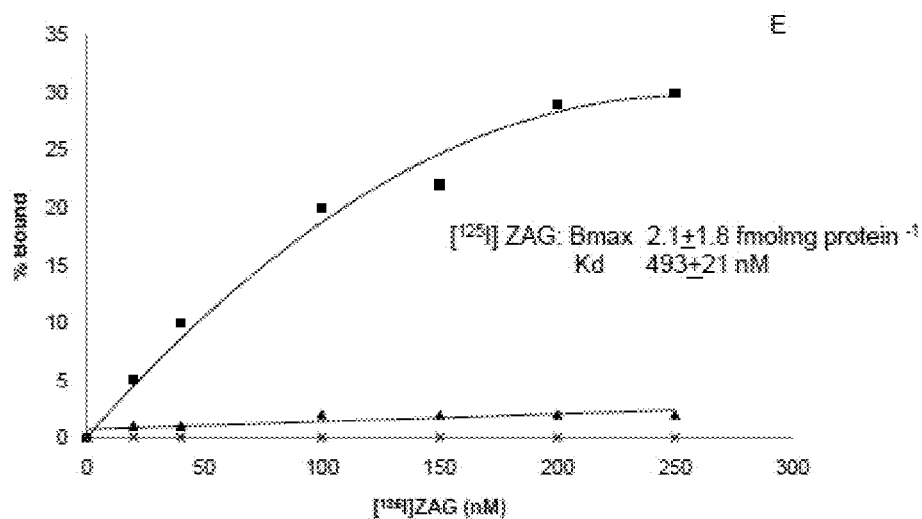
FIGS. 52E, 52F and 52G is a graphical diagram showing specific binding of ZAG to CHO-K1 cells transfected with human β1-(FIG. 52E), β2-(FIG. 52F) and β3-AR (FIG. 52G) in the absence (■) or presence (▲) of 100 uM non-labelled ZAG Binding of similar concentrations of ZAG frozen and thawed(X) is also indicated.
Figure 52F:
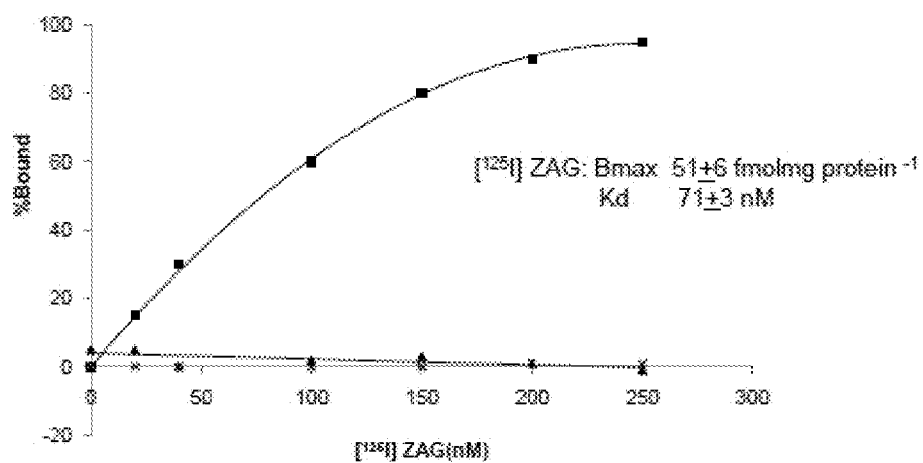
Figure 52G:
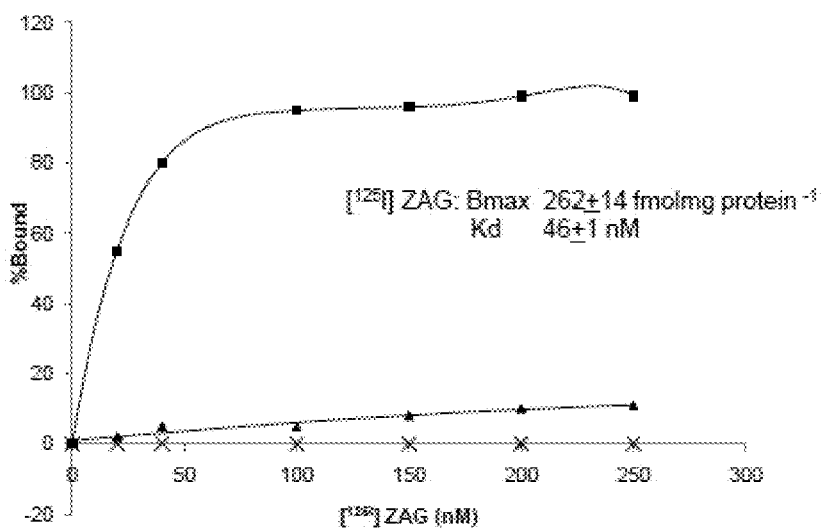
Figure 52H:
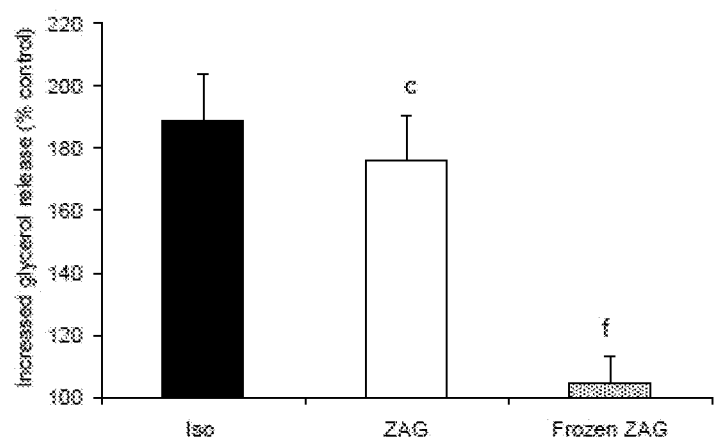
FIG. 52H is a graphical diagram showing lipolytic activity of ZAG (0.58 µM), either fresh (open), or frozen and thawed once (dashed), in comparison with isoprenaline (Iso; 10 µM) (solid) in murine epididymal adipocytes. Differences from control are shown as c, $p<0.001$, while differences between fresh and frozen ZAG and in the presence of SR59230A are shown as f, $p<0.001$.
Figure 53A:
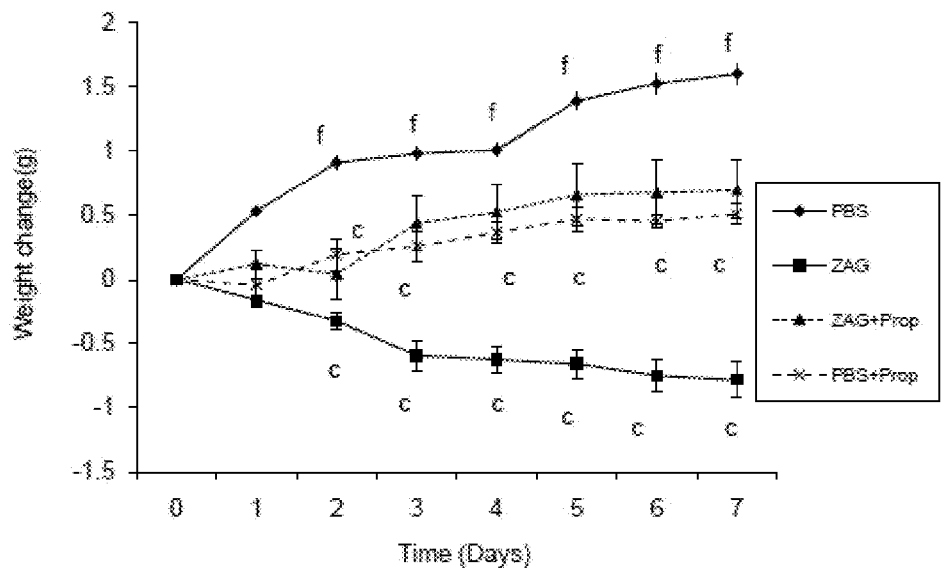
FIG. 53A-53C are a graphical diagrams showing the effect of propanolol on body weight (53A), body temperature (53B) and urinary glucose excretion (53C) in ob/ob mice treated with ZAG. Animals were divided into 4 groups (n=5 per group) to receive daily administration of ZAG (50 mg, iv) (■), ZAG+propanolol (40 mgkg$^{-1}$, po) (▲), while controls received either PBS (♦) or PBS and propanolol (X). Differences from PBS are shown as c, $p<0.001$, while differences from ZAG alone are shown as f, $p<0.001$.
Figure 53B:
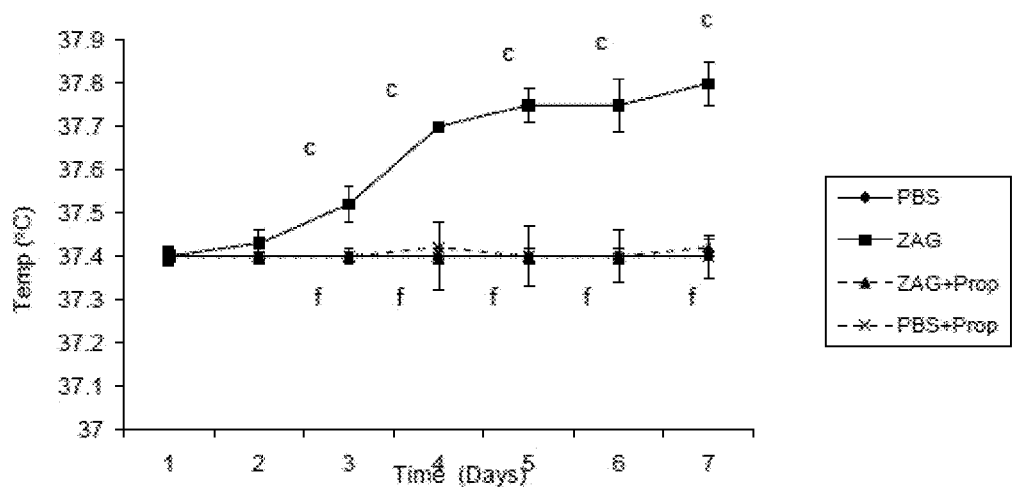
Figure 53C:
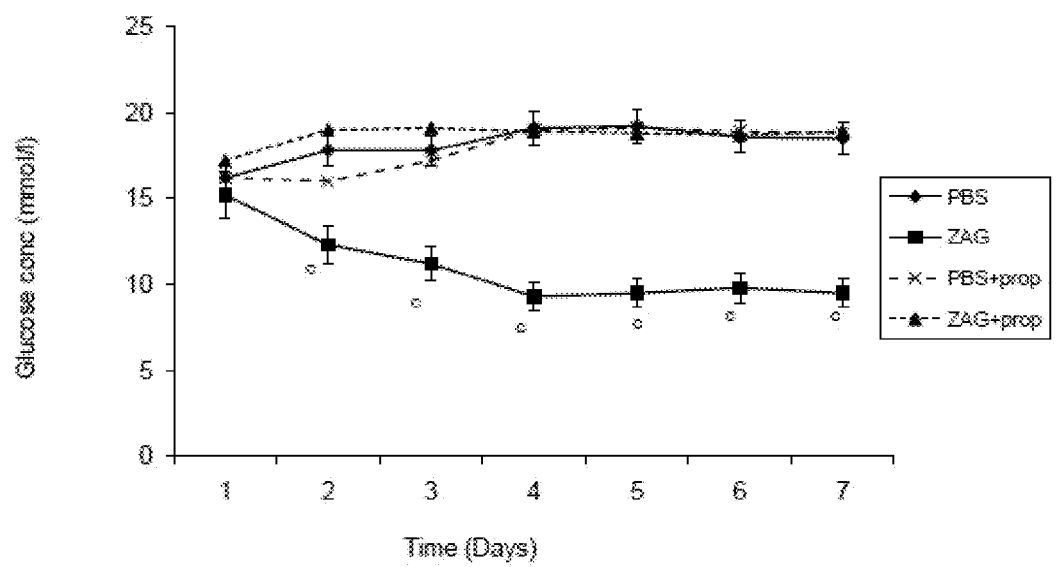
Figure 53D:
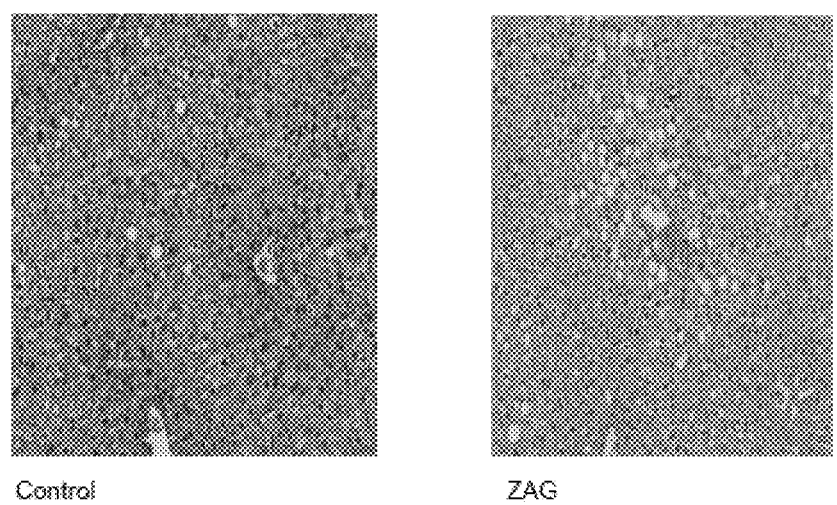
FIG. 53D is a pictorial diagram of liver histology after 60 days comparing control-treated and ZAG-treated example sections.

To determine whether the effects of ZAG on body weight and insulin sensitivity were due to interaction with a β-AR, ob/ob mice were treated with ZAG (50 μg, iv, daily), as previously reported (Russell S T and Tisdale M J, Antidiabetic properties of zinc-α2-glycoprotein in ob/ob mice. Endocrinol 151: 948-957, 2010), in the absence and presence of the non-specific β-AR antagonist propanolol (40 mg $kg^{-1}$, po, daily). This dose level is higher than that commonly employed with β2-AR agonists, since higher levels are required to counteract the effect of β3-AR agonists (Liu Y L and Stock M J, Acute effects of the beta 3-adrenoreceptor agonist, BRL 35135, on tissue glucose utilisation. Br J Pharmacol. 114: 888-894, 1995). Propanolol completely attenuated the decrease in body weight produced by ZAG (FIG. 52A), although animals treated with propanolol alone did not show such a large weight gain as did PBS controls. As previously reported (Russell S T and Tisdale M J, Antidiabetic properties of zinc-α2-glycoprotein in ob/ob mice. Endocrinol 151: 948-957, 2010) mice treated with ZAG showed an increased body temperature (FIG. 52B), and this was completely attenuated by propanolol, as was the reduction in the urinary excretion of glucose (FIG. 52C). ZAG alone had no effect on liver lipids, although there was some increase in glycogen (FIG. 52D). Propanolol also blocked the reduction in peak plasma glucose levels, and the area under the glucose curve (AUC) induced by ZAG in the oral glucose tolerance test (FIG. 53A), as well as the corresponding reduction in peak plasma insulin levels (FIG. 53B). Animals treated with ZAG showed an increased glucose uptake into gastrocnemius muscle in the presence of insulin (10 nM) (FIG. 53C), and this was completely attenuated in gastrocnemius muscle from mice receiving propanolol. Epididymal adipocytes from mice treated with ZAG also showed an enhanced glucose uptake in the absence and presence of insulin (FIG. 53D), and this was also completely attenuated in animals treated with propanolol. The decrease in serum levels of triglycerides (TG) and non-esterified fatty acids (NEFA) produced by ZAG were also attenuated by propranolol (FIGS. 53E and F). These results suggest that the biological effects of ZAG are mediated through a β-AR. To determine whether ZAG can increase insulin signalling the effect on Glut4 expression was determined. Both insulin and ZAG increased expression of Glut4 in gastrocnemius muscle (FIG. 53G) and WAT (FIG. 53H), but the combination did not produce an increase over that of insulin alone. These results suggest that ZAG influences the same signalling pathways as insulin, but does not increase insulin signalling.

Figure 54A:
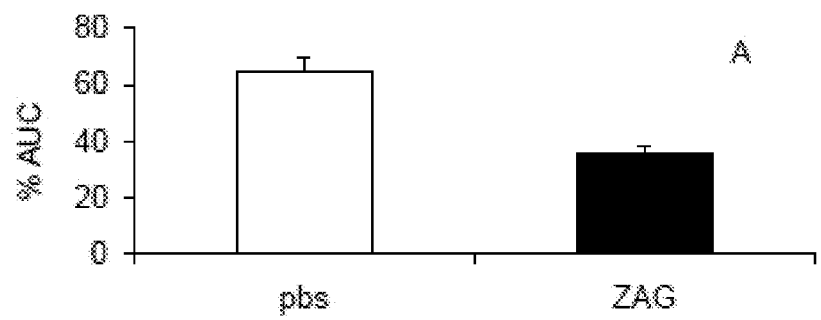
FIG. 54A are a graphical diagrams showing total areas under the glucose curves (AUC) in arbitrary units and plasma glucose levels during a glucose tolerance test 3 days after initiation of ZAG (■) in comparison with PBS (□)
Figure 54A:
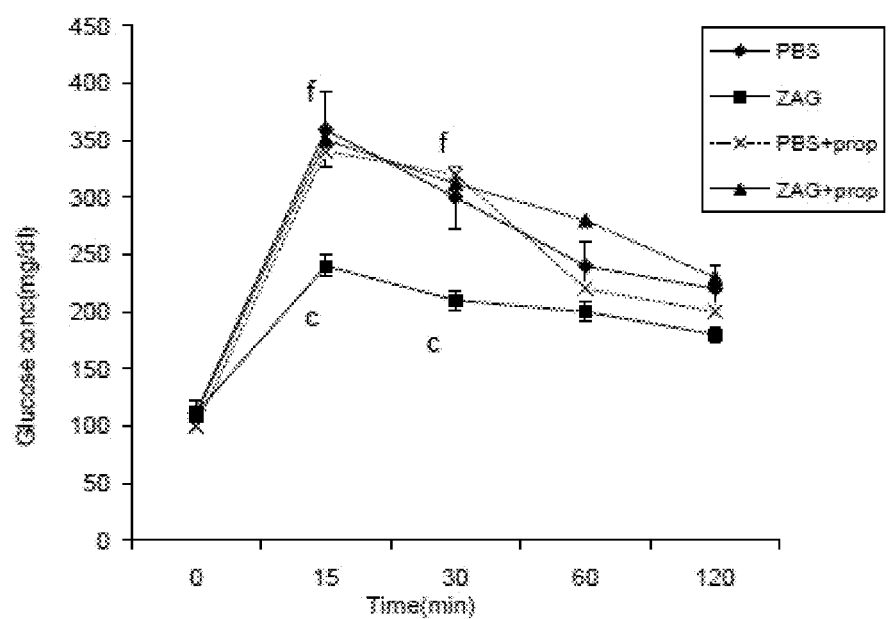
Figure 54B:
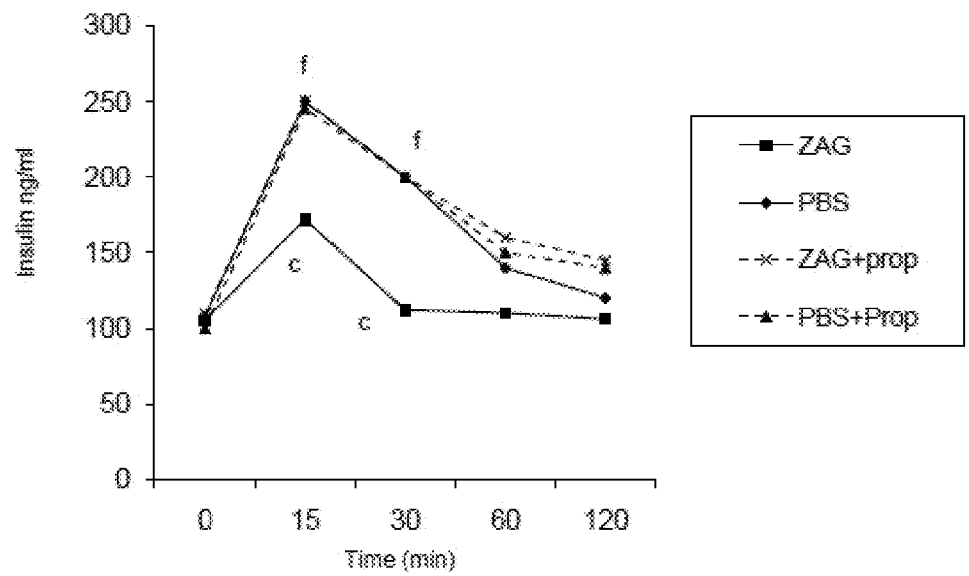
FIG. 54B is a graphical diagram showing plasma insulin levels during the glucose tolerance test described in (FIG. 54A).
Figure 54C:
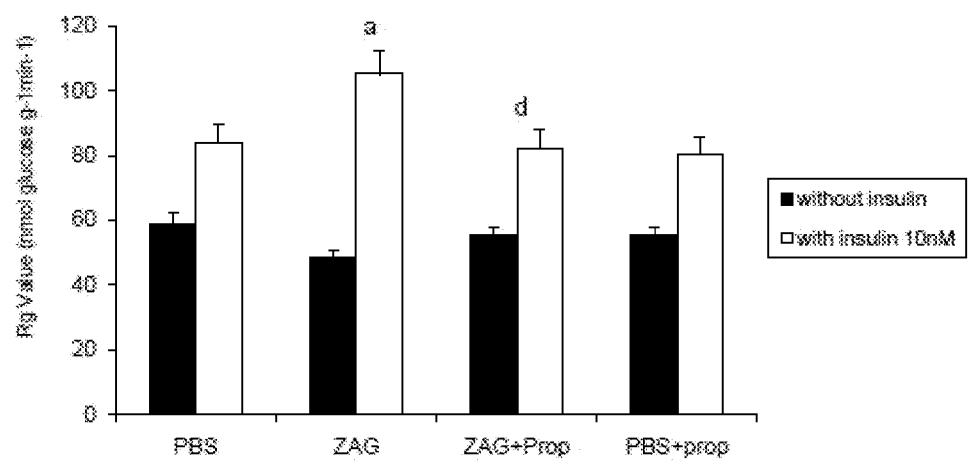
FIG. 54C is a graphical diagram showing glucose uptake into isolated gastrocnemius muscle of ob/ob mice in the absence or presence or insulin (100 nM). Ob/ob mice were treated with ZAG with or without propanolol for 7 days prior to excision of muscle.
Figure 54D:
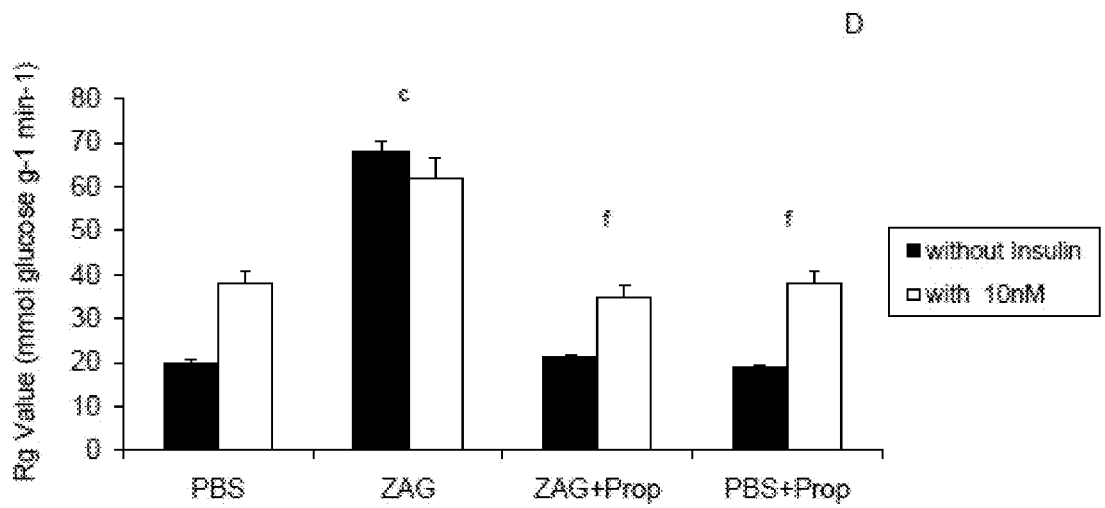
FIG. 54D is a graphical diagram showing glucose uptake into epididymal adipocytes of ob/ob mice in the absence or presence of insulin (10 nM). Animals received the treatments indicated for 7 days prior to excision of WAT.
Figure 54E:
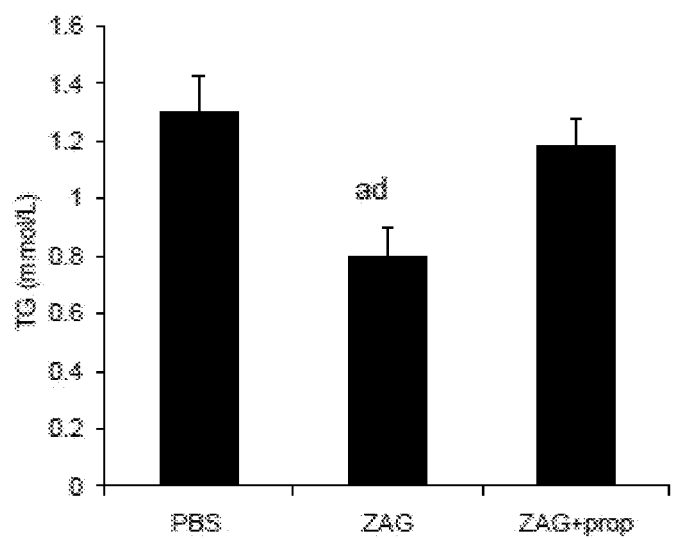
FIGS. 54E and 54F are graphical diagrams showing levels of TG (FIG. 54E) and NEFA (FIG. 54F) in ob/ob mice treated with PBS or ZAG, with or without propranolol for 7 days.
Figure 54F:
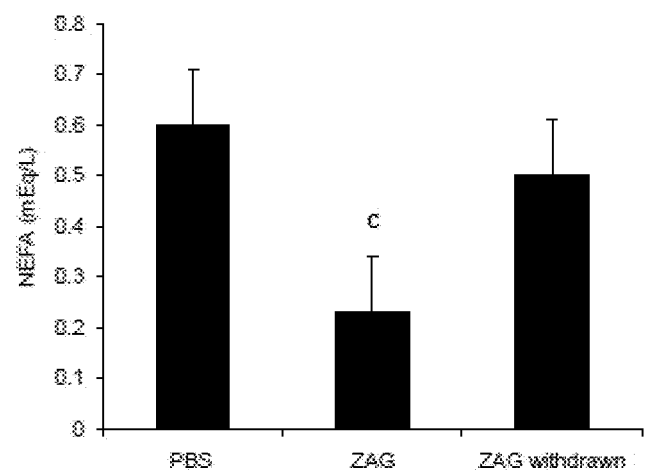
Figure 54G:
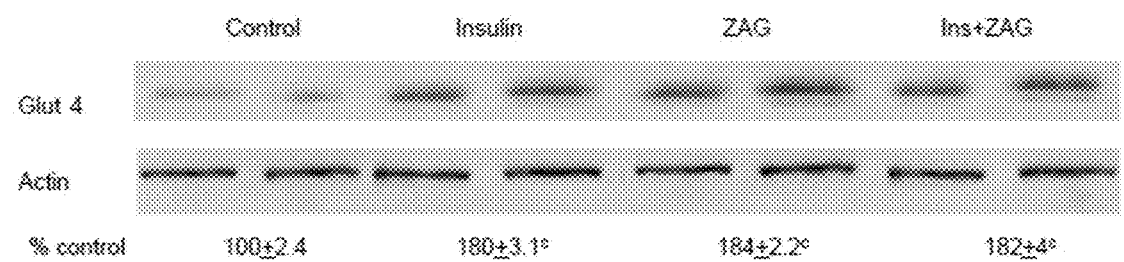
FIGS. 54G and 54H are pictorial diagrams of Western blots showing Glut 4 expression in Gastronemius (54G) and WAT (54H) from ob/ob mice in the presence of ZAG or Insulin or both. Differences from controls are shown as b, $p<0.01$ or c, $p<0.001$, while differences from ZAG alone are shown as d, $p<0.05$ or f, $p<0.001$.
Figure 54H:
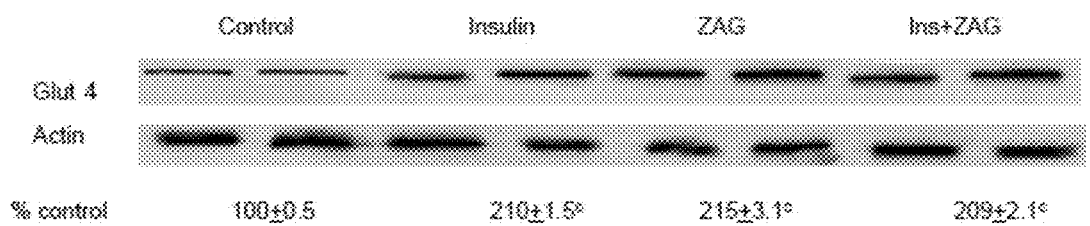
Figure 55A:
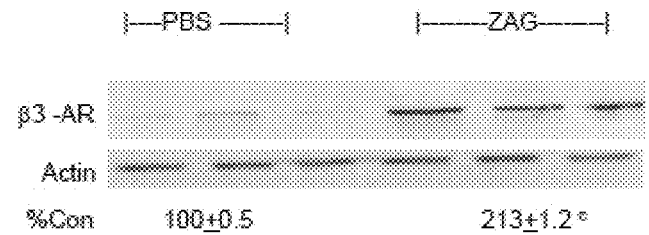
FIG. 55A is a pictorial diagram of a Western blot.
Figure 55B:
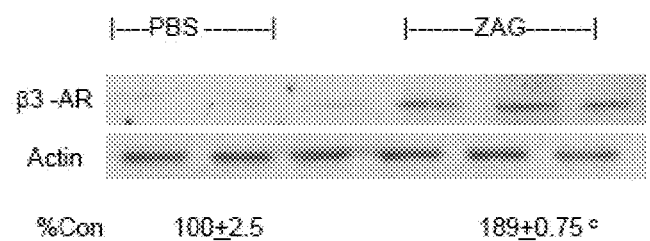
Figure 55C:
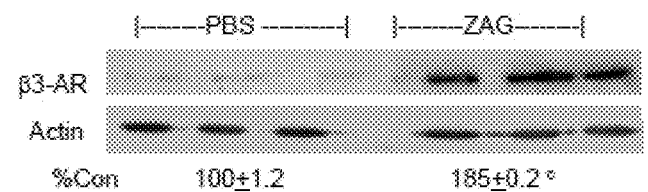
Figure 57B:
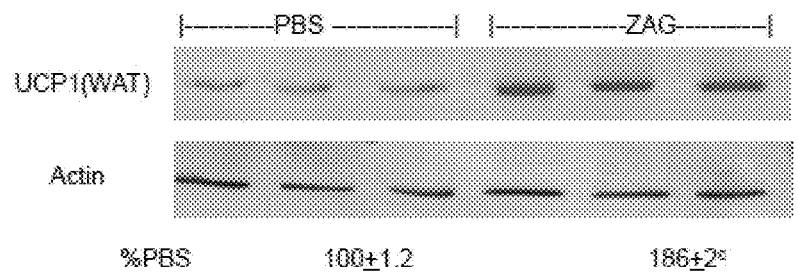
Figure 57C:
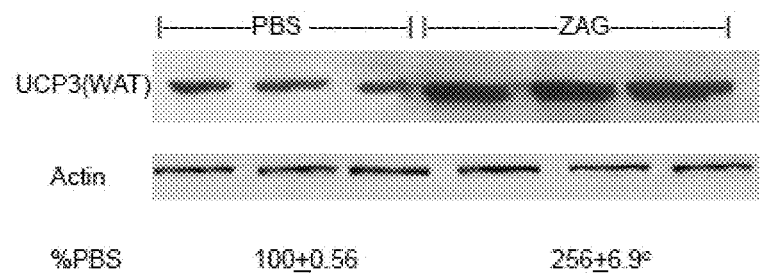
Figure 57D:
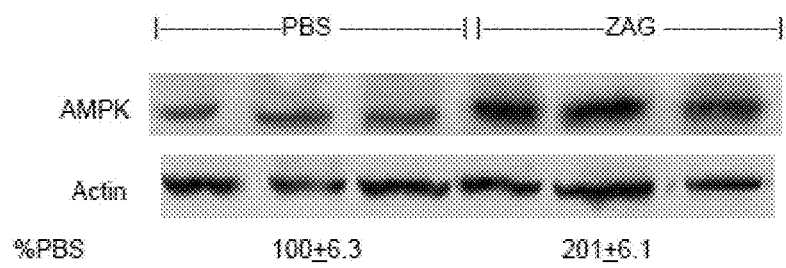

A number of β3-agonists are known to increase expression of the β3-AR. To determine whether ZAG had the same effect, tissue β3-AR expression was quantified by Western blotting after 5 days of treatment of ob/ob mice with ZAG. The results in FIG. 54 show a two-fold increase in β3-AR expression in gastrocnemius muscle (FIG. 54A) an 89% increase in BAT (FIG. 54B) and an 85% increase in WAT (FIG. 54C). In contrast there was no change in expression of β1-AR or β2-AR in either gastrocnemius muscle (FIG. 55A) or WAT (FIG. 55B) and no change in expression of β1-AR in heart (FIG. 55C), but a small increase in β2-AR which just reached significance (FIG. 55C).

The increased expression of the β3-AR in BAT and WAT (FIG. 54) would be expected to lead to an increased expression of UCP1, which is observed in both BAT (FIG. 56A) and WAT (FIG. 56B) after ZAG administration. In vitro experiments have shown that induction of expression of UCP3 by ZAG was attenuated by the mitogen activated protein kinase kinase (MAPKK) inhibitor PD98059, suggesting the involvement of MAPK in this process. Previous studies have shown an increase in expression of ERK in WAT of ZAG-treated mice. This would be expected to lead to an increase in expression of UCP3 in WAT, as was observed (FIG. 56C). It was also previously reported that an increase in UCP3 in skeletal muscle of ob/ob mice after administration of ZAG. The increased expression of UCP's would provide a sink for the NEFA released from adipose tissue, generating heat as previously reported.

In addition treatment with ZAG produced an increase in expression of AMPK in skeletal muscle (FIG. 56D), which would lead to an increase oxidation of long-chain fatty acids, decreasing the availability for the synthesis of triglycerides, as well as stimulating glucose uptake through increased expression of GLUT4.

This study has found that ZAG binds predominantly to the β3-AR, with intermediate binding to the β2-AR, and no binding to the β1-AR. The human β3-AR is 51% homologous in amino acid sequence to the β1-AR and 46% homologous to the β2-AR. The Bmax for ZAG binding to the β3-AR is about three times that for the β2-AR, while the Kd is about half. The Kd for ZAG for binding to the β3-AR is about 100-fold lower than that of CGP12177, a partial agonist, while the Bmax is only slightly lower. These results were obtained using [$^{125}$I] ZAG which may have non-equivalent binding activity to native ZAG, which could lead to over or under estimation of the Kd. While most of the studies with ZAG have been carried out in rodents there is a difference between human and rodent β3-AR. Thus BRL37344 is less effective at stimulating adenylyl cyclase via human than rodent β3-AR, while CGP12177 is an effective agonist at human β3-AR, but a poor partial agonist at the rat β3-AR. How ZAG binds to the β3-AR and β2-AR, while not binding to the β1-AR, is not known, but the conformation of the protein is very important, since binding is destroyed by a single freeze/thaw cycle, as is also the ability of ZAG to stimulate lipolysis in murine adipocytes. The Kd values are in the range expected, both from studies on the stimulation of lipolysis, and cyclic AMP production by ZAG. However, they are more than 10-times lower than the human plasma concentration reported using an ELISA (600 nM), but are comparable with that reported using mass spectrometry (85 nM). If the former value was true ZAG would be maximally stimulating the β2- and β3-AR at normal plasma concentrations, which is clearly not correct. Care must be taken in interpreting plasma concentrations of ZAG using an ELISA, since there may be other components which bind to the anti-ZAG antibody, giving apparently higher concentrations. Thus ZAG has been shown to non-specifically bind to a monoclonal antihuman erythropoietin antibody giving apparently higher values in samples containing increased amounts of urinary ZAG.

The effect of ZAG on obesity and diabetes in the ob/ob mouse model may be due to its ability to bind to β3-AR. Thus β3-AR agonists show anti-obesity effects in rodent models similar to ZAG, which induced an increased mobilisation of triglycerides from WAT depots, increased fat oxidation, and increased BAT-mediated thermogenesis, resulting in a selective reduction in body fat and preservation of fat-free mass. As with ZAG the anti-diabetic effects of β3-AR agonists are independent of the anti-obesity effects, and occur at dose levels which do not induce weight loss. Treatment of ob/ob mice with the β3-AR agonist BRL 35135 normalised plasma glucose levels and significantly decreased plasma insulin and non esterified fatty acid (NEFA) levels. As with ZAG BRL 35135 stimulated glucose uptake into three types of skeletal muscle, BAT, WAT, heart and diaphragm, which was independent of the action of insulin. Another β3-agonist L-796568 increased lipolysis and energy expenditure in obese men when administered as a single dose. However, treatment for 28 days had no major lipolytic or thermogenic effect, although it lowered triacylglycerol concentration. This may be due to insufficient recruitment of β3-AR responsive tissues in humans, or down-regulation of β3-AR with chronic dosing. Studies in human subcutaneous abdominal adipose tissue show that β3-AR play a weaker role in the control of lipolysis than found in rodents, and that mobilisation of lipids is mainly through β1 and β2-AR subtypes. Thus ZAG may exert its effect in humans via a β2-AR rather than β3-AR.

This study has shown that propanolol, a non-specific β-AR antagonist attenuates the effect of ZAG in reducing body weight and urinary glucose excretion, increasing body temperature, improving the response to glucose in the oral glucose tolerance test and increasing glucose uptake into skeletal muscle and WAT of ob/ob mice, when administered at high dose levels. In addition freeze-thawing, which destroyed the ability of ZAG to induce lipolysis in WAT, and reduce body fat in aged obese mice also completely attenuates its ability to bind to human β2- and β3-AR. These results confirm that the anti-obesity and anti-diabetic effects of ZAG are mediated through a β-AR.

This study has also shown that administration of ZAG to ob/ob mice increases the expression of β3-AR protein in BAT, WAT and skeletal muscle. This effect is also seen with other β3-AR agonists. Thus chronic treatment of ob/ob mice with the β3-AR agonist BRL35135 resulted in a two-fold increase in β3-AR mRNA in BAT. Similar effects were reported with another β3-AR agonist CL 316,243 in Zucker fa/fa rats, and in adipocytes of adult humans. Thus the ability of ZAG to induce expression of the β3-AR would enhance its effect on obesity and diabetes. The reduced β-AR mediated lipolysis and fat oxidation seen in obese subjects may be due to low levels of ZAG, and that administration of ZAG could improve sensitivity. Certainly ZAG administration to ob/ob mice increased sensitivity of epididymal adipocytes to the lipolytic effect of the β3-AR agonist, BRL 37344. The ability of ZAG to induce expression of β3-AR would explain the lack of response of adipose tissue from ZAG 'knock-out mice' to the lipolytic effect of the β3-AR agonist CL316243.

Using knock-out mice the antiobesity effect of β3-AR stimulation has been shown to be through the UCP-1 dependent degradation of fatty acids released from WAT. Until recently BAT was considered to be restricted to rodents and neonatal humans. However three independent studies conclusively identified BAT in adult humans primarily behind the muscles of the lower neck and collar bone, as well as along the spine of the chest and the abdomen. β3-AR agonists have been shown to stimulate remodelling of WAT into BAT, determined histologically, or by the appearance of UCP1. The appearance of UCP1 in WAT in response to ZAG would suggest that it initiates a similar process. Previous studies have suggested a role for the β3-AR in the induction of UCP1 by ZAG. β3-AR agonists have been shown to induce upregulation of UCP1 in BAT through stimulation of p38 mitogen activated protein kinase (p38 MAPK) downstream of cyclic AMP/protein kinase A, leading to activation (phosphorylation) of peroxisome proliferator-activated receptor (PPAR) γ coactivator 1 (PCG-1α), as well as ATF-2, allowing the CRE and PPAR elements of the UCP1 enhancer to be occupied.

ZAG is a naturally occurring ligand with selective agonist activity towards the β3-AR. Very few proteins display such activity, although the hypotensive peptide adrenomedullin may also activate β3-AR leading to relaxation of ileal muscle. Since ZAG is much larger than the normal catecholamine agonists it is possible that activation occurs through allosteric modulation. However, previous studies using LMF have shown binding to be completely attenuated by propranolol, suggesting direct interaction with a β3-AR. It is likely that only part of the ZAG molecule is required for binding, since evidence suggested that tryptic fragments of a lipolytic factor (Mr about 5 kDa) were still biologically active. It is possible that certain groups in amino acids, such as serine hydroxyl, can mimic the hydrogen bonding interactions seen between catecholamines and the β3-AR. Molecular modelling studies may provide further information on the interactions involved. β3-AR agonists such as BRL37344 have been shown to increase ZAG expression in adipocytes, and induction of ZAG expression by ZAG has also been suggested to occur through a β3-AR. Thus the β3-AR is important in both the production and biological effects of ZAG, and ZAG is a natural agonist of β2- and β3-AR.

EXAMPLE 9

Use of Zinc-$\alpha_2$-glycoprotein in Skeletal Muscle Synthesis for Treatment of Cachexia The goal of the study was to explore the mechanism of net protein gain in ob/ob mice when treated with ZAG. In some ZAG treatment experiments it is observed that ob/ob mice lose significant body fat but simultaneously gain a (countervailing) amount of muscle mass as protein.

Protein synthesis was measured by the incorporation of L-[2,6-3H] phenylalanine into acid-insoluble material with 2 h incubation at 37° C. without phenol red and saturated with O2CO2 (95:5). The rate of protein synthesis was calculated by dividing the amount of protein-bound radioactivity by the amount of acid soluble radioactivity.

Protein degradation was determined by the release of tyrosine (21) from gastrocnemius muscle over 2 h in oxygenated Krebs-Henselit buffer containing 5 mM glucose and 0.5 mM cycloheximide.

Figure 30:
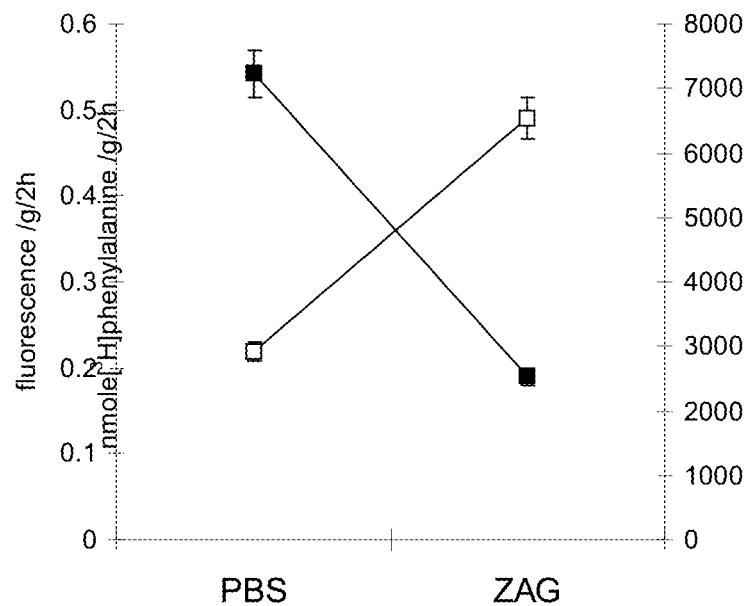
FIG. 30 is a graphical diagram showing decreased proteolysis and increased muscle synthesis in ZAG treated ob/ob mice.

The results shown in FIG. 30 indicate indicate that the net protein gain in skeletal muscle is a consequence of both a slowing of protein degradation and an increase in protein synthesis.

EXAMPLE 10

Figure 34:
FIG. 34 is a pictorial diagram of a Western blot showing ZAG in ob/ob mice following oral administration. Treatment with rhZAG administered orally causes an increase in endogenously expressed murine ZAG in plasma.
Figure 35:
FIG. 35 is a pictorial diagram of a Western blot showing ZAG expression in WAT from ob/ob mice treated with and without human ZAG (p.o.). Treatment with rhZAG administered orally causes an increase in endogenously expressed murine ZAG in WAT.
Figure 36:
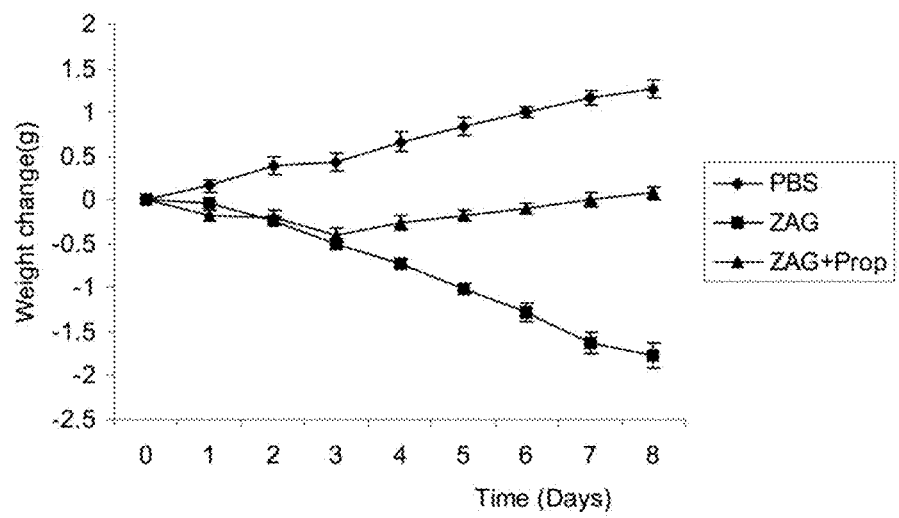
FIG. 36 is a graphical diagram showing weight change in ob/ob mice treated with and without ZAG (p.o.) in the absence or presence of propranolol, a gereral β-AR antagonist. Propranolol was increased from 20 to 40 mg/kg on day 3, after which change in weight loss altered from the negative slope of the ZAG-treated animals to the positive slope of the untreated animals.

Oral Administration of Zinc-$\alpha_2$-glycoprotein for Weight Loss and Reduction in Glucose The goal of the study was to explore the ability of ZAG to generate weight loss through fat loss and lowering of plasma and urinary glucose levels over an extended period of time and by means of oral administration of ZAG. Surprisingly, recombinant human ZAG administered orally was able to generate the same set of responses as intravenous administration of recombinant human ZAG, and was able to do so without entering the plasma space from the digestive space of the body. A novel mechanism of action is at work to transduce the signal of recombinant human ZAG present in the digestive space, causing generation of endogenous murine ZAG in the plasma space and WAT and other tissues, as seen in FIGS. 34 and 35.

50 ug per day of rhZAG was administered p.o. to Aston ob/ob mice. Oral dosing was achieved by assuming 5 mL/day consumption of water, and adding ZAG to achieve 50 ug per day dose based on that assumption. No attempt was made to correct for variations of consumption on a given day.

Figure 37:
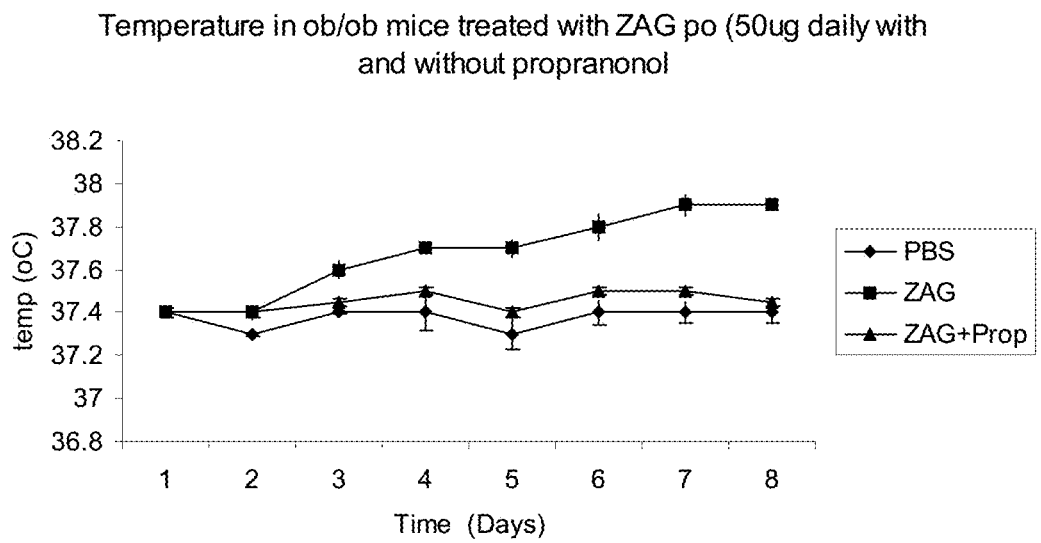
FIG. 37 is a graphical diagram showing change in body temperature in ob/ob mice treated with and without ZAG (p.o.) in the absence or presence of propranolol. Propranolol was increased from 20 to 40 mg/kg on day 3, after which body temperature of the ZAG+Prop animals tracked that of untreated animals.
Figure 40:
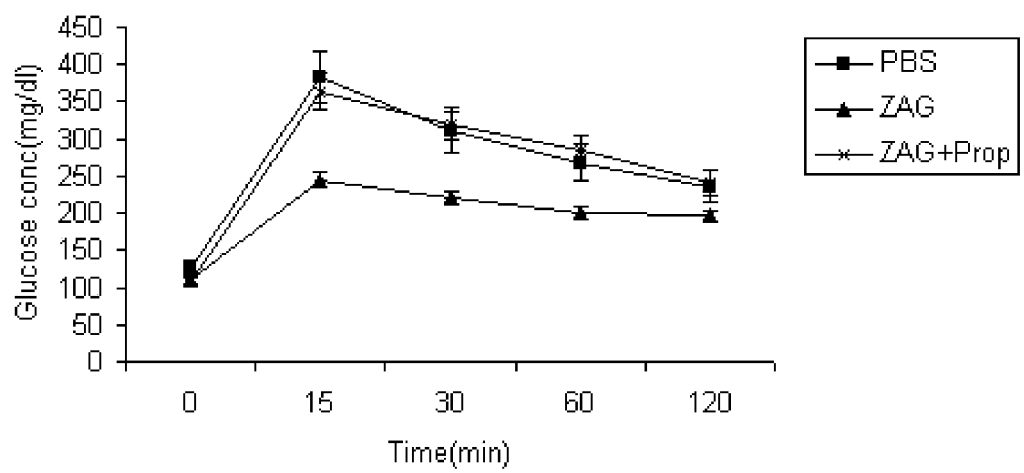
FIG. 40 is a graphical diagram showing glucose levels during a glucose tolerance test in ob/ob mice treated with and without ZAG (p.o.) in the absence or presence of propranolol.
Figure 41:
FIG. 41 is a pictorial diagram of a Western blot showing ZAG in ob/ob mice following oral administration. Treatment with rhZAG administered orally causes an increase in endogenously expressed murine ZAG in plasma.
Figure 42:
FIG. 42 is a pictorial diagram of a Western blot showing ZAG expression in WAT from ob/ob mice treated with and without human ZAG (p.o.).
Figure 43:
FIG. 43 is a pictorial diagram showing the effect of ZAG on protein synthesis and degradation in skeletal muscle of ob/ob mice.
Figure 44:
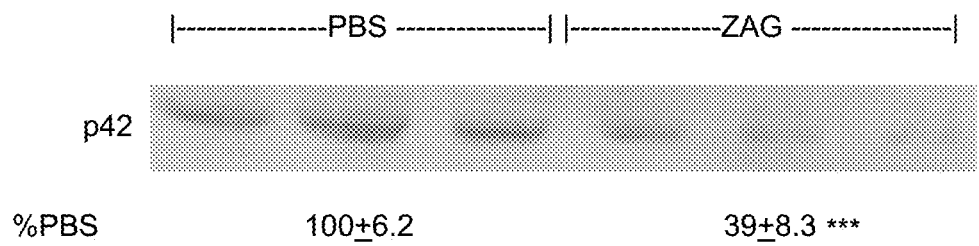
FIG. 44 is a pictorial diagram showing the effect of ZAG on signaling pathwasy in skeletal muscle of ob/ob mice.
Figure 45:
FIG. 45 is a pictorial diagram showing the effect of ZAG on protein synthesis and degradation in skeletal muscle of ob/ob mice.
Figure 46:
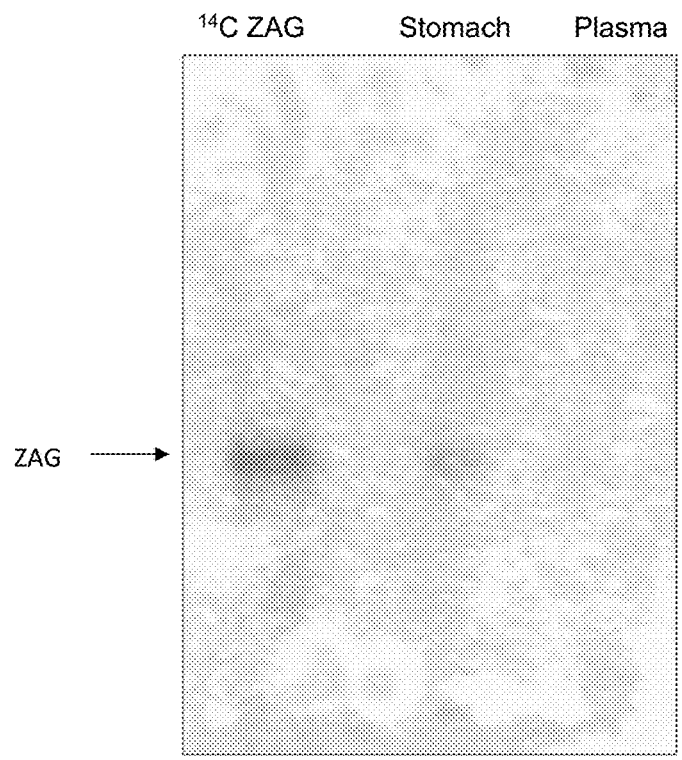
FIG. 46 is a pictorial diagram of a 14C ZAG autoradiograph showing stomach and plasma levels of ZAG from ob/ob mouse treated p.o., the samples being taken 24-hours post treatment.
Figure 47:
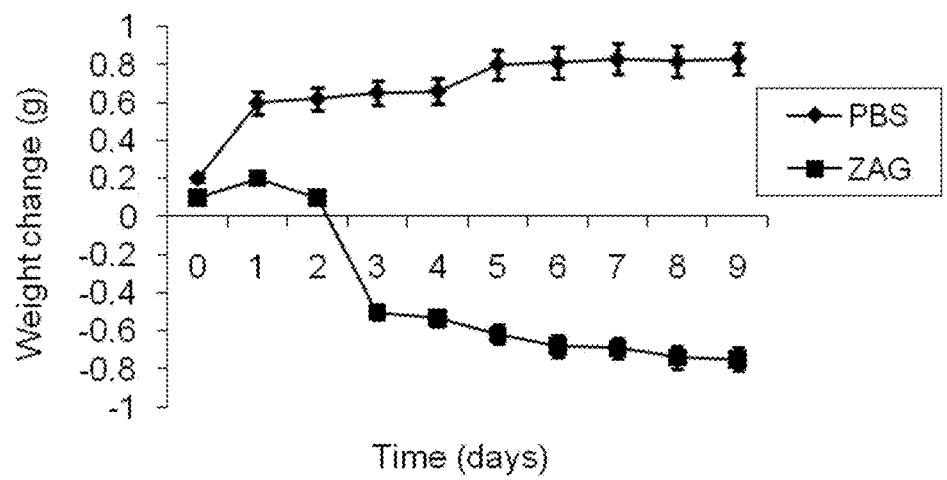
FIG. 47 is a graphical diagram showing weight change in ob/ob mice treated with and without 50 ug ZAG (p.o./gavage).
Figure 48:
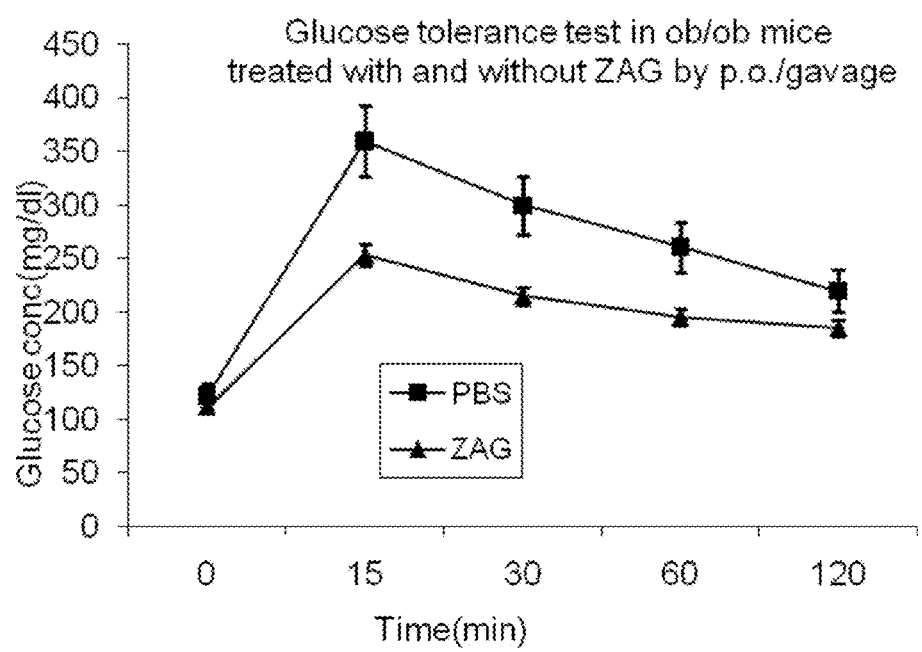
FIG. 48 is a graphical diagram showing glucose urine levels in ob/ob mice treated with and without 50 ug ZAG (p.o./gavage).
Figure 49:
FIG. 49 is a pictorial diagram of a Western blot. Anti-ZAG Diminishes Affects Caused by BRL37344 in vivo: Western blot of UCP3 in BAT of ob/ob mice treated with and without BRL in the absence or presence of Anti-ZAG. Treatment of ob/ob mice with BRL37344 causes an increase of UCP3 in BAT, an effect which is blocked by the administration of anti-ZAG antibodies.
Figure 50:
FIG. 50 is a pictorial diagram of a Western blot. ZAG administered orally to ob/ob mice causes an up-regulation of endogenous murine ZAG in plasma and in WAT. Western blot of mouse ZAG in p.o. rhZAG-dosed samples of plasma (top) and WAT (bottom).

ZAG administration p.o generally duplicates the results obtained by i.v. administration. This wide range of effects includes significant weight loss (FIGS. 31, 36, 41, 47), a slight increase in body temperature emblematic of increased energy expenditure (FIGS. 32, 37, 43), a lowering of urinary and plasma glucose (FIGS. 33, 42), and a significant improvement in response to the oral glucose tolerance test (FIGS. 40, 48).

The mechanism of action mirrors that of intravenous injection, with a critical difference. The mechanisms are similar in that there is a wide-ranging set of responses in WAT, BAT, plasma, liver and skeletal muscle that are identical. The critical difference is that the orally-administered rhZAG never enters the space occupied by blood and the body's organs. Instead the administered rhZAG remains in the digestive system space, persisting 24 hours or longer in the stomach. The surprising and critical difference in mechanism is that the animal responds to oral dosing of rhZAG by creating its own endogenous ZAG, which mediates the subsequent set of responses named above.

Three experiments are described in detail below.

Experiment One (8 Day Oral ZAG Study): 50 ug of ZAG was administered p.o. daily in drinking water. It was observed that weight loss, increase in body temperature and a lowering of urinary glucose occurred. An increase in murine ZAG in serum and WAT, but an absence of rhZAG in serum demonstrates that rhZAG administered orally is upregulating expression of mouse ZAG.

Experiment Two (8 Day Oral ZAG Plus Propranolol Study): 50 ug of ZAG administered p.o. daily, with and without propranolol. Propanolol blocks all of the effects of ZAG including decrease in body weight and blood glucose in the tolerance test, also blocking the rise in body temperature and the rise in plasma mouse ZAG, confirming that this occurs through a beta adrenergic receptor. Propranolol totally attenuates weight loss by ZAG as well as the increase in body temperature. It appears to do this by preventing the rise in mouse ZAG in the serum after oral administration of the rhZAG. The second blot shows there is no rhZAG in the serum, as would be expected if rhZAG remains sequestered in the GI tract without transfer to the bloodstream.

Figure 38:
FIG. 38 is a pictorial diagram of a Western blot showing ZAG using anti-mouse ZAG in mouse serum from mice treated with and without ZAG in the absence or presence of propranonol. Endogenous murine ZAG increases with treatment by orally administered rhZAG, and such increase is blocked by propranolol.
Figure 39:
FIG. 39 is a pictorial diagram of a Western blot showing ZAG using anti-human ZAG against mouse serum from mice treated with and without ZAG in the absence or presence of propranonol. Human ZAG is not detected in mouse serum with or without propranolol.

Thus oral ZAG works by binding to GI tract beta adrenergic receptors, leading to a rise in serum ZAG and the consequent effects on body weight and blood glucose. FIG. 38 shows that propranolol blocks the increase in murine serum ZAG due to treatment with rhZAG p.o. Additionally, FIG. 39 shows that human ZAG is not detected in mouse serum.

Experiment Three (Oral Study): ZAG administered p.o. daily over an extended time frame, with a recovery group split from the treated group beginning at 30 days (data not shown).

Weight loss, body temperature and decrease in urinary glucose mirror and extend results achieved by intravenous injection. Animals lost as much as 13.5% body weight at half way through the study. After half study duration of treatment, treated animals showed the following. In urinary glucose, 12 days passed before 50% reversion to control occurred, and complete reversion to control levels of urinary glucose occurred by the end of the study duration (data not shown). Body weight loss reached 13.5%, and at day study end the animals had reverted only 46% towards the control weights (data not shown). Like the action of ZAG when administered intravenously, orally-administered ZAG caused weight loss but not changes in activity (not shown), consumption of food (data not shown) or consumption of water (data not shown).

EXAMPLE 11

Administration of Zinc-$\alpha_2$-glycoprotein Achieves Loss of Body Fat and a Simultaneous Gain in Muscle Mass in Skeletal Muscles In some experiments it has been observed that the ob/ob mice will lose significant body fat but simultaneously gain a (countervailing) amount of muscle mass as protein. This has been explored and the net protein gain is due to a slowing of protein degradation and concomitant increase in protein synthesis (FIG. 30).

EXAMPLE 12

Figure 31:
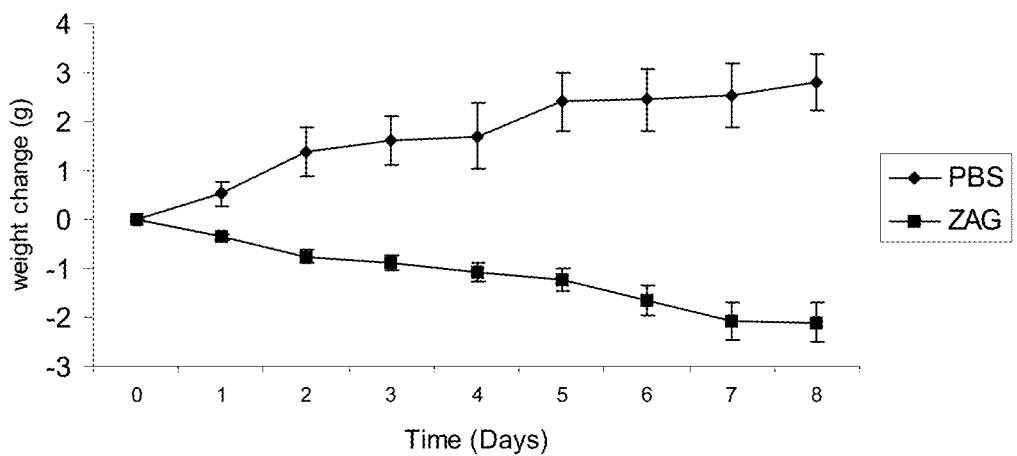
FIG. 31 is a graphical diagram showing weight change in ob/ob mice treated with and without ZAG.
Figure 32:
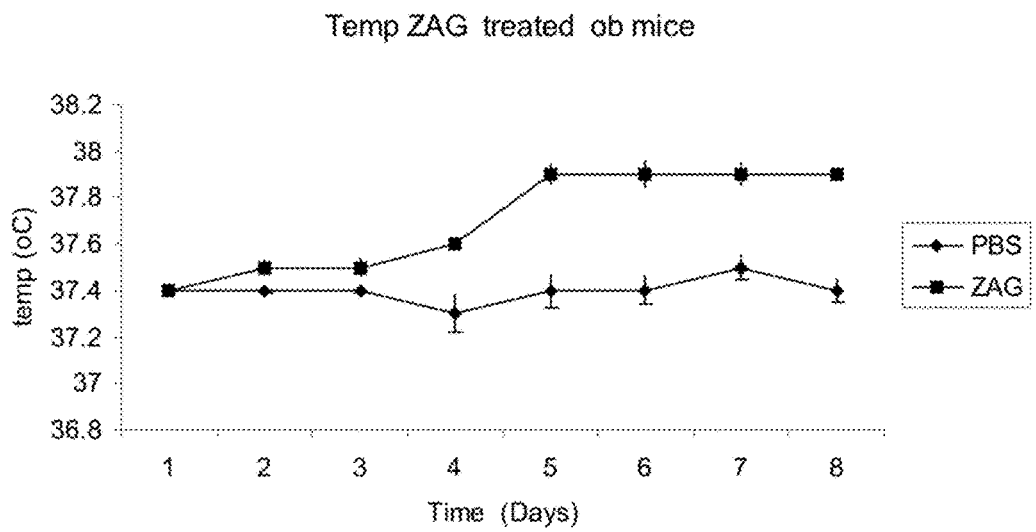
FIG. 32 is a graphical diagram showing body temperature in ob/ob mice treated with and without ZAG.
Figure 33:
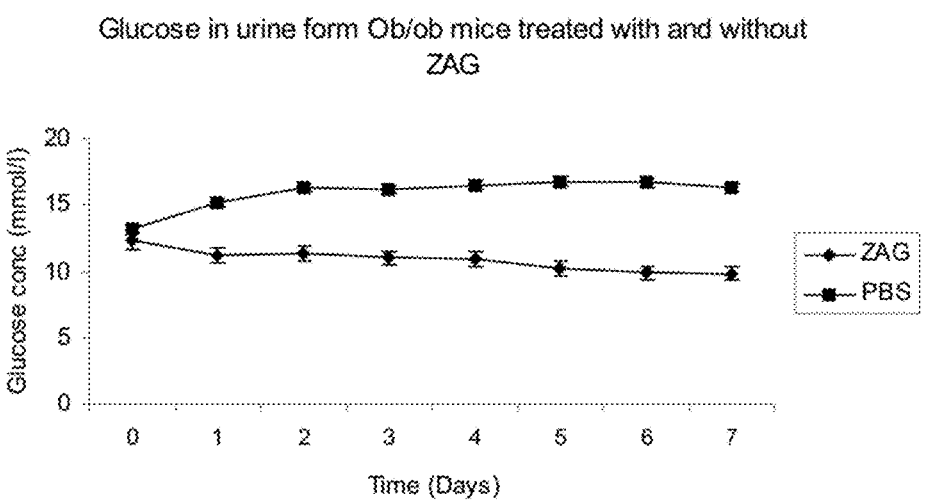
FIG. 33 is a graphical diagram showing urine glucose levels in ob/ob mice treated with and without ZAG.

Oral Administration of Zinc-α$_2$-glycoprotein Compared to I.V. Administration The goal of the study was to compare the efficacy of ZAG via various routes of administration. Mice were orally administered 50 μg ZAG or PBS (control). The results of are shown in FIGS. 31, 32, 33 (8 day oral ZAG study); 36, 37, 40 (8 day oral ZAG plus propranolol study); and FIGS. 47, 48 (oral ZAG gavage study). As shown in these repeated studies, ZAG was unexpectedly shown to be effective in bringing about weight change when administered orally by simply mixing low doses of ZAG in the drinking water of mice without requiring systemic absorption of administered ZAG. Typical oral dosing of proteins, such as insulin, can require up to 10× (or mega dosing) the intravenous dose to achieve the same level of efficacy and such limited efficacy requires systemic absorption of such proteins.

Additional data was generated (Table 6) showing that, surprisingly, oral dosing of ZAG achieved as much as 75% of the weight-loss efficacy of intravenous administration with exactly the same dose. Also, after 5 days of dosing, the efficacy of lowering of urinary glucose is equally as good when dosed orally or i.v.

Oral dosing with rhZAG causes the animals to generate endogenous ZAG in response, as shown in FIGS. 34, 35 and 38. Propranolol blocks the increase in murine serum ZAG due to treatment with rhZAG p.o. (FIG. 38), but administered human ZAG is not found in plasma (FIG. 39).

FIG. 38 is a Western blot of ZAG using Anti-mouse ZAG in mouse serum from Mice treated with and without ZAG in the absence or presence of propranonol. Human ZAG is not detected in mouse serum. FIG. 39 is a Western blot of ZAG using Anti-human ZAG in mouse serum from Mice treated with and without ZAG in the absence or presence of propranonol (FIG. 39).

TABLE 6

Body weight loss (and % of i.v. loss over the same time) due to daily dosing of ZAG at 50 ug/day in 70 g ob/ob mice by ROA for 8 or 20 days:

| ROA | 8 Days | 20 Days |
|---|---|---|
| intraveneous | −6.0% (100%) | −9.0% (100%) |
| oral-water(1) | −4.3% (72%) | −6.1% (68%) |
| oral-gavage(2) | −2.3% (38%) | N/A |
| oral-casein(3) | −3.4% (57%) | −6.8% (76%) |

(1) Literally in the drinking water
(2) Gavage places the ZAG dose directly into the stomach, by passing the digestive system path preceding the stomach (mouth, pharynx, esophagus)
(3) Casein was included with the ZAG in the drinking water.

Although the invention has been described with reference to the above example, it will be understood that modifications and variations are encompassed within the spirit and scope of the invention. Accordingly, the invention is limited only by the following claims.

---

What is claimed is:

1. A method for increasing a subject's endogenous level of a zinc-$\alpha_2$-glycoprotein (ZAG) comprising orally administering to the subject a formulation comprising an exogenous ZAG, wherein upregulated production of endogenous ZAG in the subject is detectable by obtaining one or more tissue or fluid samples from the subject and detecting an increase in the level of endogenous ZAG in the sample and an absence of a therapeutically effective level of exogenous ZAG in the sample, thereby increasing the subject's endogenous level of ZAG as compared to the level of ZAG prior to administration.

2. The method of claim 1, wherein the subject is human.

3. The method of claim 1, wherein the formulation is administered daily for at least 10 or 21 days.

4. The method of claim 1, wherein the formulation is administered daily for greater than one or two years.

5. The method of claim 1, wherein the formulation is administered twice daily, once every three days, weekly or monthly.

6. The method of claim 1, wherein the formulation is administered in combination with one or more agents selected from the group consisting of a β3 agonist and β-adrenergic receptor (β-AR) antagonist in any sequence or simultaneously.

7. The method of claim 6, wherein the β-AR antagonist is selected from the group consisting of a β2-adrenergic receptor (β2-AR) antagonist, a β1-adrenergic receptor (β1-AR) antagonist, and a (β3-adrenergic receptor (β3-AR) antagonist.

8. The method of claim 1, wherein the formulation is administered in combination with a glycemic reducing agent selected from insulin, glucagon-like peptide-1 (GLP-1), or analogs thereof in any sequence or simultaneously.

9. The method of claim 1, wherein the subject has one or more symptoms associated with diabetes, lipidystrophy, overweight, obesity, insulin resistance, elevated plasma levels of free fatty acids (NEFA), triglycerides, or glucose.

10. The method of claim 1, wherein the ZAG consists of the amino acid sequence set forth in SEQ ID NO: 1.

11. The method of claim 10, wherein the ZAG is conjugated to a non-protein polymer.

12. The method of claim 11, wherein the ZAG is sialylated, PEGylated, glycosylated, or modified to increase solubility or stability.

13. The method of claim 1, wherein the formulation comprises at least 5, 10, 25, 50, or100 mg of ZAG.

14. The method of claim 6, wherein the β3 agonist is selected from the group consisting of epinephrine (adrenaline), norepinephrine (noradrenaline), isoproterenol, isoprenaline, propranolol, alprenolol, arotinolol, bucindolol, carazolol, carteolol, clenbuterol, denopamine, fenoterol, nadolol, octopamine, oxyprenolol, pindolol, [(cyano)pindolol], salbuterol, salmeterol, teratolol, tecradine, trimetoquinolol, 3'-iodotrimetoquinolol, 3',5'-iodotrimetoquinolol, Amibegron, Solabegron, Nebivolol, AD-9677, AJ-9677, AZ-002, CGP-12177, CL-316243, CL-317413, BRL-37344, BRL-35135, BRL-26830, BRL-28410, BRL-33725, BRL-37344, BRL-35113, BMS-194449, BMS-196085, BMS-201620, BMS-210285, BMS-187257, BMS-187413, the CONH2 substitution of SO3H of BMS-187413, the racemates of BMS-181413, CGP-20712A, CGP-12177, CP-114271, CP-331679, CP-331684, CP-209129, FR-165914, FR-149175, ICI-118551, ICI-201651, ICI-198157, ICI-D7114, LY-377604, LY-368842, KTO-7924, LY-362884, LY-750355, LY-749372, LY-79771, LY-104119, L-771047, L-755507, L-749372, L-750355, L-760087, L-766892, L-746646, L-757793, L-770644, L-760081, L-796568, L-748328, L-748337, Ro-16-8714, Ro-40-2148, (−)-RO-363, SB-215691, SB-220648, SB-226552, SB-229432, SB-251023, SB-236923, SB-246982, SR-58894A, SR-58611, SR-58878, SR-59062, SM-11044, SM-350300, ZD-7114, ZD-2079, ZD-9969, ZM-215001, and ZM-215967.

15. The method of claim 1, wherein the levels of glucose and fat decrease as compared to the glucose and fat levels prior to administration of the formulation.

16. The method of claim 1, wherein the one or more tissue or fluid samples are selected from the group consisting of blood, plasma, adipose tissue, WAT, BAT, liver, and skeletal muscle.

* * * * *